(12) United States Patent
Scott et al.

(10) Patent No.: US 9,627,120 B2
(45) Date of Patent: Apr. 18, 2017

(54) MAGNETIC THROTTLING AND CONTROL: MAGNETIC CONTROL

(75) Inventors: Daniel J. Scott, Dallas, TX (US); Raul Fernandez, Arlington, TX (US); Richard A. Bergs, Grand Prairie, TX (US); Jeffrey A. Cadeddu, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 223 days.

(21) Appl. No.: 12/783,449

(22) Filed: May 19, 2010

(65) Prior Publication Data
US 2011/0285488 A1 Nov. 24, 2011

(51) Int. Cl.
| | |
|---|---|
| *H01F 7/02* | (2006.01) |
| *A61B 34/00* | (2016.01) |
| *A61B 17/00* | (2006.01) |
| *A61B 34/30* | (2016.01) |
| *A61B 34/20* | (2016.01) |
| *A61B 90/00* | (2016.01) |

(52) U.S. Cl.
CPC ......... *H01F 7/0221* (2013.01); *A61B 34/70* (2016.02); *A61B 34/73* (2016.02); *A61B 34/76* (2016.02); *A61B 2017/00026* (2013.01); *A61B 2017/00283* (2013.01); *A61B 2017/00477* (2013.01); *A61B 2017/00876* (2013.01); *A61B 2034/2051* (2016.02); *A61B 2034/2055* (2016.02); *A61B 2034/2063* (2016.02); *A61B 2034/302* (2016.02); *A61B 2034/303* (2016.02); *A61B 2090/065* (2016.02); *H01F 7/0226* (2013.01)

(58) Field of Classification Search
CPC .... H01F 7/0221; H01F 7/0231; H01F 7/0236; H01F 7/0242; H01F 7/0247; H01F 7/0257
USPC .......................................... 606/1
See application file for complete search history.

(56) References Cited

U.S. PATENT DOCUMENTS

| | | | | |
|---|---|---|---|---|
| 5,367,508 | A * | 11/1994 | Haba ..................... | 369/13.17 |
| 5,711,299 | A * | 1/1998 | Manwaring et al. ......... | 600/417 |
| 5,879,549 | A * | 3/1999 | Caiozza .................. | 210/186 |
| 6,171,504 | B1 * | 1/2001 | Patterson ................ | 210/695 |
| 6,537,196 | B1 * | 3/2003 | Creighton et al. .......... | 600/12 |
| 6,656,194 | B1 | 12/2003 | Gannoe et al. ............. | 606/153 |
| 6,781,613 | B2 * | 8/2004 | Matsuo et al. ............. | 347/159 |

(Continued)

FOREIGN PATENT DOCUMENTS

| | | |
|---|---|---|
| WO | WO 2005/002415 | 1/2005 |
| WO | WO 2007/130382 | 11/2007 |

(Continued)

OTHER PUBLICATIONS

U.S. Appl. No. 12/899,327, filed Oct. 3, 2010.

(Continued)

*Primary Examiner* — William Thomson
*Assistant Examiner* — John R Downey
(74) *Attorney, Agent, or Firm* — Norton Rose Fulbright US LLP

(57) ABSTRACT

Apparatuses and systems for enabling electrical communication with a device positionable within a body cavity of a patient. Apparatuses and systems for magnetically positioning a device within a body cavity of a patient. Medical devices. Methods of use.

6 Claims, 38 Drawing Sheets

(56) References Cited

U.S. PATENT DOCUMENTS

| | | | |
|---|---|---|---|
| 6,831,285 B2 * | 12/2004 | Hol et al. | 250/548 |
| 7,429,259 B2 | 9/2008 | Cadeddu et al. | 606/1 |
| 7,691,103 B2 | 4/2010 | Fernandez et al. | 606/41 |
| 7,744,562 B2 * | 6/2010 | Jahns et al. | 604/68 |
| 2003/0114731 A1 | 6/2003 | Cadeddu et al. | 600/114 |
| 2007/0135686 A1 | 6/2007 | Pruitt et al. | 600/214 |
| 2007/0255109 A1 | 11/2007 | Stein et al. | 600/214 |
| 2008/0167522 A1 | 7/2008 | Giordano et al. | 600/104 |
| 2008/0269779 A1 | 10/2008 | Cadeddu et al. | 606/130 |
| 2008/0281187 A1 * | 11/2008 | Massengill et al. | 600/424 |
| 2008/0312500 A1 | 12/2008 | Asada et al. | 600/109 |
| 2009/0005636 A1 | 1/2009 | Pang et al. | 600/102 |
| 2009/0237080 A1 * | 9/2009 | Kato et al. | 324/319 |
| 2010/0030028 A1 | 2/2010 | Cabrera et al. | 600/127 |
| 2010/0063538 A1 | 3/2010 | Spivey et al. | 606/208 |
| 2010/0141366 A1 * | 6/2010 | Sprague et al. | 335/219 |
| 2010/0256636 A1 | 10/2010 | Fernandez et al. | 606/49 |
| 2011/0079511 A1 * | 4/2011 | Hellmich et al. | 204/298.13 |
| 2011/0087223 A1 | 4/2011 | Spivey | 606/49 |
| 2011/0087224 A1 | 4/2011 | Cadeddu et al. | 606/49 |
| 2011/0160752 A1 * | 6/2011 | Aguirre | 606/153 |
| 2011/0283822 A1 | 11/2011 | Cadeddu et al. | 74/89.23 |
| 2011/0284014 A1 | 11/2011 | Cadeddu et al. | 128/899 |
| 2012/0062992 A1 * | 3/2012 | Kimoto | 359/484.03 |

FOREIGN PATENT DOCUMENTS

| | | |
|---|---|---|
| WO | WO 2010/056716 | 5/2010 |
| WO | WO 2010/083480 | 7/2010 |
| WO | WO 2011/044468 | 4/2011 |
| WO | WO 2011/044471 | 4/2011 |
| WO | WO 2011/146691 | 11/2011 |
| WO | WO 2011/146709 | 11/2011 |

OTHER PUBLICATIONS

International Search Report in PCT/US2011/037105, dated Feb. 9, 2012.

Written Opinion issued in PCT/US2011/037105, dated Feb. 9, 2012.

* cited by examiner

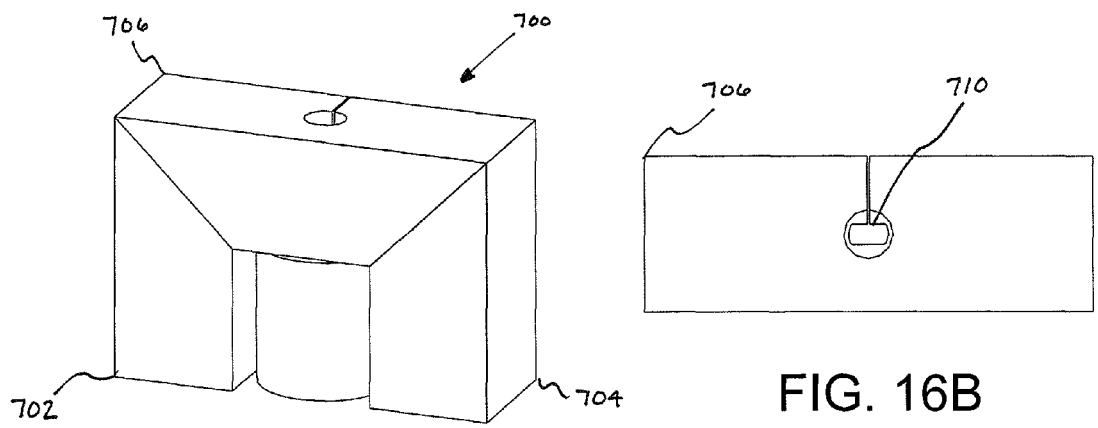
FIG. 16A
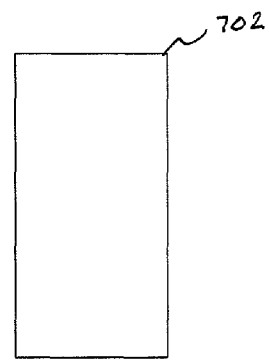
FIG. 16B
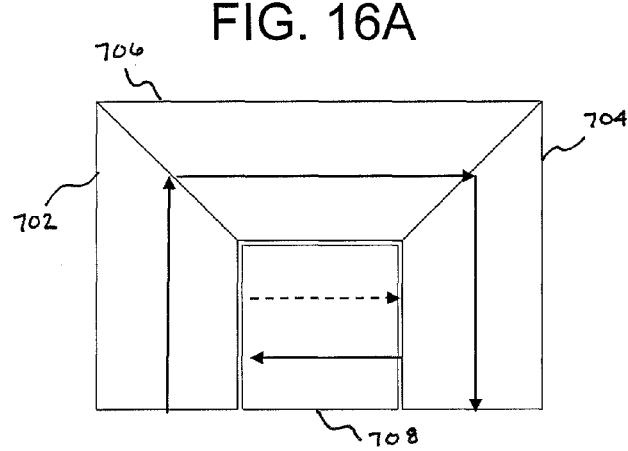
FIG. 16C
FIG. 16D
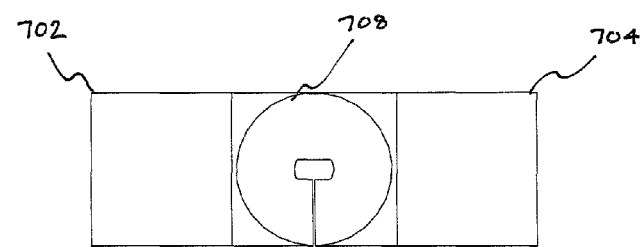
FIG. 16E

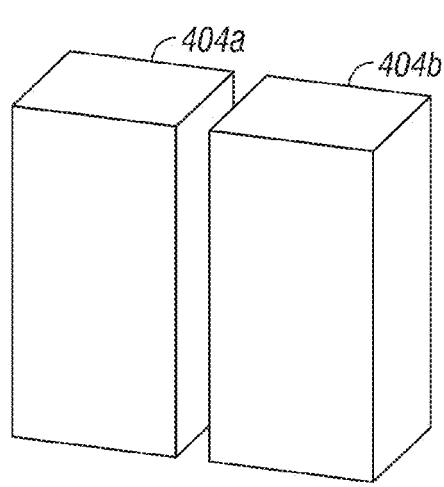
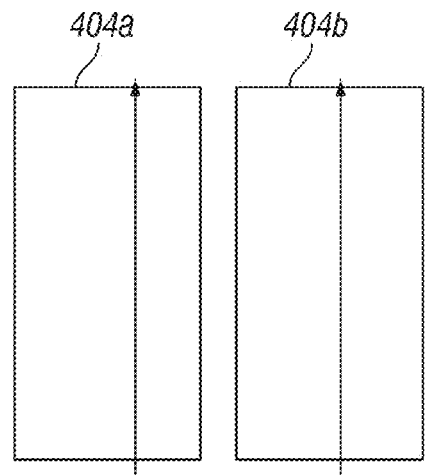
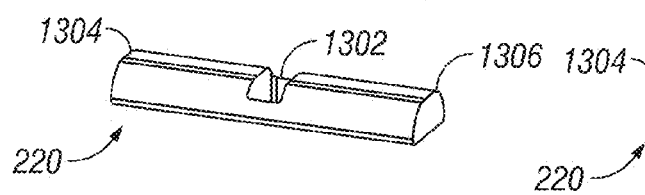
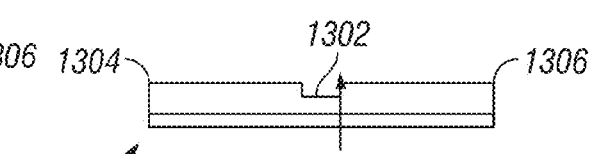
FIG. 33A
FIG. 33B
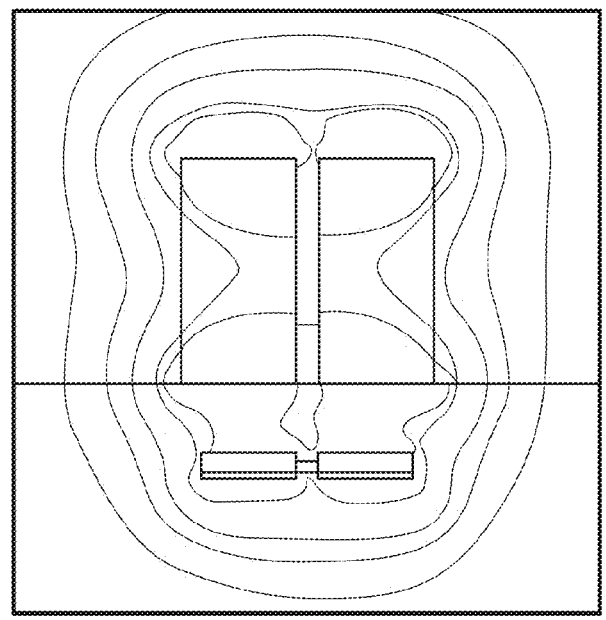
FIG. 33C

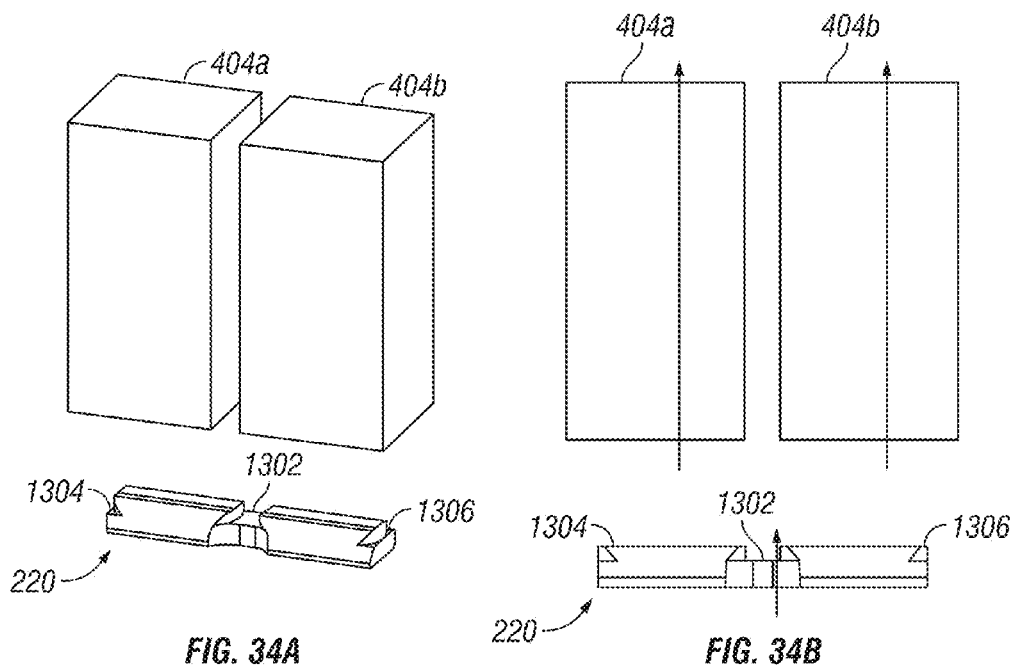
FIG. 34A
FIG. 34B
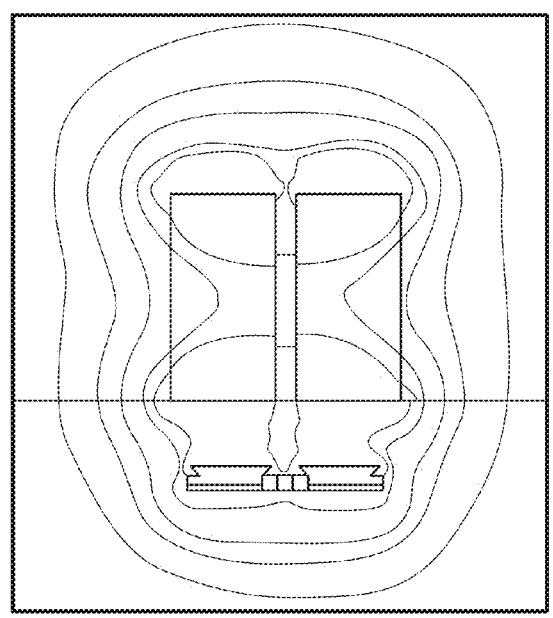
FIG. 34C

MAGNETIC THROTTLING AND CONTROL: MAGNETIC CONTROL

BACKGROUND

1. Field of the Invention

The present invention relates generally to medical devices, apparatuses, systems, and methods, and, more particularly, but not by way of limitation, to medical devices, apparatuses, systems, and methods for performing medical procedures at least partially within a body cavity of a patient.

2. Description of Related Art

For illustration, the background is described with respect to medical procedures (e.g., surgical procedures), which can include laparoscopy, transmural surgery, and endoluminal surgery, including, for example, natural orifice transluminal endoscopic surgery (NOTES), single-incision laparoscopic surgery (SILS), and single-port laparoscopy (SLP).

Compared with open surgery, laparoscopy can result in significantly less pain, faster convalescence and less morbidity. NOTES, which can be an even less-invasive surgical approach, may achieve similar results. However, issues such as eye-hand dissociation, a two-dimensional field-of-view, instrumentation with limited degrees of freedom, and demanding dexterity requirements can pose challenges for many laparoscopic and endoscopic procedures. One limitation of laparoscopy can be the fixed working envelope surrounding each trocar. As a result, multiple ports may be used to accommodate changes in position of the instruments or laparoscope, for example, to improve visibility and efficiency. However, the placement of additional working ports may contribute to post-operative pain and increases risks, such as additional bleeding and adjacent organ damage.

The following published patent applications include information that may be useful in understanding the present medical devices, systems, and methods, and each is incorporated by reference in its entirety: (1) International Application No. PCT/US2009/063987, filed on Nov. 11, 2009; (2) U.S. patent application Ser. No. 10/024,636, filed Dec. 14, 2001, and published as Pub. No. US 2003/0114731; (3) U.S. patent application Ser. No. 10/999,396, filed Nov. 30, 2004, published as Pub. No. US 2005/0165449 and issued as U.S. Pat. No. 7,429,259; (4) U.S. patent application Ser. No. 11/741,731, filed Apr. 28, 2007, published as Pub. No. US 2007/0255273 and issued as U.S. Pat. No. 7,691,103; (5) U.S. patent application Ser. No. 12/146,953, filed Jun. 26, 2008, and published as Pub. No. US 2008/0269779; and (6) U.S. patent application Ser. No. 12/755,312, filed on Apr. 6, 2010.

SUMMARY

Some embodiments of the present medical devices comprising an apparatus or platform at least partially defined by a length and a maximum transverse perimeter. In some embodiments, the maximum transverse perimeter may be 5 inches, 6 inches, 7 inches, 8 inches, 9 inches, or 10 inches Some embodiments comprise a maximum volume of approximately 64 cubic inches, 32 cubic inches, 27 cubic inches, 24 cubic inches, or 16 cubic inches.

Some embodiments include an apparatus, a device, and/or a primary magnetic field source. In some embodiments, the present apparatuses, devices, primary magnetic field sources, and/or any or all of the three, and/or associated components, may be sterile (e.g., before being used in surgery). In some embodiments, the present apparatuses, devices, and/or primary magnetic field sources may be sterilized or may undergo a sterilization process. In some embodiments, apparatus, device, or primary magnetic field source and associated components may be placed in a sterile, sealed packaging, which may be removed before surgery. In other embodiments, apparatus, device, or primary magnetic field source may be wrapped in a sterile barrier (e.g. a sheet, a paper or a film) before being used in surgery. In some embodiments, the present apparatuses, devices, and/or primary magnetic field sources may be individually sterile or may comprise a sterile material.

In embodiments where primary magnetic field source is not removable from apparatus or device, primary magnetic field source may or may not be separately sterilized and/or sterile. In embodiments where primary magnetic field source is configured to be removable from apparatus or device, primary magnetic field source may be sterile or may be separately sterilized and/or sterile. In embodiments where primary magnetic field source is configured to be removable from apparatus or device and primary magnetic field source will not contact the patient during surgery, primary magnetic field source may or may not be separately sterilized and/or sterile.

Any embodiment of any of the present systems, apparatuses, devices, and methods can consist of or consist essentially of—rather than comprise/include/contain/have—any of the described elements and/or features. Thus, in any of the claims, the term "consisting of" or "consisting essentially of" can be substituted for any of the open-ended linking verbs recited above, in order to change the scope of a given claim from what it would otherwise be using the open-ended linking verb.

A system is presented. In one embodiment, the system includes a first platform. The first platform may be referred to as an "object," an "internal platform," a "target," a "device" or a "surgical device." The first platform may be inserted within a body cavity of a patient. Additionally, the first platform may include a first anchor magnet and a first pivot magnet. In such an embodiment, the system may also include a second platform. The second platform may be referred to as an "apparatus," or an "external unit." The second platform may be magnetically coupled to the first platform through a tissue. The second platform may include a second anchor magnet and a second pivot magnet. In one embodiment, the second anchor magnet may be magnetically coupled to the first anchor magnet and the second pivot magnet may be magnetically coupled to the first pivot magnet. In particular, the second anchor magnet may generate a stronger magnetic field than can the second pivot magnet.

In a further embodiment, the first anchor magnet and the second anchor magnet may anchor the first platform to a position corresponding to a position of the second platform. The second pivot magnet may cause the first platform to rotate about a vertical axis in response to corresponding movement of the second pivot magnet.

In a particular embodiment, the second anchor magnet is larger than the second pivot magnet. Additionally, the first anchor magnet and the second anchor magnet may have the same direction of magnetization as the first pivot magnet and the second pivot magnet. Alternatively, the first anchor magnet and the second anchor magnet may have a different direction of magnetization from the first pivot magnet and the second pivot magnet.

Another embodiment of a system is described. In this embodiment, the system includes a first platform and a second platform. The first platform may be inserted within a body cavity of a patient. Additionally, the first platform may include three or more first platform magnets. Each first platform magnet may have a direction of magnetization that is opposite to a direction of magnetization of an adjacent first platform magnet. As used herein, the term "adjacent" means the nearest magnet in the same platform. If a plurality of magnets are equidistant from a particular magnet then the plurality of magnets are adjacent to the particular magnet. In one embodiment, the second platform may be magnetically coupled to the first platform through a tissue. The second platform may include three or more second platform magnets. In one embodiment, each second platform magnet has a direction of magnetization that is opposite to a direction of magnetization of an adjacent second platform magnet and that corresponds to a direction of magnetization of a first platform magnet.

In one embodiment, the first platform includes four first platform magnets. Each of the four first platform magnets may create a magnetic pole, where one of the magnetic poles has a polarity that is opposite a polarity of an adjacent magnetic pole. In a further embodiment, the second platform may include four second platform magnets.

An apparatus is also presented. In one embodiment, the apparatus includes a platform configured to be magnetically coupled to an object disposed within a body cavity of a patient through a tissue. The platform may include a first magnet having an N pole and an S pole along a horizontal axis. The platform can have a longitudinal axis and the first magnet has an N pole and an S pole along an axis that is more parallel with than perpendicular to the longitudinal axis. The platform may also include a second magnet having an N pole and an S pole. The second magnet may be disposed along the horizontal axis such that the N poles of the first and second magnets are closer to each other than are the S poles of the first and second magnets. Each of the components of the apparatus may be sterilized and/or sterile. For example, the apparatus may include a sterilized and/or sterile platform comprising at least one of a magnetically-attractive material and a materially capable of being magnetically-charged. Additionally, the apparatus may be provided in sterile packaging.

An embodiment of the apparatus includes a spacer disposed between the first magnet and the second magnet. The spacer may form a gap between the first magnet and the second magnet. Additionally, the apparatus may include a control mechanism configured to adjust the gap between the first magnet and the second magnet. In another embodiment, the apparatus includes a third magnet disposed between the first magnet and the second magnet. The third magnet may be an electromagnet. Additionally, the apparatus may include a current source coupled to the electromagnet and a control device for adjusting a level of a current provided to the electromagnet by the current source.

Another embodiment of an apparatus is described. For example, the apparatus may include a platform configured to be magnetically coupled to an object disposed within a body cavity of a patient through a tissue. The platform may include an electromagnet coupled to the platform and a permanent magnet coupled to the electromagnet. In particular, an N pole of the electromagnet is coupled to an N pole of the permanent magnet and an S pole of the electromagnet is coupled to an S pole of the permanent magnet.

The electromagnet may include a ferromagnetic core that includes a first electromagnetic flux channel and a second electromagnetic flux channel. The apparatus may also include a first electromagnetic flux channel that has a first focusing pad coupled to one of the N and S poles of the permanent magnet. Similarly, the second electromagnetic flux channel has a second focusing pad coupled to the other of the N and S poles of the permanent magnet.

The apparatus may also include a current source coupled to the electromagnet. The apparatus may also include a control device for adjusting a level of a current provided to the electromagnet by the current source. In particular, the electromagnet may generate a variable amount of magnetic flux.

Another embodiment of an apparatus may include a platform configured to be magnetically coupled to an object disposed within a body cavity of a patient through a tissue, where the platform includes a magnet assembly and a magnetic field modifier. The magnetic assembly may have a first leg, a second leg, and a bridge extending from the first leg to the second leg. The magnetic field modifier may interfere with a magnetic field generated by the magnet assembly.

In one embodiment, the bridge is in direct contact with the first and second legs. Alternatively, the bridge is not in direct contact with the first and second legs. The bridge may comprise a ferromagnetic material.

In a particular embodiment, the first leg includes a first magnet having a first direction of magnetization. The second leg may include a second magnet having a second direction of magnetization opposite the first direction of magnetization. In one embodiment, the bridge may include a third magnet having a third direction of magnetization that is more perpendicular to than parallel with the first direction of magnetization. The magnetic field modifier may include a magnet having a direction of magnetization that is more perpendicular to than parallel with the first direction of magnetization.

Additionally, the apparatus may include an adjustment mechanism coupled to the magnetic field modifier. The adjustment mechanism may adjust a position of the magnetic field modifier. The adjustment mechanism may change a location of a magnetic pole created by the magnetic field modifier. In particular, the magnetic field modifier may be rotatable about an axis.

In one embodiment, the first leg has a first leg surface, the second leg has a second leg surface, the bridge has two bridge surfaces, the first leg surface is oriented at a 45-degree angle to one of the two bridge surfaces, and the second leg surface is oriented at a 45-degree angle to the other of the two bridge surfaces. Alternatively, the first leg has a first leg surface, the second leg has a second leg surface, the bridge has a bridge surface, the first leg surface is parallel to the bridge surface, and the second leg surface is parallel to the bridge surface. In another alternative embodiment, the first leg partially encloses the magnetic field modifier, and the second leg partially encloses the magnetic field modifier. In still another embodiment, the first leg has a first leg surface, the second leg has a second leg surface, the bridge has a bridge surface, the first leg surface is parallel to the bridge surface, and the second leg surface is parallel to the bridge surface.

In one embodiment, the magnetic field modifier is rotatable about an axis that is more perpendicular to than parallel with the first direction of magnetization. In a further embodiment, the magnetic field modifier may include two pieces.

Another embodiment of an apparatus is described. In one embodiment, the apparatus includes a platform configured to be magnetically coupled to an object disposed within a body cavity of a patient through a tissue. The platform may include a magnet assembly and a magnetic field modifier. The magnet assembly may have a first leg, a second leg, and a bridge extending from the first leg to the second leg. The magnetic field modifier may interfere with a magnetic field generated by the magnet assembly, the magnetic field modifier being positioned between the first and second legs.

In one embodiment, the bridge is in direct contact with the first and second legs. Alternatively, the bridge is not in direct contact with the first and second legs. The bridge may include a ferromagnetic material.

In a particular embodiment, the first leg includes a first magnet having a first direction of magnetization. The second leg may include a second magnet having a second direction of magnetization opposite the first direction of magnetization. The bridge may include a third magnet having a third direction of magnetization that is more perpendicular to than parallel with the first direction of magnetization. In this embodiment, the magnetic field modifier may include a magnet having a direction of magnetization that is more perpendicular to than parallel with the first direction of magnetization.

The apparatus may also include an adjustment mechanism coupled to the magnetic field modifier and configured to adjust a position of the magnetic field modifier. The adjustment mechanism may change a location of a magnetic pole created by the magnetic field modifier. For example, the magnetic field modifier may be rotatable about an axis.

In one embodiment, the first leg has a first leg surface, the second leg has a second leg surface, the bridge has two bridge surfaces, the first leg surface is oriented at a 45-degree angle to one of the two bridge surfaces, and the second leg surface is oriented at a 45-degree angle to the other of the two bridge surfaces. Alternatively, the first leg has a first leg surface, the second leg has a second leg surface, the bridge has a bridge surface, the first leg surface is parallel to the bridge surface, and the second leg surface is parallel to the bridge surface. In another embodiment, the first leg partially encloses the magnetic field modifier, and the second leg partially encloses the magnetic field modifier. In still another embodiment, the first leg has a first leg surface, the second leg has a second leg surface, the bridge has a bridge surface, the first leg surface is parallel to the bridge surface, and the second leg surface is parallel to the bridge surface.

The magnetic field modifier may be rotatable about an axis that is more perpendicular to than parallel with the first direction of magnetization. More specifically, the magnetic field modifier may include two pieces.

Another embodiment of an apparatus is described. As with several other embodiments, the apparatus may include a platform configured to be magnetically coupled to an object disposed within a body cavity of a patient through a tissue. In this embodiment, however, the platform may include a first rotatable magnet and a second rotatable magnet coupled to the platform. The first rotatable magnet may rotate about a first axis. In particular, the first rotatable magnet may have a direction of magnetization that is transverse to the first axis. Similarly, the second rotatable magnet may rotate about a second axis. The second rotatable magnet may also have a direction of magnetization that is transverse to the second axis.

In one embodiment, the platform further includes a coupler to which the first and second rotatable magnets are rotatably coupled. In particular, the first and second rotatable magnets may be coupled to the coupler such that the first axis and the second axis are more parallel than perpendicular.

In such an embodiment, the first rotatable magnet and the second rotatable magnet are configured to emit interfering magnetic fields. The apparatus may include an adjustment mechanism configured to rotate at least one of the first rotatable magnet and the second rotatable magnet, thereby adjusting the level of interference between the magnetic fields produced by the first rotatable magnet and the second rotatable magnet.

In one embodiment, the platform may include a third magnet positioned between the first and second rotatable magnets. In a further embodiment, the platform may include a fourth rotatable magnet axially aligned with the first rotatable magnet, a fifth rotatable magnet axially aligned with the second rotatable magnet, and a sixth magnet positioned between the fourth and fifth rotatable magnets.

Another embodiment of an apparatus is presented. As with the other embodiments, this embodiment also includes a platform configured to be magnetically coupled to an object disposed within a body cavity of a patient through a tissue. In this embodiment, the platform includes a first magnet having a first direction of magnetization, a second magnet having a second direction of magnetization opposite the first direction of magnetization, and a third magnet disposed between the first and second magnets and having a third direction of magnetization that is more perpendicular than parallel to each of the first and second directions of magnetization.

In a further embodiment, the first magnet may include an N pole and an S pole. The second magnet may include an N pole and an S pole. Additionally, the third magnet may include an N pole and an S pole. In such an embodiment, the N pole of the first magnet may be coupled to the N pole of the third magnet, and the S pole of the second magnet may be coupled to the S pole of the third magnet. Additionally, the apparatus may include an adjustment mechanism coupled to the third magnet and configured to adjust the position of the third magnet relative to the first and second magnets.

Another embodiment of an apparatus includes a platform configured to be magnetically coupled to an object disposed within a body cavity of a patient through a tissue, the first platform having a longitudinal axis. In this embodiment, the platform may include a first magnet and a second magnet coupled to the platform.

The a first magnet may have an N pole and an S pole along a first magnet axis that is more perpendicular to than parallel with the longitudinal axis. In particular, the first magnet may have a first magnet longitudinal axis that is more perpendicular to than parallel with the first magnet axis, and a first longitudinal dimension that is taken along a line that is parallel to the first magnet longitudinal axis. In such an embodiment, the first longitudinal dimension is greater than any dimension of the first magnet that is taken along a line that is perpendicular to the first magnet longitudinal axis. The second magnet may have an N pole and an S pole along a second magnet axis that is more perpendicular to than parallel with the longitudinal axis. The second magnet may have a second magnet longitudinal axis that is more perpendicular to than parallel with the second magnet axis, and a second longitudinal dimension that is taken along a line that is parallel to the second magnet longitudinal axis. In such an embodiment, the second longitudinal dimension is greater than any dimension of the second magnet that is taken along a line that is perpendicular to the second magnet longitudinal axis.

In a further embodiment, a second platform may be configured to be inserted within a body cavity of a patient and magnetically coupled to the first platform across a tissue, the second platform having a second platform magnet that has an N pole and an S pole along an axis that is more perpendicular to than parallel with the first magnet axis.

Alternatively, the second platform may have a single second platform magnet that has an N pole and an S pole along an axis that is more perpendicular to than parallel with the first magnet axis. The apparatus may also include a top piece coupled to the first and second magnets.

A medical device is also described. In one embodiment, the medical device includes an internal platform configured to be inserted within a body cavity of a patient, the internal platform having a unitary magnet having a length taken along a longitudinal axis that is greater than any dimension of the unitary magnet taken along a line that is perpendicular to the longitudinal axis, the unitary magnet having a top and a bottom and defining a central opening that extends from the top to the bottom.

In a further embodiment, the unitary magnet is the only magnet of the internal platform. The medical device may also include an external platform configured to be placed outside the body cavity and magnetically coupled to the internal platform through a tissue. In such an embodiment, the external platform may include a first magnet and a second magnet, the first magnet being configured to be magnetically coupled to a first portion of the unitary magnet on one side of the central opening and the second magnet being configured to be magnetically coupled to a second portion of the unitary magnet on another side of the central opening.

Another embodiment of a medical device includes an internal platform configured to be inserted within a body cavity of a patient, the internal platform including a unitary magnet that has a top, a bottom, a first longitudinal portion, a second longitudinal portion, and a central opening that extends from the top to the bottom and separates the first and second longitudinal portions, the unitary magnet producing a magnetic field that is stronger over each of the first and second longitudinal portions than over the central opening. Here, the unitary magnet is the only magnet of the internal platform. This embodiment may also include an external platform configured to be placed outside the body cavity and magnetically coupled to the internal platform through a tissue, where the external platform may include a first magnet and a second magnet, the first magnet being configured to be magnetically coupled to the first longitudinal portion of the unitary magnet and the second magnet being configured to be magnetically coupled to the second longitudinal portion of the unitary magnet.

Another medical device includes an internal platform configured to be inserted within a body cavity of a patient, the internal platform including a unitary magnet having a first portion separated from a second portion by a central portion, where the central portion is thinner than the first and second portions. Similarly, the unitary magnet is the only magnet of the internal platform.

Additional embodiments of the medical device include an internal platform configured to be inserted within a body cavity of a patient. In one embodiment, the internal platform includes a unitary magnet that has a first portion separated from a second portion by a central portion, where the first and second portions are wider than the central portion. In another embodiment, the internal platform includes a unitary magnet that has a first portion separated from a second portion by a central portion, where the first and second portions are wider than the central portion and the central portion is thinner than the first and second portions. In still another embodiment, the internal platform includes a unitary magnet having a first portion separated from a second portion by a central portion, and the unitary magnet produces a magnetic field that is stronger over each of the first and second portions than over the central portion.

Each of these various embodiments of the medical device may include an external platform configured to be placed outside the body cavity and magnetically coupled to the internal platform through a tissue, where the external platform may include a first magnet and a second magnet, the first magnet being configured to be magnetically coupled to the first portion of the unitary magnet and the second magnet being configured to be magnetically coupled to the second portion of the unitary magnet.

A system is presented. In some embodiments, the system comprises a first platform configured to be inserted within a body cavity of a patient; a second platform configured to be magnetically coupled to the first platform through a tissue, the second platform comprising a primary magnetic field source that includes multiple magnets; and a control mechanism configured to modulate the strength of the magnetic field between the first platform and the second platform.

In other embodiments, the control mechanism is configured to adjust a physical distance between the primary magnetic field source and the first platform. In other embodiments, the control mechanism may be configured to adjust a position of a throttle member with respect to the primary magnetic field source, and the throttle member is configured to modulate the magnetic field between the first platform and the second platform. In some embodiments, the primary magnetic field source may comprise a first magnet and a second magnet. In other embodiments, the primary magnetic field source may comprise a spacer disposed between the first magnet and the second magnet to create a gap between the first magnet and the second magnet. In some embodiments, the control mechanism is configured to adjust the gap between the first magnet and the second magnet. In other embodiments, the primary magnetic field source may comprise a third magnet disposed between the first magnet and the second magnet, and the third magnet may comprise an electromagnet.

A system is presented. In some embodiments, the system comprises a first platform configured to be inserted within a body cavity of a patient; a second platform configured to be magnetically coupled to the first platform through a tissue, the second platform comprising a primary magnetic field source that includes multiple magnets; and a control mechanism configured to modulate the strength of the magnetic field between the first platform and the second platform. In some embodiments, the control mechanism is configured to adjust a polarity orientation of at least one magnet may comprise the primary magnetic field source. In other embodiments, the primary magnetic field source may comprise an electromagnet. In other embodiments, the control mechanism may comprise a current source coupled to the electromagnet. In some embodiments, the control mechanism may comprise a control circuit for adjusting a level of a current provided to the electromagnet by the current source.

In some embodiments, the control mechanism may comprise a magnetic field modifier configured to interfere with an electric field generated by the primary magnetic field source. In other embodiments, the control mechanism may comprise an adjustment mechanism coupled to the magnetic field modifier, the adjustment mechanism configured to adjust a position of the magnetic field modifier. In some embodiments, the second platform includes a housing in which the primary magnetic field source is positioned, the housing includes an adjustment slot, and the control mechanism comprises an arm coupled to the primary magnetic field source and extending through the adjustment slot such that the arm can be manipulated from outside the housing. In other embodiments, the second platform includes a housing in which the primary magnetic field source is positioned, the housing having a top and a threaded opening in the top, and the control mechanism comprises an arm coupled to the primary magnetic field source and extending through the threaded opening such that the arm can be manipulated from outside the housing.

A system is presented. In some embodiments, the system may comprise a first platform configured to be inserted within a body cavity of a patient; a second platform configured to be magnetically coupled to the first platform through a tissue, the second platform comprising a primary magnetic field source that includes multiple magnets; a feedback device configured to generate a feedback signal indicative of a value associated with the primary magnetic field source; and a control mechanism coupled to the feedback device and configured to modulate the strength of a magnetic field between the first platform and the second platform in response to the feedback signal. In other embodiments, the feedback device is configured to generate an electrical signal. In some embodiments, the feedback device is configured to generate an optical signal. In some embodiments, the feedback device is configured to generate a sonic signal. In some embodiments, the feedback device is configured to generate a Radio Frequency (RF) signal. In some embodiments, the feedback signal is provided to a user of the control mechanism. In some embodiments, the feedback signal is received by the control mechanism. In some embodiments, the control mechanism is configured to be manually adjustable. In some embodiments, the control mechanism is configured to automatically modulate the strength of the magnetic field between the first platform and the second platform in response to the feedback signal. In some embodiments, the control mechanism is configured to adjust a physical distance between the magnetic field source and the first platform in response to the feedback signal.

A system is presented. In some embodiments, the system may comprise a first platform configured to be inserted within a body cavity of a patient; a second platform configured to be magnetically coupled to the first platform through a tissue, the second platform comprising a primary magnetic field source that includes multiple magnets; a feedback device configured to generate a feedback signal indicative of a value associated with the primary magnetic field source; and a control mechanism coupled to the feedback device and configured to modulate the strength of a magnetic field between the first platform and the second platform in response to the feedback signal. In other embodiments, the control mechanism is configured to throttle the magnetic field between the first platform and the second platform in response to the feedback signal. In some embodiments, throttling the magnetic field comprises adjusting a position of a throttle member with respect to the magnetic field source, the throttle member configured to modulate the magnetic field between the first platform and the second platform. In other embodiments, the magnetic field source may comprise a first magnet and a second magnet. In some embodiments, the magnetic field source may comprise a spacer disposed between the first magnet and the second magnet to create a gap between the first magnet and the second magnet. In other embodiments, throttling the magnetic field comprises adjusting the gap between the first magnet and the second magnet.

In some embodiments, the magnetic field source may comprise a third magnet disposed between the first magnet and the second magnet. In other embodiments, the third magnet may comprise an electromagnet. In other embodiments, throttling the magnetic field comprises adjusting a polarity orientation of at least one magnet may comprise the magnetic field source. In some embodiments, the magnetic field source may comprise an electromagnet. In some embodiments, the control mechanism may comprise a current source coupled to the electromagnet. In other embodiments, throttling the magnetic field comprises adjusting a level of a current provided to the electromagnet by the current source. In other embodiments, the control mechanism may comprise a magnetic field modifier configured to interfere with an electric field generated by the magnetic field source. In some embodiments, throttling the magnetic field comprises adjusting a position of the magnetic field modifier.

A system is presented. In some embodiments, the system may comprise a first platform configured to be inserted within a body cavity of a patient; a second platform configured to be magnetically coupled to the first platform through a tissue, the second platform comprising a primary magnetic field source that includes multiple magnets; a feedback device configured to generate a feedback signal indicative of a value associated with the primary magnetic field source; and a control mechanism coupled to the feedback device and configured to modulate the strength of a magnetic field between the first platform and the second platform in response to the feedback signal. In some embodiments, the second platform includes a housing in which the primary magnetic field source is positioned, the housing including an adjustment slot, and the control mechanism comprises an arm coupled to the primary magnetic field source and extending through the adjustment slot such that the arm can be manipulated from outside the housing. In other embodiments, the second platform includes a housing in which the primary magnetic field source is positioned, the housing having a top and a threaded opening in the top, and the control mechanism comprises an arm coupled to the primary magnetic field source and extending through the threaded opening such that the arm can be manipulated from outside the housing.

A system is presented. In some embodiments, the system may comprise a first platform configured to be inserted within a body cavity of a patient; a second platform configured to be placed outside the body cavity and magnetically coupled to the first platform through a tissue, the second platform having a bottom side and a primary magnetic field source that has a coupling end and is configured to move relative to the bottom side; a feedback device may comprise a first sensor, the feedback device configured to generate a feedback signal indicative of a value associated with the primary magnetic field source. In some embodiments, the first sensor is configured to measure the force exerted on the first platform by the primary magnetic field source. In other embodiments, the system is further configured to compare the measured force value to a set-point force value. In some embodiments, the coupling end of the primary magnetic field source is configured to be moved toward the bottom side of the second platform if the measured force value is less than the set-point force value. In other embodiments, the coupling end of the primary magnetic field source is configured to be moved away from the bottom side of the second platform if the measured force value is greater than the set-point force value.

A system is presented. In some embodiments, the system may comprise a first platform configured to be inserted within a body cavity of a patient; a second platform configured to be placed outside the body cavity and magnetically coupled to the first platform through a tissue, the second platform having a bottom side and a primary magnetic field source that has a coupling end and is configured to move relative to the bottom side; a feedback device may comprise a first sensor, the feedback device configured to generate a feedback signal indicative of a value associated with the primary magnetic field source. In some embodiments, the first sensor is configured to measure the thickness of the tissue. In other embodiments, the coupling end of the primary magnetic field source is configured to be moved relative to the bottom side of the second platform based on the thickness of the tissue.

In other embodiments, the system further comprises a second sensor configured to measure the value of the force exerted on the first platform by the primary magnetic field source, where the coupling end of the primary magnetic field source is configured to be moved relative to the bottom side of the second platform to achieve a desired measured force value. In some embodiments, the first platform is further configured to have a top side and the first sensor is configured to measure the distance between the top side of the first platform and the bottom side of the second platform. In some embodiments, the first platform supports the first sensor. In other embodiments, the first sensor comprises at least a pair of electrodes disposed on the first platform. In some embodiments, the electrodes are configured to contact the tissue only if the magnetic force value exerted on the first platform exceeds a set-point force value.

A method is presented. In some embodiments, the method may comprise obtaining a system comprising a first platform configured to be inserted within a body cavity of a patient, a second platform configured to be positioned outside the patient and magnetically coupled to the first platform through a tissue, the second platform comprising a primary magnetic field source that includes multiple magnets, and a control mechanism configured to modulate the strength of the magnetic field between the first platform and the second platform; inserting the first platform into a body cavity of the patient; and positioning the second platform outside the body cavity of the patient such that the second platform is magnetically coupled to the first platform through a tissue. In other embodiments, the method further comprises inserting a needle into the tissue until the needle contacts the first platform; and measuring the distance the needle penetrated the tissue.

In some embodiments, the system comprises a sensor configured to measure the thickness of the tissue, and the method further comprises measuring the thickness of the tissue, and modulating the strength of the magnetic field with the control mechanism. In other embodiments the thickness of the tissue is measured indirectly. In some embodiments, the thickness of the tissue is measured indirectly using ultrasound. In some embodiments, the thickness of the tissue is measured indirectly using sonar. In some embodiments, the thickness of the tissue is measured indirectly using sound waves. In some embodiments, the thickness of the tissue is measured indirectly using light. In other embodiments, the system comprises a sensor configured to measure the value of the magnetic force between the first platform and the second platform, and the method comprises measuring the value of the magnetic force between the first platform and the second platform, and modulating the strength of the magnetic field based on the measured force.

A method is presented. In some embodiments, the method may comprise obtaining a system comprising a first platform configured to be inserted within a body cavity of a patient, a second platform configured to be positioned outside the patient and magnetically coupled to the first platform through a tissue, the second platform comprising a primary magnetic field source that includes multiple magnets, and a control mechanism configured to modulate the strength of the magnetic field between the first platform and the second platform; inserting the first platform into a body cavity of the patient; and positioning the second platform outside the body cavity of the patient such that the second platform is magnetically coupled to the first platform through a tissue. In some embodiments, modulating the strength comprises modulating the strength of the magnetic field until the measured force is within a tolerance of a set-point force value. In other embodiments the set-point value is selected by a user. In other embodiments, the tolerance is selected by a user. In some embodiments, comparing is performed by a computer processor. In some embodiments, the tolerance is +/−10% of the set-point value. In other embodiments, the tolerance is +/−5% of the set-point value. In other embodiments, the tolerance is +/−1% of the set-point value. In other embodiments, the tolerance is +/−0.1% of the set-point value. In other embodiments, the tolerance is +/−0.01% of the set-point value.

A method is presented. In some embodiments, the method may comprise obtaining a system comprising a first platform configured to be inserted into a body cavity of a patient and a second platform configured to be positioned outside the patient and magnetically coupled to the first platform through a tissue, the second platform comprising a bottom side and a magnetic field source comprising a coupling end; where the coupling end of the magnetic field source is configured to be moved relative to the bottom side of the second platform; inserting the first platform into the body cavity of the patient; positioning the second platform outside the body cavity of the patient such that the first platform is magnetically coupled to the second platform through a tissue. In some embodiments, the method comprises measuring the value of the force exerted on the first platform by the primary magnetic field source and modulating the strength of the magnetic field with the control mechanism. In some embodiments, comparing is performed by a computer processor. In some embodiments, the tolerance is +/−10% of the set-point value. In other embodiments, the tolerance is +/−5% of the set-point value. In other embodiments, the tolerance is +/−1% of the set-point value. In other embodiments, the tolerance is +/−0.1% of the set-point value. In other embodiments, the tolerance is +/−0.01% of the set-point value.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 16A-16E illustrate embodiments of a configuration of magnets configured to modulate the strength of the primary magnetic field.

FIGS. 33A-33B illustrate embodiments of a configuration of magnets configured to modulate the strength of the primary magnetic field.

FIG. 33C illustrates a heat map showing the strength of the primary magnetic field.

FIGS. 34A-34B illustrate embodiments of a configuration of magnets configured to modulate the strength of the primary magnetic field.

FIG. 34C illustrates a heat map showing the strength of the primary magnetic field.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The term "substantially" is defined as being largely but not necessarily wholly what is specified, as understood by a person of ordinary skill in the art. For example, in any of the present embodiments, the term "substantially" may be substituted with "within [a percentage] of" what is specified, where the percentage includes any of 5, 10, and/or 15 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, medical device, or apparatus that "comprises," "has," "includes" or "contains" one or more elements possesses those one or more elements, but is not limited to possessing only those one or more elements. Likewise, an element of a system, medical device, or apparatus that "comprises," "has," "includes" or "contains" one or more features possesses those one or more features, but is not limited to possessing only those one or more features. For example, a medical device that comprises a platform and a magnetically-attractive material includes the specified features but is not limited to having only those features. Such a medical device could also include, for example, an arm coupled to the platform.

Further, a device or structure that is configured in a certain way is configured in at least that way, but it can also be configured in other ways than those specifically described.

Figure 1:
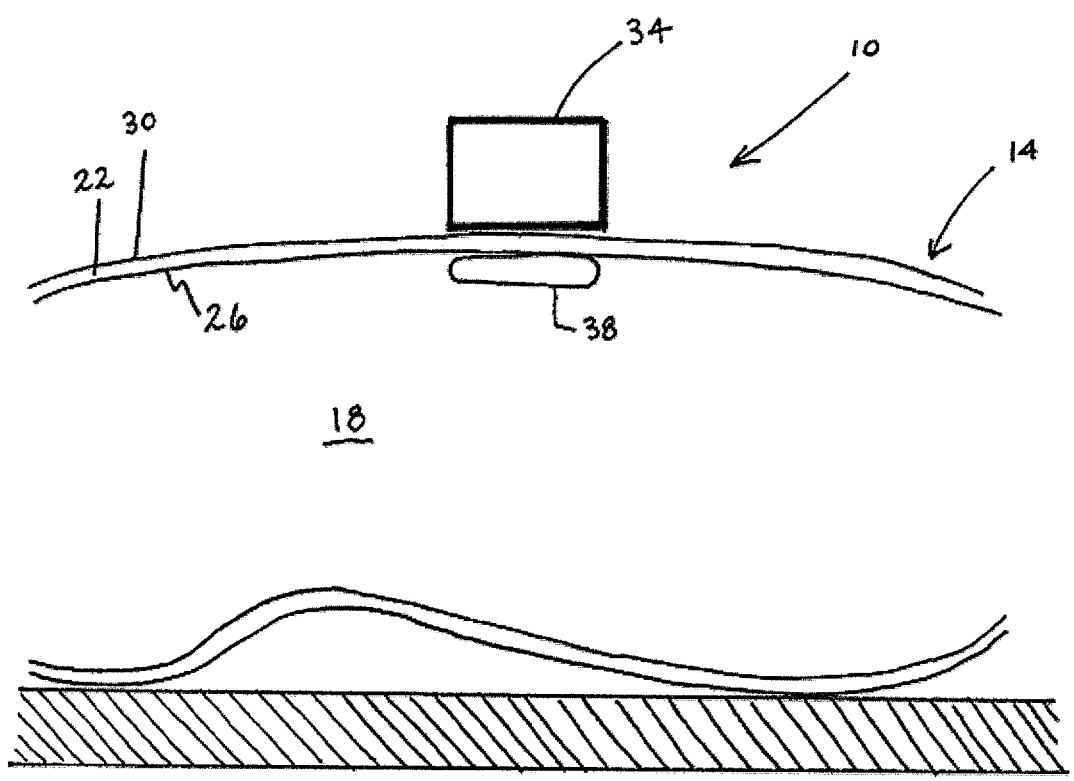
FIG. 1 is a schematic representation of an apparatus magnetically coupled to a surgical device through a tissue.

Referring now to the drawings, shown in FIG. 1 and indicated by reference numeral 10 is one embodiment of a system for medical procedures that can be used with the present invention. System 10 is shown in conjunction with a patient 14, and more particularly in FIG. 1 is shown relative to a longitudinal cross-sectional view of the ventral cavity 18 of a human patient 14. For brevity, cavity 18 is shown in simplified conceptual form without organs and the like. Cavity 18 is at least partially defined by wall 22, such as the abdominal wall, that includes an interior surface 26 and an exterior surface 30. The exterior surface 30 of wall 22 can also be an exterior surface 30 of the patient 14. Although patient 14 is shown as human in FIG. 1, various embodiments of the present invention (including the version of system 10 shown in FIG. 1) can also be used with other animals, such as in veterinary medical procedures.

Further, although system 10 is depicted relative to ventral cavity 18, system 10 and various other embodiments of the present invention can be utilized in other body cavities of a patient, human or animal, such as, for example, the thoracic cavity, the abdominopelvic cavity, the abdominal cavity, the pelvic cavity, and other cavities (e.g., lumens of organs such as the stomach, colon, or bladder of a patient). In some embodiments of the present methods, and when using embodiments of the present devices and systems, a pneumoperitoneum may be created in the cavity of interest to yield a relatively-open space within the cavity.

As shown in FIG. 1, system 10 comprises an apparatus 34 and a medical device 38; the apparatus is configured to magnetically position device 38 within body cavity 18 of patient 14. In some embodiments, apparatus 34 can be described as an exterior apparatus and device 38 as an interior device due the locations of their intended uses relative to patients. In some embodiments, device 38 can include and/or be referred to as a platform (e.g., an internal platform). Apparatus 34 may also be described as an external unit and/or a platform (e.g., an external platform). As shown, apparatus 34 can be positioned outside the cavity 18 near, adjacent to, and/or in contact with the exterior surface 30 of the patent 14. Device 38 is positionable (can be positioned), and is shown positioned, within the cavity 18 of the patient 14 and near, adjacent to, and/or in contact with the interior surface 26 of wall 22. Device 38 can be inserted or introduced into the cavity 18 in any suitable fashion. For example, the device 18 can be inserted into the cavity through a puncture (not shown) in wall 22, through a tube or trocar (not shown) extending into the cavity 18 through a puncture or natural orifice (not shown), or may be inserted into another portion of the patient 14 and moved into the cavity 18 with apparatus 34, such as by the methods described in this disclosure. If the cavity 18 is pressurized, device 38 can be inserted or introduced into the cavity 18 before or after the cavity 18 is pressurized. Additionally, some embodiments of system 10 include a version of device 38 that has a tether (not shown) coupled to and extending away from device 38.

As is discussed in more detail below, apparatus 34 and device 38 can be configured to be magnetically couplable to one another such that device 38 can be positioned or moved within the cavity 18 by positioning or moving apparatus 34 outside the cavity 18. "Magnetically couplable" means capable of magnetically interacting so as to achieve a physical result without a direct physical connection. Examples of physical results are causing device 38 to move within the cavity 18 by moving apparatus 34 outside the cavity 18, and causing device 38 to remain in a position within the cavity 18 or in contact with the interior surface 26 of wall 22 by holding apparatus 34 in a corresponding position outside the cavity 18 or in contact with the exterior surface 30 of wall 22. Magnetic coupling can be achieved by configuring apparatus 34 and device 38 to cause a sufficient magnetic attractive force between them.

For example, apparatus 34 can comprise one or more magnets (e.g., permanent magnets, electromagnets, or the like) and device 38 can comprise a ferromagnetic material. In some embodiments, apparatus 34 can comprise one or more magnets, and device 38 can comprise a ferromagnetic material, such that apparatus 34 attracts device 38 and device 38 is attracted to apparatus 34. In other embodiments, both apparatus 34 and device 38 can comprise one or more magnets such that apparatus 34 and device 38 attract each other. As discussed in more detail below, apparatus 34, device 38, or both may comprise a sensing mechanism to measure the value of the magnetic force apparatus 34 exerts on device 38 or vice versa. Apparatus 34, device 38, or both may be further configured to modulate the strength of the magnetic field between apparatus 34 and device 38.

The configuration of apparatus 34 and device 38 to cause a sufficient magnetic attractive force between them can be a configuration that results in a magnetic attractive force that is large or strong enough to compensate for a variety of other factors (such as the thickness of any tissue between them) or forces that may impede a desired physical result or desired function. For example, when apparatus 34 and device 38 are magnetically coupled as shown, with each contacting a respective surface 26 or 30 of wall 22, the magnetic force between them can compress wall 22 to some degree such that wall 22 exerts a spring or expansive force against apparatus 34 and device 38, and such that any movement of apparatus 34 and device 38 requires an adjacent portion of wall 22 to be similarly compressed. Apparatus 34 and device 38 can be configured to overcome such an impeding force to the movement of device 38 with apparatus 34. Another force that the magnetic attractive force between the two may have to overcome is any friction that exists between either and the surface, if any, that it contacts during a procedure (such as apparatus 34 contacting a patient's skin).

In some embodiments, device 38 can be inserted into cavity 18 through an access port having a suitable internal diameter. Such access ports include those created using a conventional laparoscopic trocar, gel ports, those created by incision (e.g., abdominal incision), and natural orifices. Device 38 can be pushed through the access port with any elongated instrument such as, for example, a surgical instrument such as a laparoscopic grasper or a flexible endoscope.

In some embodiments, when device 38 is disposed within cavity 18, device 38 can be magnetically coupled to apparatus 34. This can serve several purposes including, for example, to permit a user to move device 38 within cavity 18 by moving apparatus 34 outside cavity 18. The magnetic coupling between the two can be affected by a number of factors, including the distance between them. For example, the magnetic attractive force between device 38 and apparatus 34 increases as the distance between them decreases. As a result, in some embodiments, the magnetic coupling can be facilitated by temporarily compressing tissue 22 (e.g., the abdominal wall) between them. For example, after device 38 has been inserted into cavity 18, a user (such as a surgeon) can push down on apparatus 34 (and wall 22) and into cavity 18 until apparatus 34 and device 38 magnetically couple.

In FIG. 1, apparatus 34 and device 38 are shown at a coupling distance from one another and magnetically coupled to one another such that device 38 can be moved within the cavity 18 by moving apparatus 34 outside the outside wall 22. The "coupling distance" between two structures (e.g., apparatus 34 and device 38) is defined as a distance between the closest portions of the structures at which the magnetic attractive force between them is great enough to permit them to function as desired for a given application.

The "maximum coupling distance" between two structures (e.g., apparatus 34 and device 38) is defined as the greatest distance between the closest portions of the structures at which the magnetic attractive force between them is great enough to permit them to function as desired for a given application. Factors such as the thickness and composition of the matter (e.g., human tissue) separating them can affect the coupling distance and the maximum coupling distance for a given application. For example, in the embodiment shown in FIG. 1, the maximum coupling distance between apparatus 34 and device 38 is the maximum distance between them at which the magnetic attractive force is still strong enough to overcome the weight of device 38, the force caused by compression of wall 22, the frictional forces caused by contact with wall 22, and any other forces necessary to permit device 38 to be moved within cavity 18 by moving apparatus 34 outside wall 22. In some embodiments, apparatus 34 and device 38 can be configured to be magnetically couplable such that when within a certain coupling distance of one another the magnetic attractive force between them is strong enough to support the weight of device 38 in a fixed position and hold device 38 in contact with the interior surface 26 of wall 22, but not strong enough to permit device 38 to be moved within the cavity 18 by moving apparatus 34 outside wall 22.

In some embodiments, apparatus 34 and device 38 can be configured to have a minimum magnetic attractive force at a certain distance. For example, in some embodiments, apparatus 34 and device 38 can be configured such that at a distance of 50 millimeters between the closest portions of apparatus 34 and device 38, the magnetic attractive force between apparatus 34 and device 38 is at least about: 20 grams, 25 grams, 30 grams, 35 grams, 40 grams, or 45 grams. In some embodiments, apparatus 34 and device 38 can be configured such that at a distance of about 30 millimeters between the closest portions of apparatus 34 and device 38, the magnetic attractive force between them is at least about: 25 grams, 30 grams, 35 grams, 40 grams, 45 grams, 50 grams, 55 grams, 60 grams, 65 grams, 70 grams, 80 grams, 90 grams, 100 grams, 120 grams, 140 grams, 160 grams, 180 grams, or 200 grams. In some embodiments, apparatus 34 and device 38 can be configured such that at a distance of about 15 millimeters between the closest portions of apparatus 34 and device 38, the magnetic attractive force between them is at least about: 200 grams, 250 grams, 300 grams, 350 grams, 400 grams, 45 grams, 500 grams, 550 grams, 600 grams, 650 grams, 700 grams, 800 grams, 900 grams, or 1000 grams. In some embodiments, apparatus 34 and device 38 can be configured such that at a distance of about 10 millimeters between the closest portions of apparatus 34 and device 38, the magnetic attractive force between them is at least about: 2000 grams, 2200 grams, 2400 grams, 2600 grams, 2800 grams, 3000 grams, 3200 grams, 3400 grams, 3600 grams, 3800 grams, or 4000 grams. These distances may be coupling distances or maximum coupling distances for some embodiments.

In some embodiments, apparatus 34 includes two magnetic field sources, where one of the magnetic field sources is a coupling magnetic field source that is relatively larger than the other or has a relatively stronger magnetic field than the other and therefore generates the majority of the magnetic attractive force, and the other of the magnetic field sources is relatively smaller than the other or has a relatively weaker magnetic field than the other and therefore generates a minority of the magnetic attractive force.

Examples of suitable magnets can include: flexible magnets; Ferrite, such as can comprise Barium or Strontium; AlNiCo, such as can comprise Aluminum, Nickel, and Cobalt; SmCo, such as can comprise Samarium and Cobalt and may be referred to as rare-earth magnets; and NdFeB, such as can comprise Neodymium, Iron, and Boron. In some embodiments, it can be desirable to use magnets of a specified grade, for example, grade 40, grade 50, or the like. Such suitable magnets are currently available from a number of suppliers, for example, Magnet Sales & Manufacturing Inc., 11248 Playa Court, Culver City, Calif. 90230 USA; Amazing Magnets, 3943 Irvine Blvd. #92, Irvine, Calif. 92602; and K & J Magnetics Inc., 2110 Ashton Dr. Suite 1A, Jamison, Pa. 18929. In some embodiments, one or more magnetic field sources can comprise ferrous materials (e.g., steel) and/or paramagnetic materials (e.g., aluminum, manganese, platinum).

Figure 2:
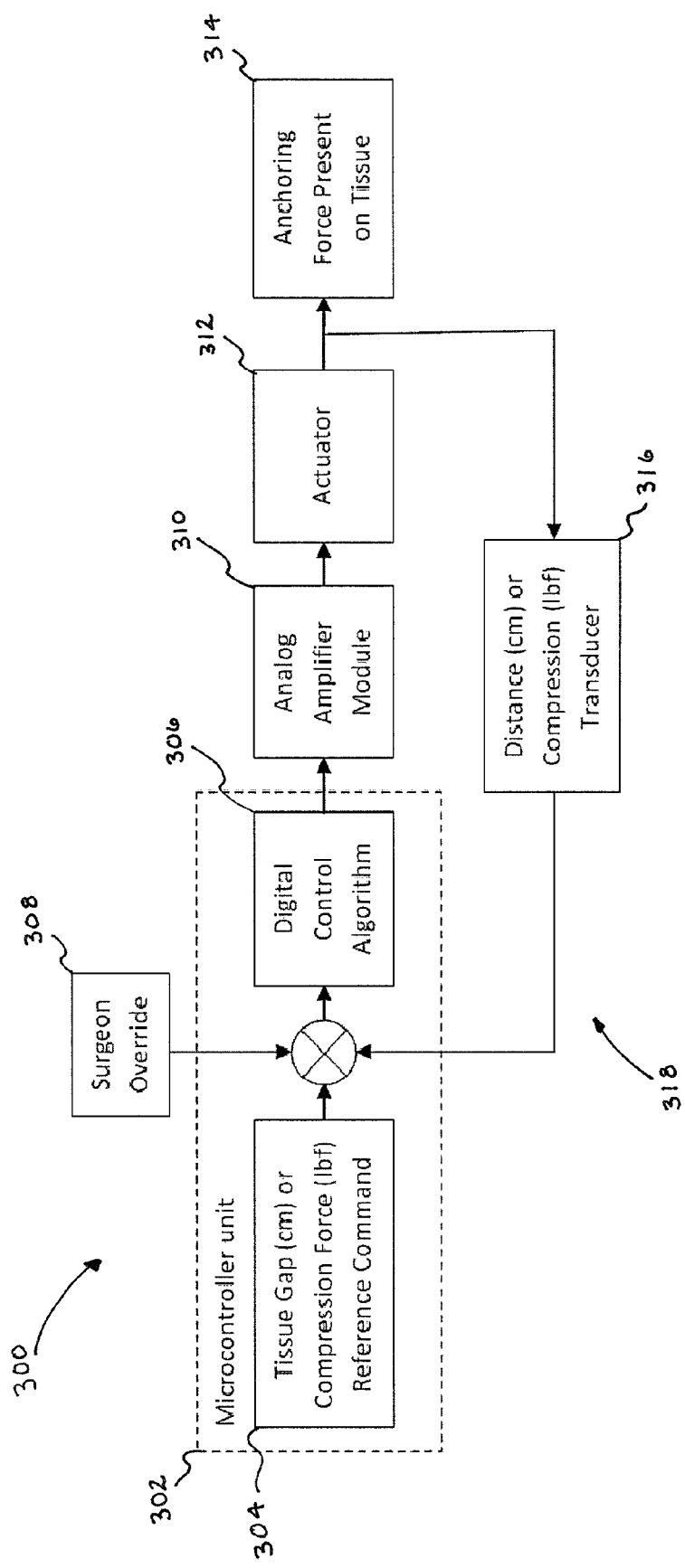
FIG. 2 illustrates an embodiment of a block diagram of a feedback loop control system.

FIG. 2 illustrates a block diagram of one embodiment of a control mechanism 300. In one embodiment, control mechanism 300 includes a feedback signal 318 provided to a microcontroller unit 302. In one particular embodiment, microcontroller unit 302 may include an input port 304 for receiving a measurement of a tissue thickness, a compression force, or a reference signal. In a particular embodiment, input port 304 may receive a signal from a sensor, an ultrasound transducer, an RF receiver, an optical sensor, or the like. Alternatively, microcontroller unit 302 may receive measurement data from a memory device (not shown). The inputs may be passed as parameters to a processing core 306 configured to execute machine readable instructions stored on computer program product (not shown) that when executed cause the processing core to carry out a digital control algorithm.

For example, upon power-up, microcontroller 302 unit may produce a known reference command (set point value, nominal force, or nominal target distance) and compare it with the presently sensed state of the system (e.g., using a feedback signal from a feedback sensor). The difference, or error (output of the summing junction, represented by a circle with a cross) may be converted into a reference voltage and passed on to an analog amplifier module. This reference voltage may be calculated by a digital control algorithm designed to drive the system to the desired state, while correcting for factors such as sensor nonlinearities and offsets.

In one embodiment, a surgeon may override the normal algorithm's output to effect fine adjustments in tissue compression through a surgeon override port 308.

The analog amplifier 310 may directly drive an actuator 312 on device 34, which results in an increase or decrease of tissue compression force. Alternatively, the digital control algorithm 306 may drive a current source (not shown) to produce varying levels of current to an electromagnet 900, such as the electromagnet 900 described below in FIG. 22. One of ordinary skill may recognize additional control devices that may be employed.

The control loop schematic and fundamental operation may be the same for various sensing methods or actuation technology being used, so long as the two are correlated.

In addition to the externally supplied data, control mechanism 300 may include an internal feedback loop. In such an embodiment, a sensor 316 or other device may generate a feedback signal 318 to microcontroller unit 302. Feedback signal 318 may be indicative of a value associated with the primary magnetic field source, such as a coupling force between first platform 38 and second platform 34, thickness of tissue 22, or a distance between first platform 38 and the second platform 34.

Figure 3A:
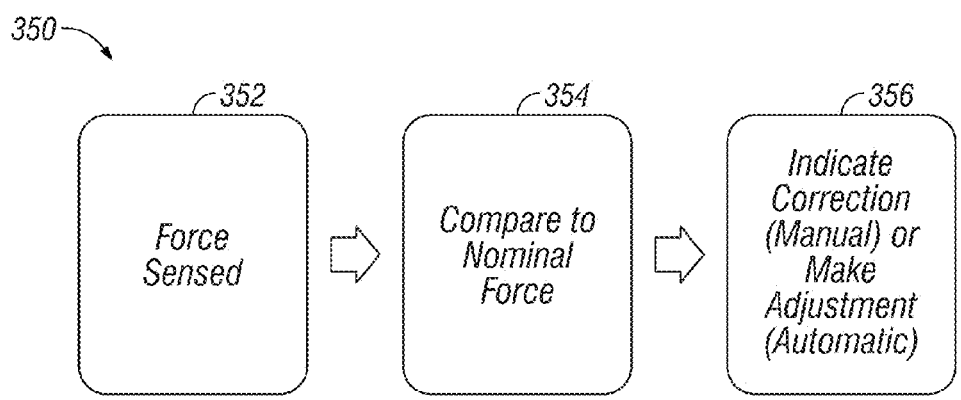
FIGS. 3A-3B are flow chart diagrams illustrating one embodiment of a control algorithm.

FIG. 3A illustrates a simple block diagram illustrating the feedback control of one embodiment of control mechanism 300. In one embodiment, method 350 includes sensing 352 a force—such as a magnetic coupling force or a torque force—generated between first platform 38 and second platform 34. This value may be compared 354 by microcontroller unit 302 to a nominal force, e.g., a predetermined calibration level. Microcontroller unit 302 may then indicate 356 a correction and cause actuator 312 to make an adjustment. Alternatively, the method may include presenting data to a user and receiving a user input used to drive the adjustment.

Figure 3B:
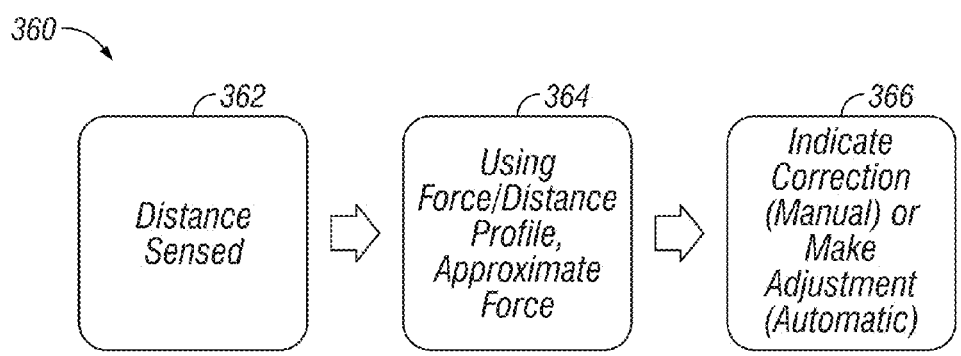

FIG. 3B illustrates an alternative method 360. In one embodiment, method 360 includes sensing 362 or measuring a distance between first platform 38 and second platform 34. For example, the distance may be sensed using an ultrasound transducer. Alternatively, the distance may be deduced from an X-ray scan or other imaging method. Microcontroller unit 302 may then use 364 the force and/or distance profile information to approximate an attraction force between first platform 38 and second platform 34. The microcontroller unit 302 or a user may then indicate 366 a correction or make an adjustment to the magnets using the actuator 312 or other control devices as described above.

Figure 4:
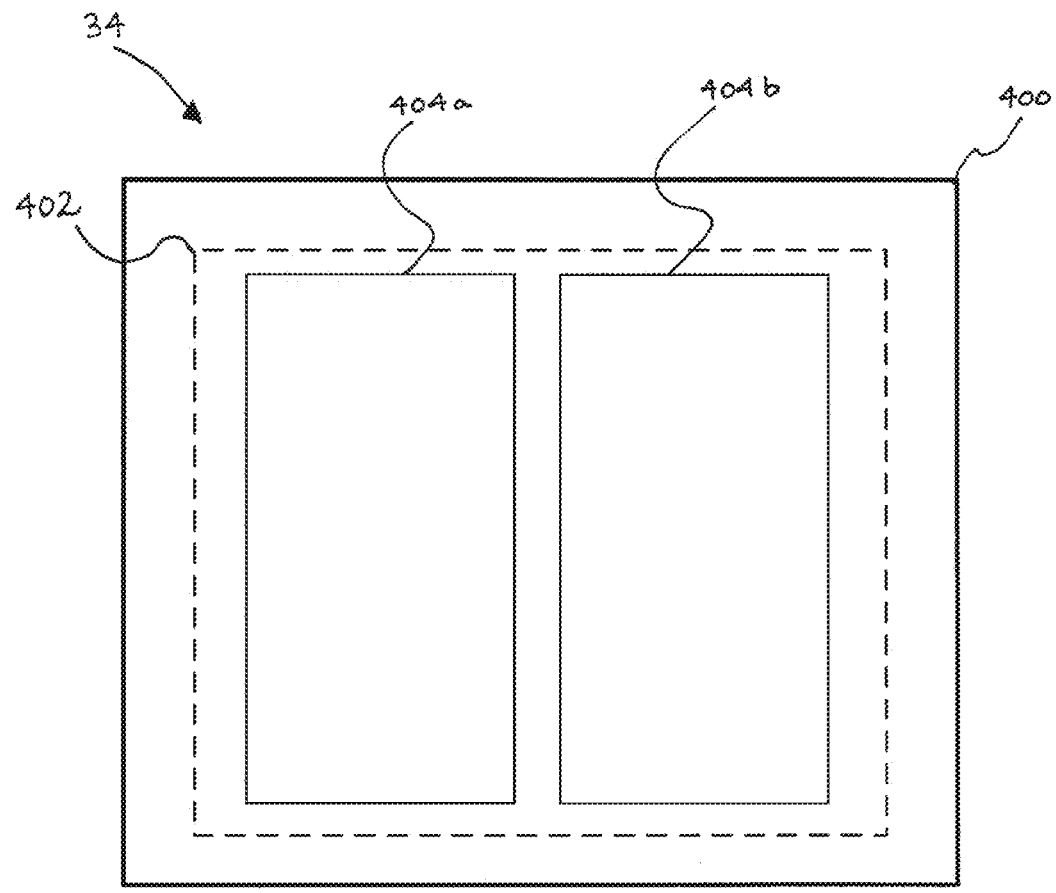
FIG. 4 is a schematic embodiment of an apparatus comprising a primary magnetic field source and a surgical device comprising magnetic members.
Figure 4:
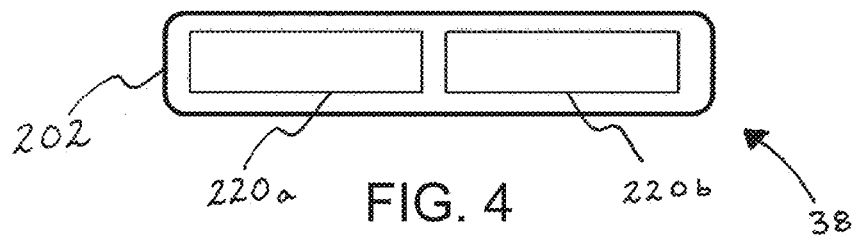

FIG. 4 illustrates one embodiment of a second platform 34. Second platform 34 may also be referred to as an "external unit." In one embodiment, second platform 34 includes a primary magnetic field source 402. For example, the primary magnetic field source may include a magnet assembly. The magnet assembly may include multiple magnets 404a, 404b. Magnets 404a, 404b may be housed in and/or coupled to a housing 400.

FIG. 4 also illustrates one embodiment of a first platform 38. First platform 38 may be referred to as an "internal platform." In one embodiment, first platform 38 also includes multiple magnets 220a, 220b. First platform 38 may additionally include a housing 202 or casing. In a particular embodiment, both first platform 38 and second platform 34 may be sterile. For example, platforms 34, 38 may be stored in sterile packaging which may be removed before use.

In certain embodiments of the invention, one or both of apparatus 34 and device 38 may be provided with one or more sensors to measure the attractive force between apparatus 34 and device 38. Non-limiting examples of sensors that may be used to measure the magnetic force between apparatus 34 and device 38 include: analog or digital force gauges, also known as strain gauges; pressure sensors; transducers; a load cell; a tactile sensor array comprising at least two tactels; piezoresistive sensors; piezoelectric sensors; capacitive sensors; elastoresistive sensors; electrodes; or electrical contacts.

In some embodiments, a signal 318 may be sent to a user from a sensor 316 indicating that the attractive force between apparatus 34 and device 38 should be adjusted. The user may then make the adjustment manually. In other embodiments, a user (e.g. a doctor or nurse) may select a set-point value for the desired attractive force or distance between apparatus 34 and device 38. In certain embodiments, the system is configured to compare the measured value to the set-point value and adjust the attractive force automatically via a feedback loop until the measured value is within an acceptable tolerance of the set-point value. In some embodiments, the tolerance may be +/−10%, +/−5%, +/−1%, +/−0.1%, or +/−0.01% of the set point value. In some embodiments, the set-point value and the measured value may be displayed (e.g., on a digital display or on a computer monitor).

In other embodiments, the system is configured to detect whether apparatus 34 and device 38 are magnetically coupled, and whether or not the magnetic coupling force between them exceeds a desired value. In these embodiments, the detection scheme is binary: apparatus 34 and device 38 are either coupled or not, and the coupling force between them either exceeds the desired coupling force between them or it does not. Specific sensor embodiments are discussed below. In some of the below embodiments, the sensor is housed on device 38. These are non-limiting examples: In other embodiments, the sensor may be housed on apparatus 34. In still other embodiments, both apparatus 34 and device 38 may comprise one or more sensors. In additional embodiments, the sensor may be external to both apparatus 34 and device 38.

In some embodiments, the sensor is electrically coupled to the system (e.g., with wires). The signal representing the measured force value may travel through the wires to a computer, a processor, a comparator chip, or another similar structure capable of comparing the measured force value to the set-point value. In other embodiments, the sensor is wirelessly coupled to the system. As in the wired configurations, the signal representing the measured force value may be transmitted from the sensor to a computer, a processor, a comparator chip.

Figure 5A:
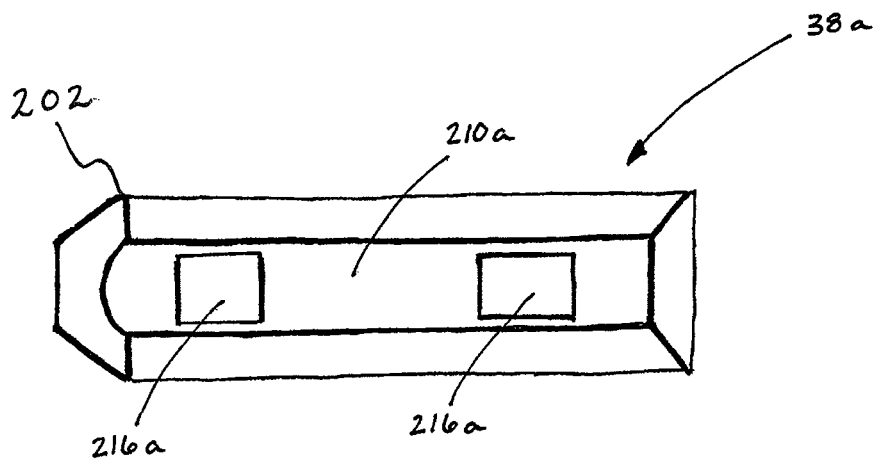
FIGS. 5A-5B illustrate embodiments of a surgical device comprising magnetic members and sensors.
Figure 5B:
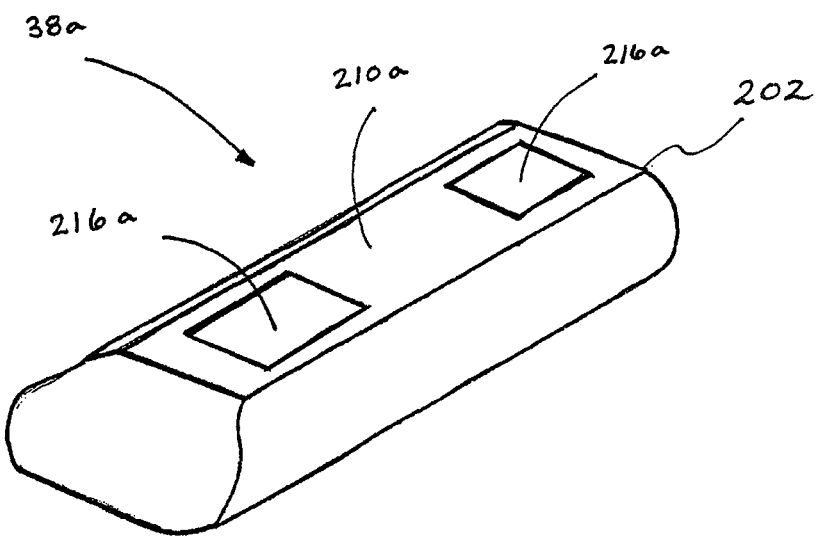

Specific embodiments of device 38 comprising sensors 216 will be discussed presently. FIGS. 5A and 5B show a top view and a perspective view, respectively, of an embodiment 38a of device 38. In this embodiment, sensors 216a are located on top surface 210a. In some embodiments, one sensor may be used. In other embodiments, two or more sensors may be used. Device 38a comprises ferromagnetic material such that device 38a is magnetically couplable to apparatus 34. When device 38a is magnetically coupled to apparatus 34, top surface 210a and sensors 216a of device 38a contact interior surface 26. Interior surface 26 exerts a force on top surface 210a and sensors 216a having a magnitude equal to the magnitude of the magnetic force exerted on device 38a. Sensors 216a are configured to detect the force exerted upon them by interior surface 26. In some embodiments, sensors 216a are configured to measure and display the value of the force exerted upon them by interior surface 26. In some embodiments, sensors 216a are configured to measure the force and compare it to a set-point value.

Figure 6:
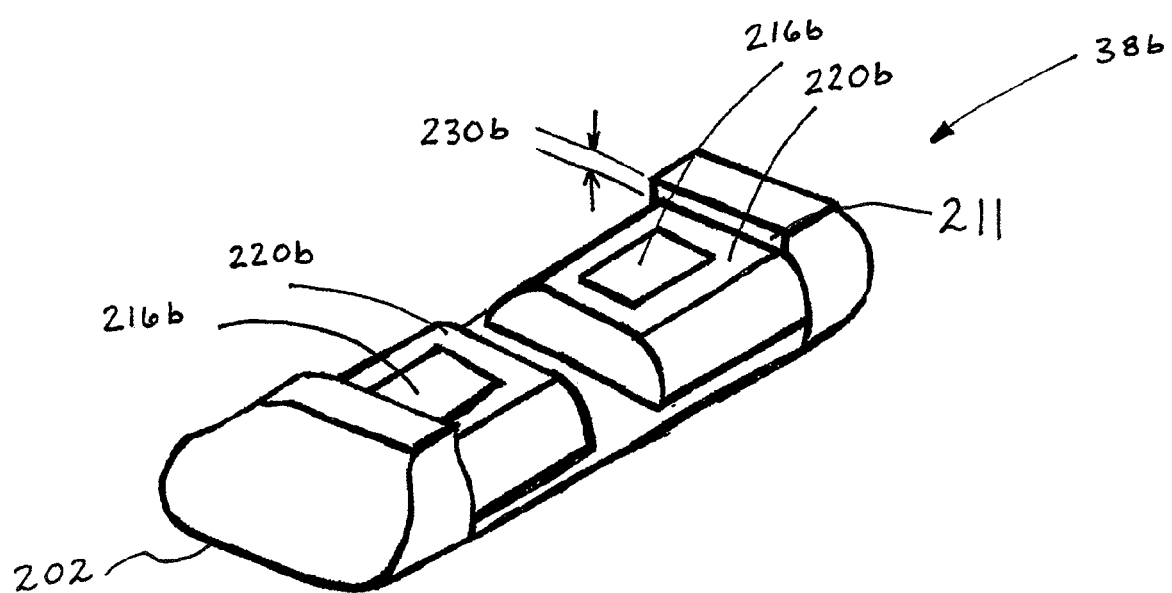
FIG. 6 is an embodiment of a surgical device comprising magnetic members and sensors.

FIG. 6 shows a partially cross-sectional perspective view of embodiment 38b of device 38 is shown. In device 38b, ferromagnetic members 220b are housed within device 38. Sensors 216b are located on top of ferromagnetic members 220b. In some embodiments, ferromagnetic members 220b can comprise Ferrite, such as can comprise Barium or Strontium; AlNiCo, such as can comprise Aluminum, Nickel, and Cobalt; SmCo, such as can comprise Samarium and Cobalt and may be referred to as rare-earth magnets; NdFeB, such as can comprise Neodymium, Iron, and Boron; or ferrous steel. Though device 38b depicts two ferromagnetic members 220b, any number of one or more ferromagnetic members 220b may be used.

When outside the presence of a magnetic field, there is a gap 230b between sensors 216b and housing interior surface 211 allowing ferromagnetic members 220b a slight amount of movement. When device 38b is magnetically coupled to device 34, ferromagnetic members 220b will contact housing interior surface 211. The magnitude of the magnetic coupling force exerted by housing interior surface 211 on sensors 216b is equal to the magnitude of the magnetic coupling force between device 38b and apparatus 34. Sensors 216b are configured to detect the force exerted upon them by housing interior surface 211. In some embodiments, sensors 216b are configured to measure and display the value of the force exerted upon them by housing interior surface 211. In some embodiments, sensors 216b are configured to measure the force and compare it to a set-point value.

Figure 7A:
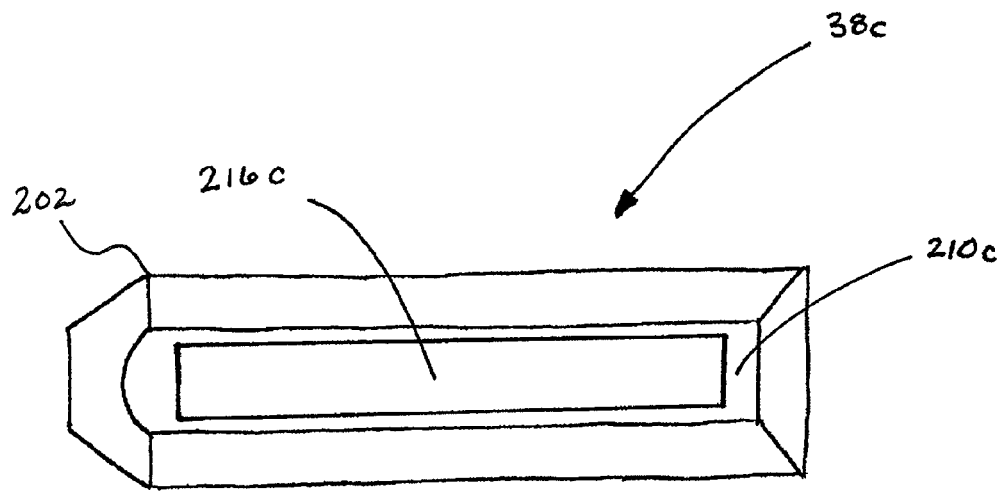
FIGS. 7A-7B are embodiments of a surgical device comprising a sensor.
Figure 7B:
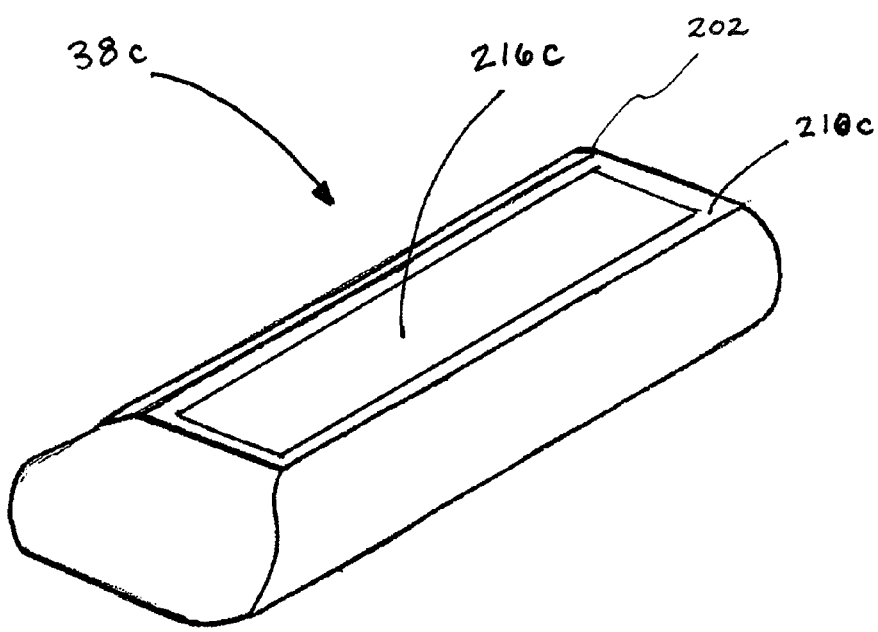

Referring now to FIGS. 7A and 7B, a top view and a perspective view of embodiment 38c of device 38 are shown. In this embodiment, a sensor 216c is located on top surface 210c. Device 38c comprises ferromagnetic material such that device 38c is magnetically couplable to apparatus 34. When device 38c is magnetically coupled to apparatus 34, top surface 210c and sensor 216c of device 38c contact interior surface 26. Interior surface 26 exerts a force on top surface 210c and sensor 216c having a magnitude equal to the magnitude of the magnetic force exerted on device 38c. Sensor 216c is configured to detect the force exerted upon it by interior surface 26. In some embodiments, sensor 216c is configured to measure and display the value of the force exerted upon them by interior surface 26. In some embodiments, sensor 216c is configured to measure the force and compare it to a set-point value.

Figure 8A:
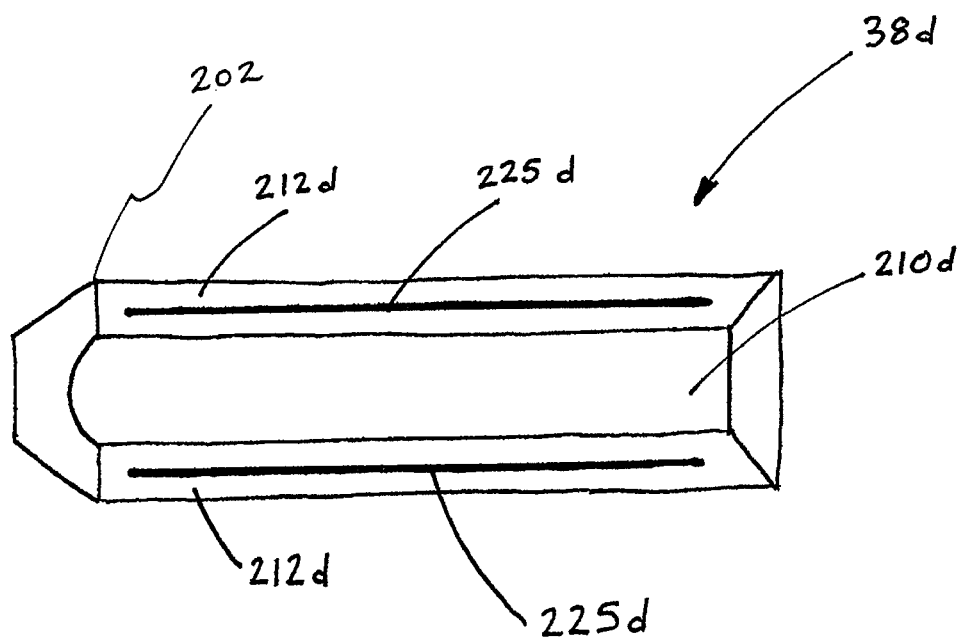
FIGS. 8A-8B are embodiments of a surgical device comprising electrodes.
Figure 8B:
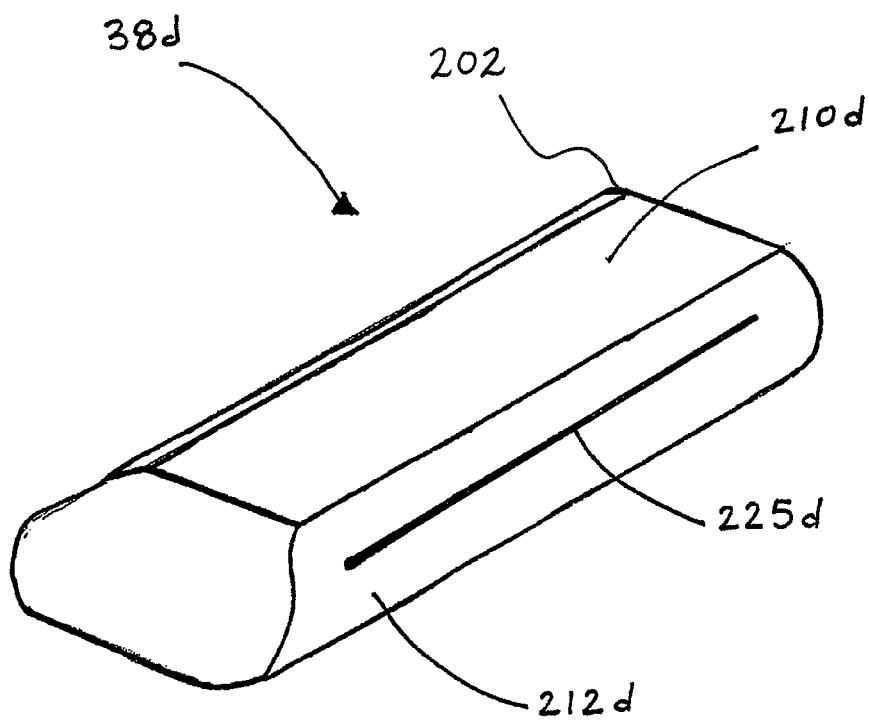

Turning now to FIGS. 8A and 8B, a top view and a perspective view of an embodiment 38d of device 38 are shown. Device 38d comprises a top surface 210d, sides 212d, and electrodes 225d disposed on sides 212d. Device 38d is configured to detect whether the coupling force between device 38d and apparatus 34 exceeds a desired value.

Figure 8C:
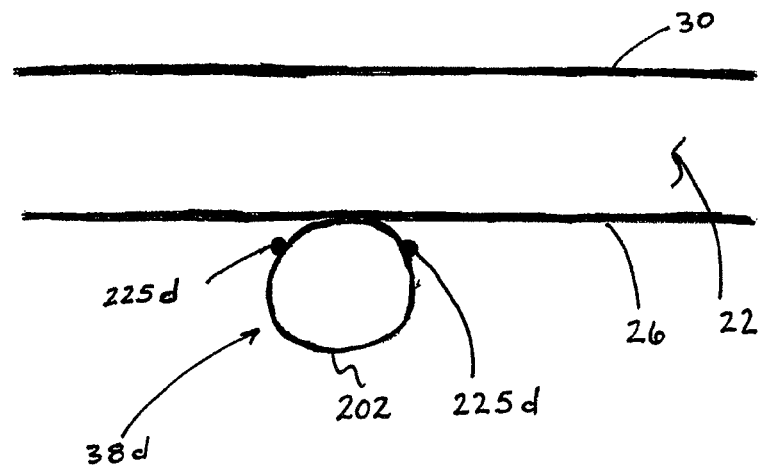
FIG. 8C illustrates surgical device of FIG. 8A-8B subject to an acceptable level of magnetic force.
Figure 8D:
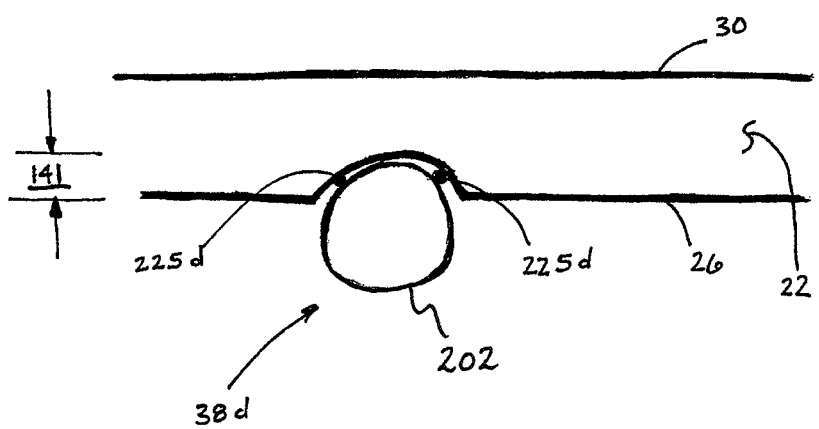
FIG. 8D illustrates surgical device of FIG. 8A-8B subject to an excessive level of magnetic force.

FIGS. 8C and 8D illustrate an end view of device 38d in contact with interior surface 26 of tissue 22 in the presence of a magnetic field. As shown in FIG. 8C, electrodes 225d are disposed on sides 212d such that when the magnetic coupling force exerted on device 38d is below a maximum acceptable value, electrodes 225d do not contact interior surface 22. Tissue 22 may be compressed minimally or not at all. As shown in FIG. 8D, when the magnetic coupling force exerted on device 38d exceeds the maximum acceptable value, tissue 22 is compressed a distance 141 such that electrodes 225d contact interior surface 26. Because tissue is electrically conductive, contact with interior surface 26 completes a circuit between electrodes 225d and generates a signal. In some embodiments, the signal is relayed to a user, who may then manually decrease the magnetic coupling force until electrodes 225d no longer contact interior surface 26. In other embodiments, the adjustment to the magnetic coupling force is made automatically. When electrodes 225d no longer contact interior surface 26, the circuit is broken. In some embodiments, a different signal is sent to the system indicating that the magnetic coupling force has fallen below the maximum acceptable value. In other embodiments, no signal is sent when there is not a completed circuit between electrodes 225d.

Figure 9:
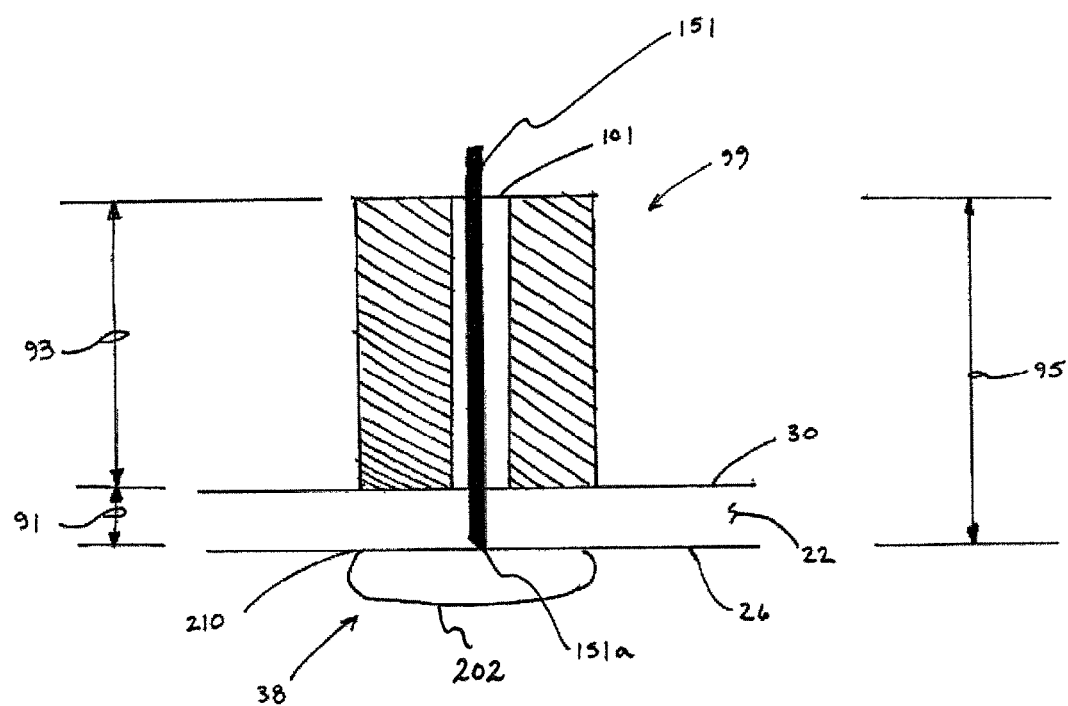
FIG. 9 illustrates a needle and a trocar for measuring the thickness of a tissue.
Figure 10:
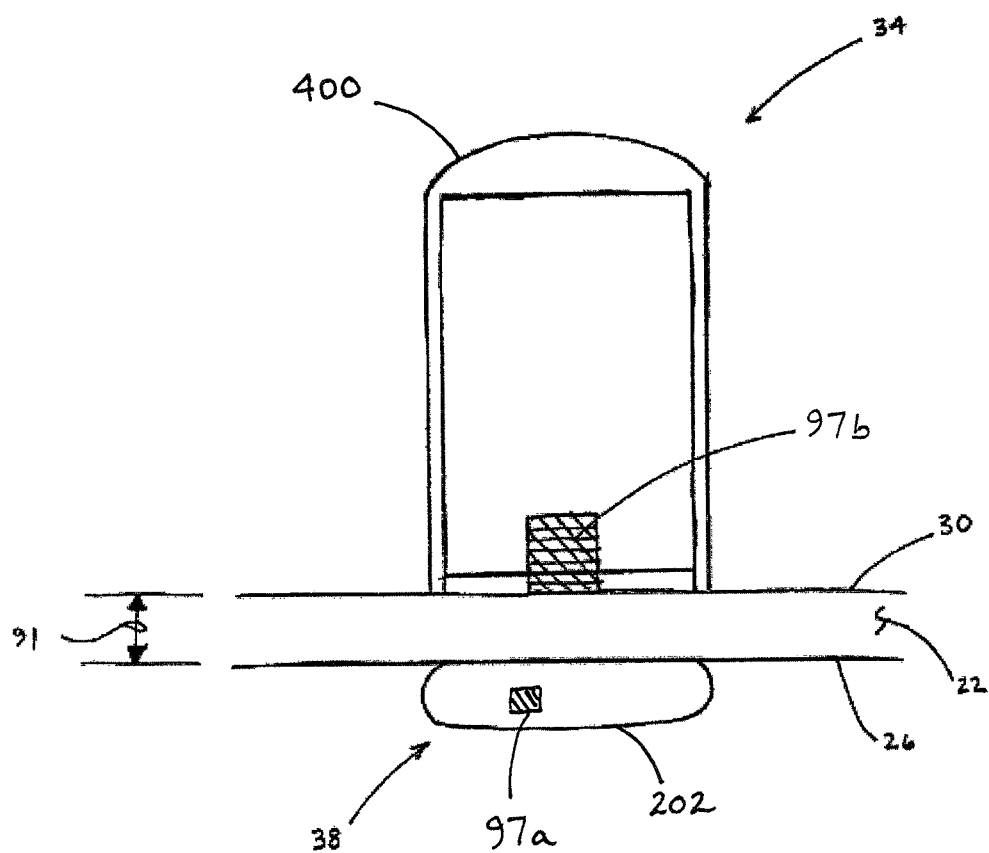
FIG. 10 illustrates an apparatus comprising a sensor integral to the apparatus.
Figure 11:
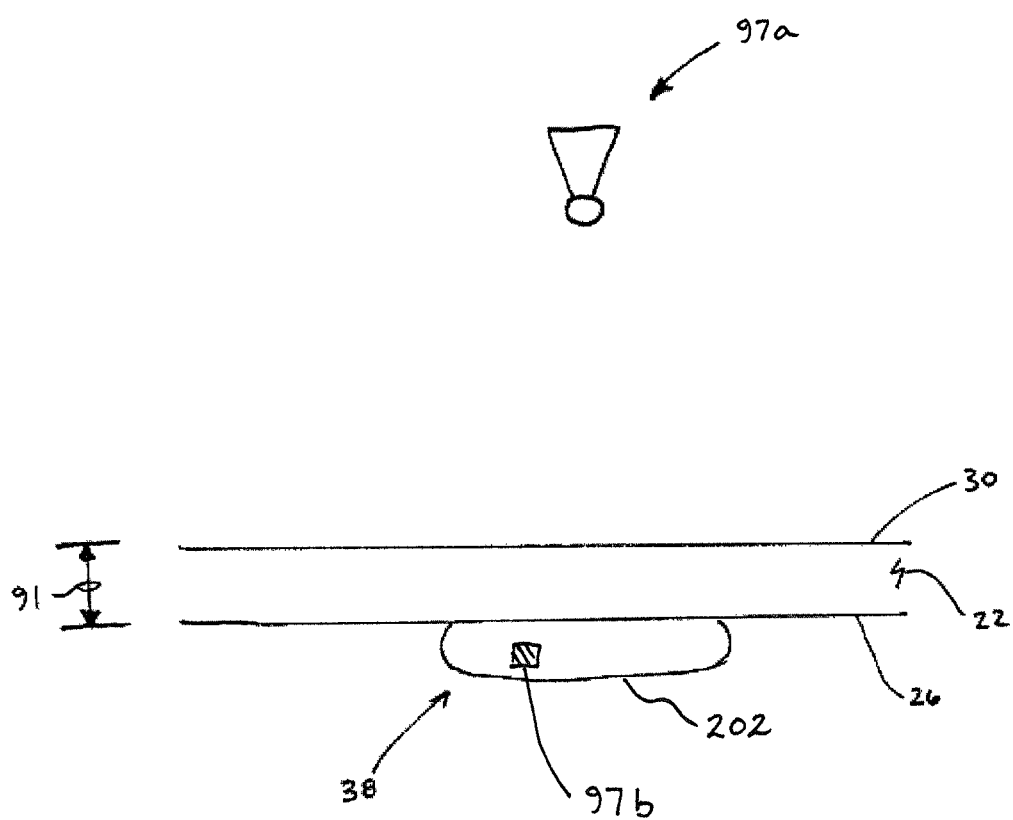
FIG. 11 illustrates a system comprising a sensor external to the apparatus and the surgical device.

FIGS. 9-11 depict different ways of measuring the distance 91 between apparatus 34 and device 38. In certain embodiments, distance 91 between apparatus 34 and device 38 must be known in addition to or instead of the force between apparatus 34 and device 38. When apparatus 34 and device 38 are magnetically coupled, distance 91 is equivalent to the thickness of tissue 22. Ascertaining a value for distance 91 may, for example, aid a user in calibrating the strength of the magnetic field using a known or knowable relation between the magnetic field strength and distance 91.

FIG. 9 shows a cross-sectional view of a trocar 99 with a known height 93. In some embodiments, it is possible to directly measure distance 91 with a needle 151. In such embodiments, trocar 99 is placed on exterior surface 30 of tissue 22 above device 38. For example, exterior surface 30 may be the topmost layer of a patient's skin. Needle 151 can be inserted into port 101 of trocar 99 until the needle tip 151a contacts top surface 210 of device 38 (e.g., achieving a penetration distance 95). In some configurations, needle 151 comprises graduated markings such as millimeters, centimeters, fractions of an inch (not shown). In such embodiments, user may measure penetration distance 95 by reading the graduated marking on the exposed portion of the needle. In other configurations, a user may mark needle 151 to indicate penetration distance 95 and then measure penetration distance 95 (e.g., with a ruler, calipers, or other measuring instrument). Distance 91 between apparatus 34 and device 38 can be calculated by subtracting trocar height 93 from penetration distance 95.

FIG. 10 shows a cross-sectional view of apparatus 34 and device 38 comprising a sensor pair 97a and 97b configured to indirectly measure distance 91 between apparatus 38 and device 34 (equivalent to thickness of tissue 22), where element 97b is located on apparatus 34. FIG. 11 shows an arrangement whereby element 97a is located external to apparatus 34. FIGS. 10 and 11 are considered together here.

In general, a transmitter and a receiver are required to indirectly measure a distance. The transmitter generates a signal, which may comprise light waves, sound waves, radio frequency waves, ultrasound waves, electromagnetic waves, or radiation waves. The signal is sent from the transmitter to the receiver. In some embodiments, the receiver is an active receiver, whereby upon receiving the signal source, the receiver generates its own signal and returns that signal to the transmitter. In other embodiments, the receiver is a passive receiver, and merely reflects the signal generated by the transmitter.

In the embodiments shown, either element of sensor pair 97a and 97b could be the transmitter. The other element would necessarily be the receiver. For example, if element 97a is the transmitter, element 97b is the receiver. In such an embodiment, transmitter 97a generates a signal that is transmitted through the air and tissue 22 until it reaches receiver 97b. In embodiments where element 97b is an active receiver, element 97b receives the signal generated by the transmitter, then generates its own signal that is then sent back to the transmitter (element 97a in this case). In embodiments where element 97b is a passive receiver, element 97b merely reflects the signal generated by element 97a, where it is then received by the transmitter. In some embodiments, distance 91 can be correlated to the amount of time it takes for the signal to travel from transmitter to the receiver and back to the transmitter. In other embodiments, distance 91 can be determined by the vibrations the returned signal creates in the transmitter. In other embodiments, element 97b is the transmitter and element 97a is the receiver.

In some embodiments where element 97a is the transmitter and element 97b is a passive receiver, device 38 itself may be the receiver. In other words, device 38 may be configured to reflect the signal generated by the transmitter, and a separate sensor element is not required.

Some embodiments use sound waves to measure distance 91. In some embodiments, element 97a is an ultrasound source, device 38 is configured to reflect the ultrasonic waves generated by element 97a. In other embodiments, element 97b generates a sonic signal (such as a chirp or a beep), and element 97a is a microphone configured to detect the sonic signal.

Other embodiments use light to measure distance 91. In some embodiments, element 97a is an infrared light source. In other embodiments, element 97a is an ultraviolet light source. Element 97b is configured to reflect the light back to element 97a.

In some embodiments sensor pair 97a and 97b comprise magnetic resistive sensors, magnetic conductive sensors, or magnetic capacitive sensors. In still other embodiments, the thickness of tissue 22 could be measured using an MRI or a CT scanner ahead of surgery.

FIGS. 12A-14D depict embodiments of a housing 400 comprising a control mechanism 300 configured to move primary magnetic field source 402 relative to device 38 to modulate the magnetic force between apparatus 34 and device 38. In this embodiment, the control mechanism may comprise an arm 502 and one of a slot 506, a rack 504, or an opening 411. As shown in FIGS. 12A-14D, in some embodiments, apparatus 34 has a primary magnetic field source 402 configured to move relative to the bottom side of apparatus 34 and top side of tissue 22. Moving primary magnetic field source 402 modulates the magnetic field by changing distance 407 between primary magnetic field source 402 and device 38. Primary magnetic field source 402 is configured to be magnetically coupled to device 38 through tissue 22.

As discussed above, a sensor is configured to measure a value associated with primary magnetic field source 402. A feedback device is configured to generate a feedback signal indicative of a value associated with primary magnetic field source. In some embodiments, that value may be the magnetic force between apparatus 34 and device 38. In other embodiments, that value may be the thickness of tissue 22. In other embodiments, that value may be distance 407 between primary magnetic field source 402 and device 38.

As discussed below, system 10 may comprise a control mechanism 300 to modulate the strength of the magnetic field between apparatus 34 and device 38. In some embodiments, the strength of the magnetic field may be modulated by moving primary magnetic field source 402 closer to or further from device 38. In some embodiments, apparatus 34 includes a housing 400 with a bottom side. In some embodiments, apparatus 34 is configured such that primary magnetic field source 402 is configured to be moved relative to bottom side of apparatus 34. In such embodiments, apparatus 34 may remain in contact with the outer surface (e.g., the skin, tissue 22) of patient 14 while primary magnetic field source moves within apparatus 34.

Figure 12A:
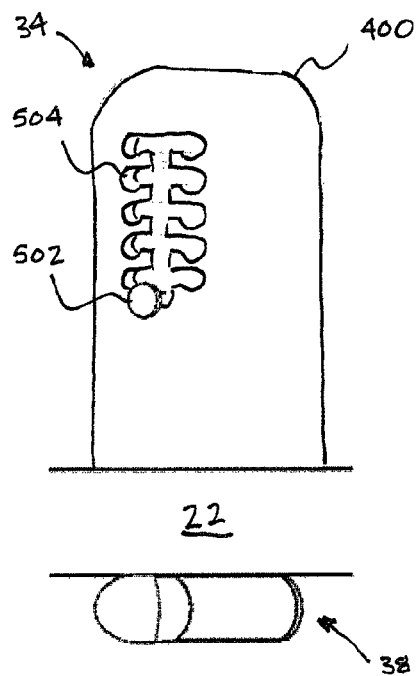
FIGS. 12A-12D illustrate embodiments of an apparatus configured to change the distance between a primary magnetic field source and a surgical device.
Figure 12B:
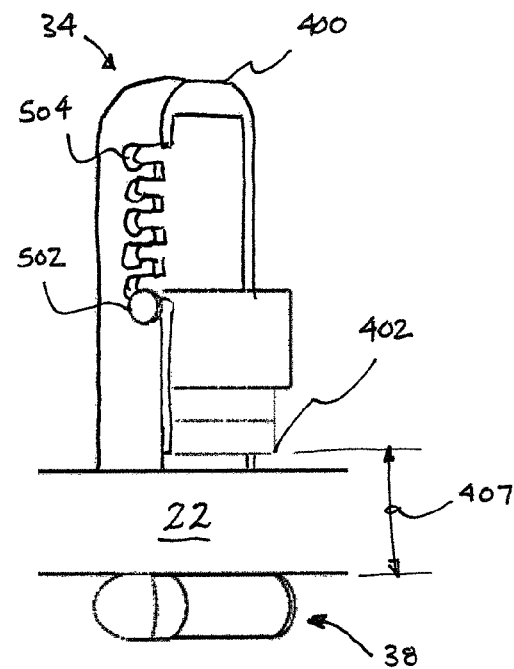
Figure 12C:
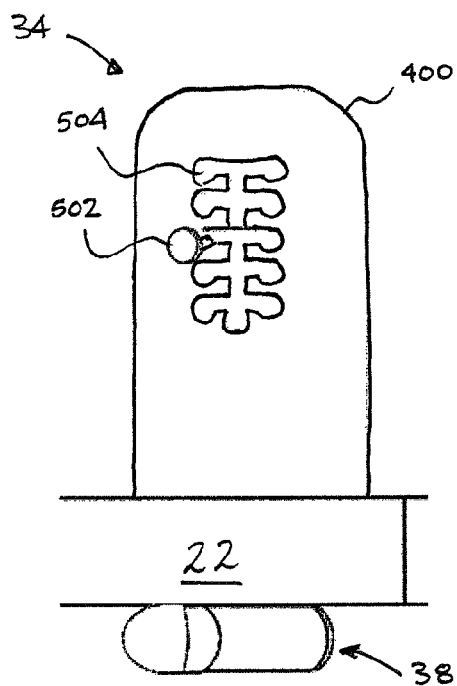
Figure 12D:
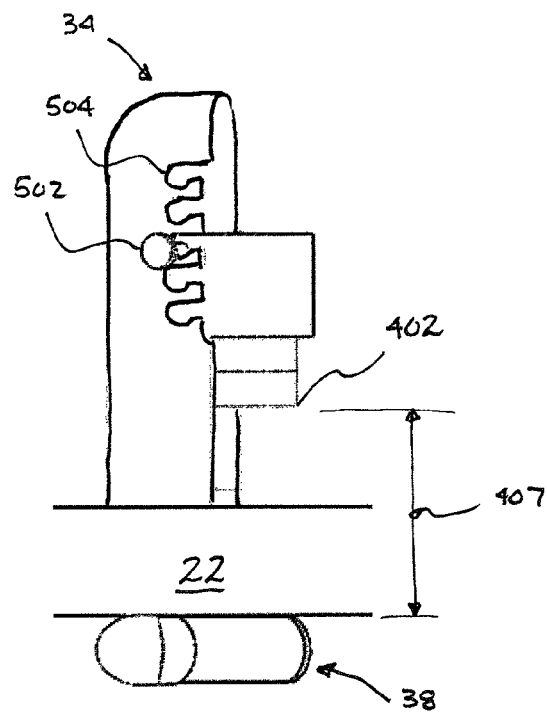

As shown in FIGS. 12A-12D, in some embodiments, housing 400 of apparatus 34 includes control mechanism that comprises an adjustment rack 504 and arm 502. FIGS. 12A and 12B depict a side view and a partially cutaway view, respectively, of one embodiment of apparatus 34 with primary magnetic field source 402 adjusted such that distance 407 is at a minimum, and such that magnetic force between device 38 and apparatus 34 is at a maximum. FIGS. 12C and 12D depict a side view and a partially cutaway view of one embodiment of apparatus 34 with primary magnetic field source 402 adjusted such that distance 407 is greater than a minimum, and such that magnetic force between device 38 and apparatus 34 is less than a maximum. In some embodiments, arm 502 is coupled to primary magnetic field source 402 such that arm 502 extends through adjustment rack 504 and can be manipulated from outside housing 400.

By manipulating arm 502, distance 407 between primary magnetic field source 402 and device 38 may be modified, which modifies the magnetic field. Primary magnetic field source 402 may be moved closer to or further away from device 38 within housing 400, depending on the desired magnetic field strength, but in the embodiment shown, housing 400 is substantially fixed (will not move) relative to device 38. In some embodiments, arm 502 comprises a threaded bolt such that the bolt may be loosened to move primary magnetic field source 402, and the bolt may be tightened to fix primary magnetic field source 402 at a desired distance 407 from device 38.

In other embodiments, a similar configuration as shown in FIGS. 12A-12D may be used, except in these embodiments, control mechanism can be automated through the feedback loop as described above regarding FIGS. 2-3B. That is, control mechanism is configured to receive a signal corresponding to a property of the magnetic field and adjust the distance 407 from primary magnetic field source 402 to device 38 according to that signal. For instance, if the value of the magnetic force exceeds a set-point value by more than an acceptable tolerance, control mechanism will move primary magnetic field source 402 further away device 38. In other words, control mechanism will move primary magnetic field source 402 within housing 400 further away from device 38, but housing 400 will not move relative to device 38. If the value of the magnetic force is less than set-point value by more than a tolerance, control mechanism will move coupling end closer to bottom side.

Figure 13A:
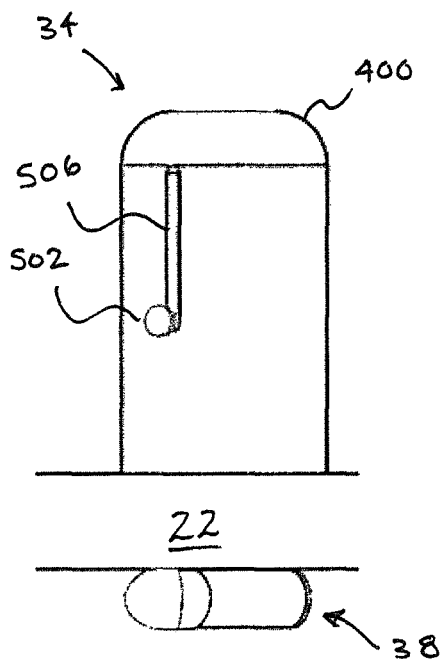
FIGS. 13A-13D illustrate embodiments of an apparatus configured to change the distance between a primary magnetic field source and a surgical device.
Figure 13B:
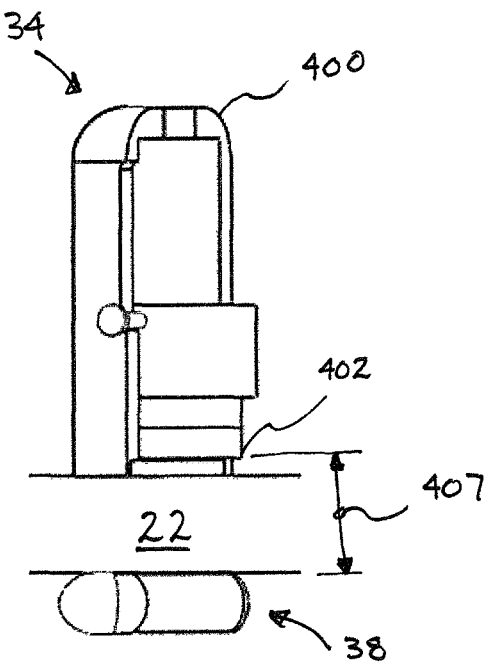
Figure 13C:
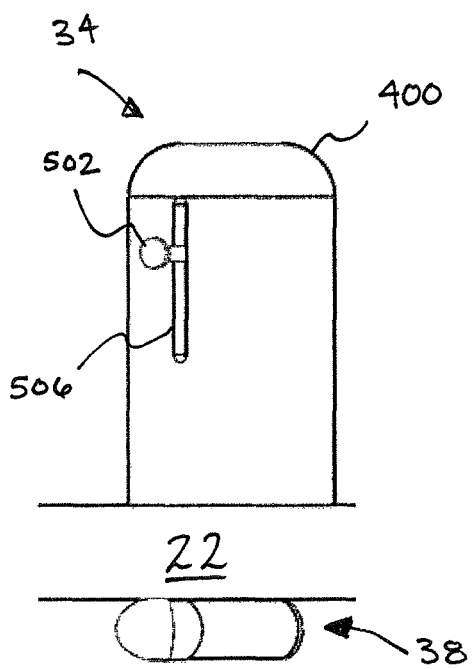
Figure 13D:
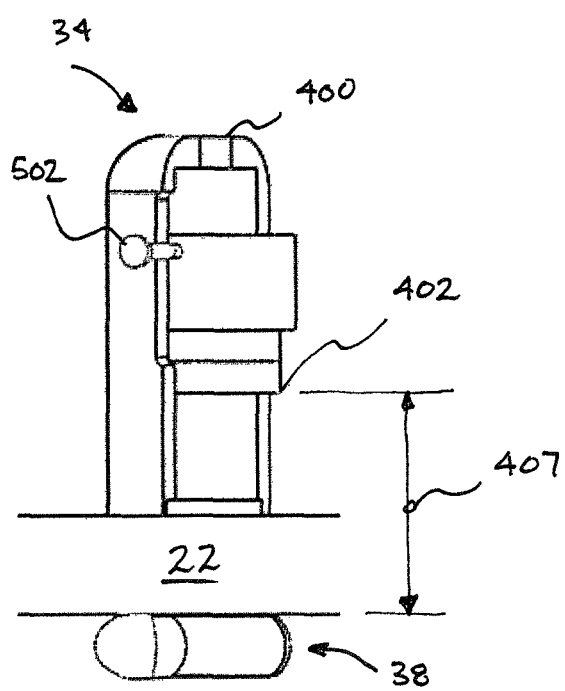

As shown in FIGS. 13A-13D, in some embodiments, housing 400 of apparatus 34 includes control mechanism that comprises an adjustment slot 506 and arm 502. FIGS. 13A and 13B depict a side view and a partially cutaway view, respectively, of one embodiment of apparatus 34 with primary magnetic field source 402 adjusted such that distance 407 is at a minimum and magnetic force between device 38 and apparatus 34 is at a maximum. FIGS. 13C and 13D depict a side view and a partially cutaway view, respectively, of one embodiment of apparatus 34 with primary magnetic field source 402 adjusted such that distance 407 is more than a minimum, and such that magnetic force between device 38 and apparatus 34 is less than a maximum. In some embodiments, arm 502 is coupled to primary magnetic field source 402 such that arm 502 extends through adjustment slot 506 and can be manipulated from outside housing 400. By manipulating arm 502, distance 407 between primary magnetic field source 402 and device 38 may be modified, which modifies the magnetic field. Primary magnetic field source 402 may be moved closer to or further away from device 38 within housing 400 depending on the desired magnetic field strength, but housing 400 will not move relative to device 38. In some embodiments, arm 502 comprises a threaded bolt such that the bolt may be loosened to move primary magnetic field source 402, and bolt may be tightened to fix primary magnetic field source 402 at a desired distance 407 from device 38.

In other embodiments, a similar configuration as shown in FIGS. 13A-13D may be used, except in these embodiments, control mechanism is automated through the feedback loop as described above regarding FIGS. 2-3B. That is, control mechanism is configured to receive a signal corresponding to a property of the magnetic field and adjust distance 407 from primary magnetic field source 402 to device 38 according to that signal. For instance, if the value of the magnetic force exceeds a set-point value by more than an acceptable tolerance, control mechanism will move primary magnetic field source 402 further away from device 38. In other words, control mechanism will move primary magnetic field source 402 within housing 400 further away from device 38, but housing 400 will not move relative to device 38. If the value of the magnetic force is less than set-point value by more than a tolerance, control mechanism will move coupling end closer to bottom side.

Figure 14A:
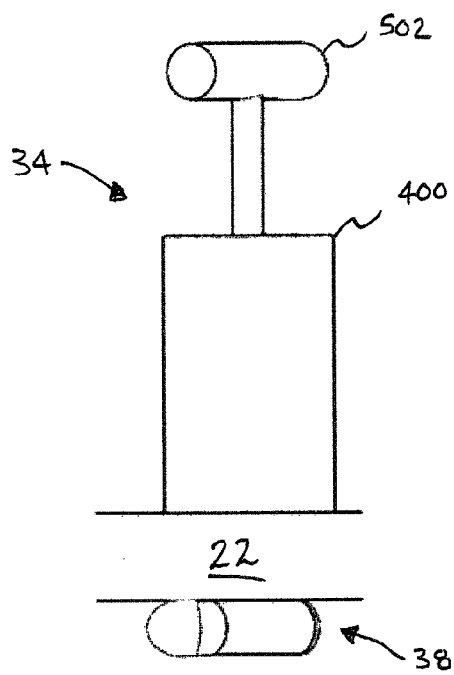
FIGS. 14A-14D illustrate embodiments of an apparatus configured to change the distance between a primary magnetic field source and a surgical device.
Figure 14B:
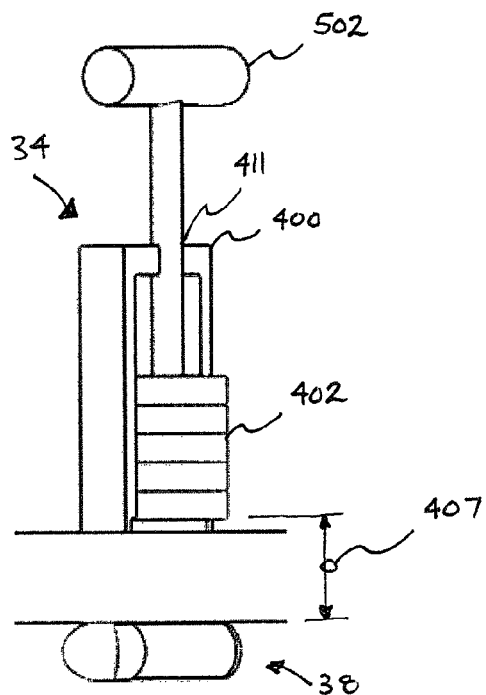
Figure 14C:
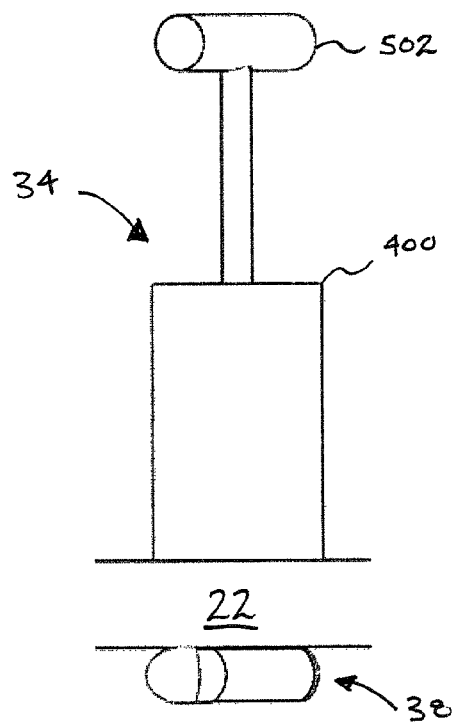
Figure 14D:
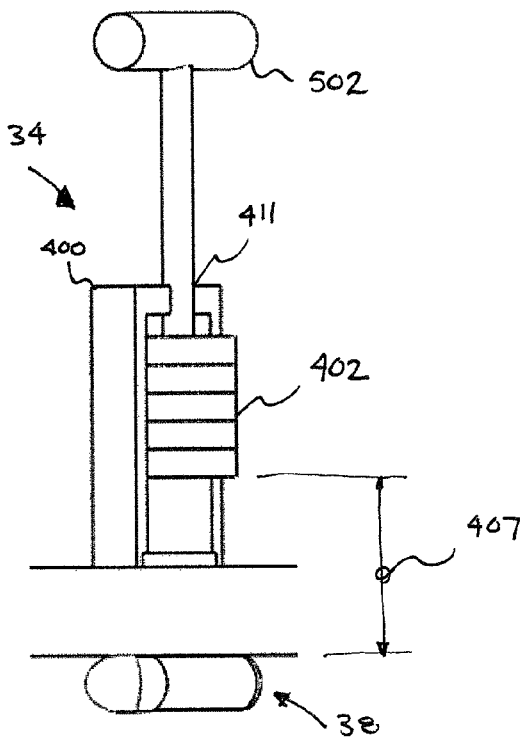

As shown in FIGS. 14A-14D, in other embodiments, housing 400 includes an opening 411 in the top. In some embodiments, opening 411 is a threaded opening. FIGS. 14A and 14B depict a side view and a partially cutaway view of one embodiment of apparatus 34 with primary magnetic field source 402 adjusted such that distance 407 is at a minimum, and such that magnetic force between device 38 and apparatus 34 is at a maximum. FIGS. 14C and 14D depict a side view and a section view of one embodiment of apparatus 34 with primary magnetic field source 402 adjusted such that distance 407 is more than a minimum, and such that magnetic force between device 38 and apparatus 34 is less than a maximum. In the embodiment shown, the control mechanism comprises an arm 502 coupled to primary magnetic field source 402. In embodiments where opening 411 is threaded, arm 502 extends through threaded opening 411 such that arm 502 can be manipulated from outside the housing. By manipulating arm 502, primary magnetic field source 402 may be moved closer to or further away apparatus 34, changing distance 407 depending on the desired magnetic field strength. In other words, control mechanism will move primary magnetic field source 402 within housing 400 further away from device 38, but housing 400 will not move relative to device 38. In embodiments where opening 411 is threaded, turning arm 502 clockwise will cause primary magnetic source 402 to move closer device 38, and turning arm 502 counter-clockwise will cause primary magnetic source 402 to move further device 38. In other embodiments, turning arm 502 counter-clockwise will cause primary magnetic source 402 to move closer to device 38, and turning arm 502 clockwise will cause primary magnetic source to move further from device 38.

In other embodiments, a similar configuration as shown in FIGS. 14A-14D may be used, except in these embodiments, control mechanism is automated through feedback loop as described above regarding FIGS. 2-3B. That is, control mechanism is configured to receive a signal corresponding to a property of the magnetic field and adjust distance 407 from primary magnetic field source 402 to device 38 according to that signal. For instance, if the value of the magnetic force exceeds a set-point value by more than an acceptable tolerance, control mechanism will move primary magnetic field source 402 further away from device 38 and increase distance 407. If the value of the magnetic force is less than set-point value by more than a tolerance, control mechanism will move coupling end closer to bottom side and decrease distance 407.

One skilled in the art will appreciate that embodiments of control mechanisms besides those illustrated in FIGS. 12A-14D may be used to move primary magnetic field source 402 within housing 400 relative to device 38. In some embodiments, control mechanism is entirely within housing 400 and does not comprise arm 502. In other embodiments, control mechanism is entirely within housing 400 and comprises arm 502 that does not protrude through housing 400. In other embodiments, control mechanism is inside housing 400 and automated. Examples of control mechanisms that may be used to move primary magnetic field source include: a hydraulic lift; a pneumatic lift; a wheel and pulley; or interlocking gears.

Apparatus 34, device 38, primary magnetic field source 402, or any or all of the three and associated components must be sterile before being used in surgery. In some embodiments, apparatus 34, device 38, or primary magnetic field source 402 may be sterile and/or may be sterilized or may undergo a sterilization process. In some embodiments, apparatus 34, device 38, or primary magnetic field source 402 and associated components may be placed in a sterile, sealed packaging, which may be removed before surgery. In other embodiments, apparatus 34, device 38, or primary magnetic field source 402 may be wrapped in a sterile barrier (e.g. a sheet, a paper or a film) before being used in surgery. Apparatus 34, device 38, and/or primary magnetic field source 402 may be themselves be sterile.

In embodiments where primary magnetic field source 402 is not removable from apparatus 34 or device 38, primary magnetic field source 402 may or may not be separately sterilized and/or sterile. In embodiments where primary magnetic field source is configured to be removable from apparatus 34 or device 38, primary magnetic field source 402 may be sterile or separately sterilized. In embodiments where primary magnetic field source 402 is configured to be removable from apparatus 34 or device 38 and primary magnetic field source 402 will not contact the patient during surgery, primary magnetic field source 402 may or may not be separately sterilized and/or sterile.

In each of the embodiments discussed in FIGS. 15A-34C, magnets are disposed substantially as depicted in FIG. 4. That is, apparatus 34 (or second platform 34) comprises a primary magnetic field source 402. Primary magnetic field source 402 may comprise one or more magnets 404. Device 38 (or first platform 38) comprises at least a magnet 220. Certain features of apparatus 34 and device 38, such as the housings 400, 202 have been omitted from these drawings for clarity.

Figure 15A:
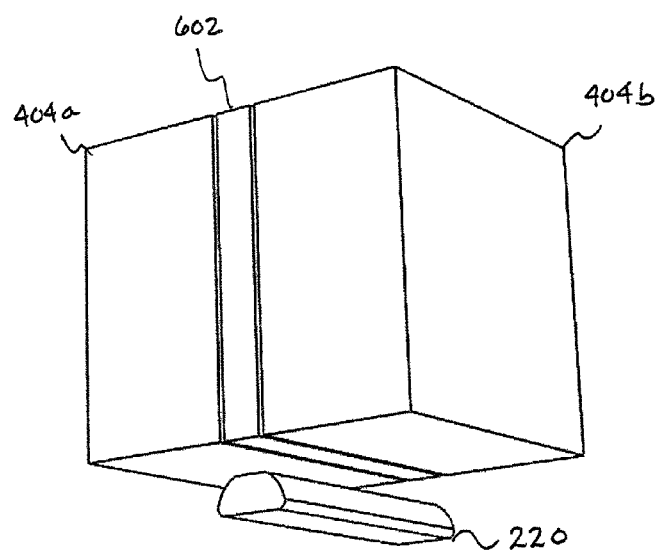
FIGS. 15A-15C illustrate embodiments of a configuration of magnets configured to modulate the strength of the primary magnetic field.
Figure 15B:
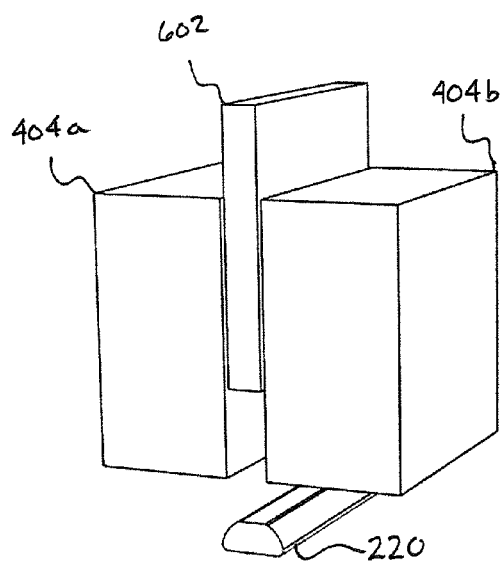
Figure 15C:
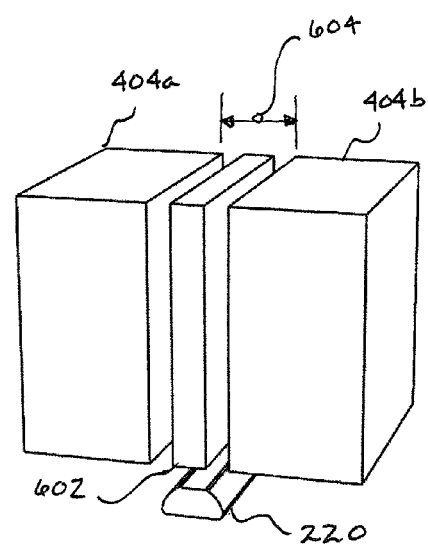

FIGS. 15A-C illustrate various views of a "rudder" magnet configuration for use with the second platform 34. As illustrated substantially in FIG. 4 above, the apparatus includes a platform 34 configured to be magnetically coupled to an object 38 disposed within a body cavity of a patient through a tissue 22. Platform 34 may include a first magnet 404a having an N pole and an S pole along a horizontal axis. Platform 34 has a longitudinal axis and the first magnet 404a has an N pole and an S pole along an axis that is more parallel with than perpendicular to the longitudinal axis. The platform may also include a second magnet 404b having an N pole and an S pole. Second magnet 404b may be disposed along the horizontal axis such that the N poles of first and second magnets 404a, 404b are closer to each other than are the S poles of first and second magnets 404a, 404b. For example, first magnet 404a and second magnet 404b may include prismatic permanent magnet stacks positioned with their magnetization axes horizontally, and facing each other in repulsion.

This arrangement is configured to produce a strong magnetic field in the vertical plane of symmetry between the two rudder magnets, as compared with previous magnet configurations. Consequently, a strong vertical coupling and strong torsional stiffness result.

Each of the components of the present apparatuses and/or devices may be sterile and/or sterilized. For example, the apparatus may include a sterile platform comprising at least one of a magnetically-attractive material and a materially capable of being magnetically-charged. Additionally, the apparatus may be provided in sterile packaging.

An embodiment of the apparatus includes a spacer 602 disposed between first magnet 404a and second magnet 404b. Spacer 602 may form a gap 604 between first magnet 404a and second magnet 404b. Additionally, the apparatus may include a control mechanism 300 configured to adjust gap 604 between first magnet 404a and second magnet 404b as illustrated in FIG. 15C. Alternatively, as illustrated in FIG. 15B, control mechanism 300 may adjust a position of spacer 602, thereby altering the magnetic flux delivered to target 220 by first and second magnets 404a, 404b. In another embodiment, the apparatus includes a third magnet disposed between first magnet 404a and second magnet 404b. Control mechanism 300 may similarly control the position of the third magnet to modulate the magnetic flux. The third magnet may be an electromagnet 900. Additionally, the apparatus may include a current source (not shown) coupled to electromagnet 900 and a control device for adjusting a level of a current provided to electromagnet 900 by the current source.

FIG. 16 illustrates one embodiment of an apparatus. In this embodiment, the apparatus includes a platform 34 configured to be magnetically coupled to an object 38 disposed within a body cavity of a patient through a tissue 22, where platform 34 includes a magnet assembly 700 and a magnetic field modifier 708. As illustrated in FIG. 16A, magnetic assembly 700 may have a first leg 702, a second leg 704, and a bridge 706 extending from first leg 702 to second leg 704. Magnetic field modifier 708 may interfere with a magnetic field generated by magnet assembly 700.

In one embodiment, bridge 706 is in direct contact with first and second legs 702, 704. Alternatively, bridge 706 is not in direct contact with first and second legs 702, 704. Bridge 706 may comprise a ferromagnetic material, such as steel. Alternatively, the bridge may comprise another magnet.

As illustrated in FIG. 16C, where the arrows indicate a direction of magnetization, first leg 702 includes a first magnet 404a having a first direction of magnetization. Second leg 704 may include a second magnet 404b having a second direction of magnetization opposite the first direction of magnetization. In one embodiment, bridge 706 may include a third magnet having a third direction of magnetization that is more perpendicular to than parallel with the first direction of magnetization. Magnetic field modifier 708 may include a magnet having a direction of magnetization that is more perpendicular to than parallel with the first direction of magnetization.

Additionally, as shown in FIG. 16B, the apparatus may include an adjustment mechanism 710 coupled to magnetic field modifier 708. Adjustment mechanism 710 may adjust a position of magnetic field modifier 708. In one embodiment, adjustment mechanism 710 may include a groove, slot, key hole or other receiver. Alternatively, adjustment mechanism 710 may include a protrusion or other type of rotatable member. Adjustment mechanism 710 may change a location of a magnetic pole created by magnetic field modifier 708. In particular, magnetic field modifier 708 may be rotatable about an axis.

Figure 17A:
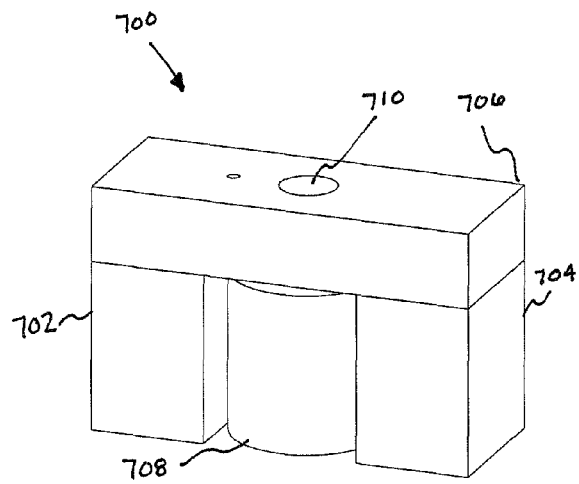
FIGS. 17A-17E illustrate embodiments of a configuration of magnets configured to modulate the strength of the primary magnetic field.
Figure 17B:
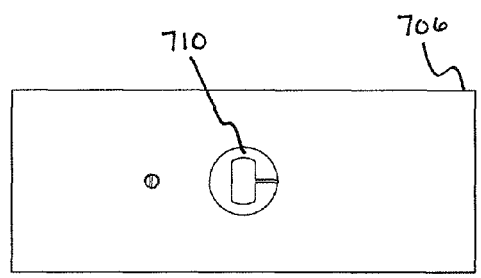
Figure 17C:
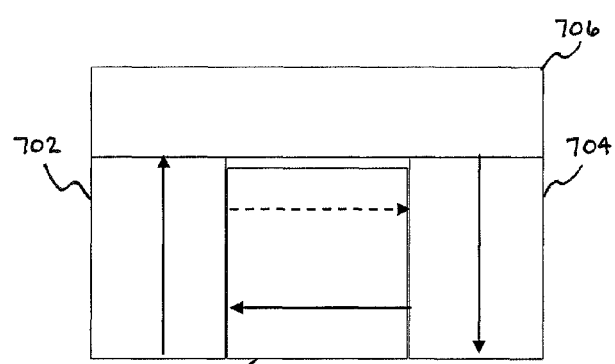
Figure 17D:
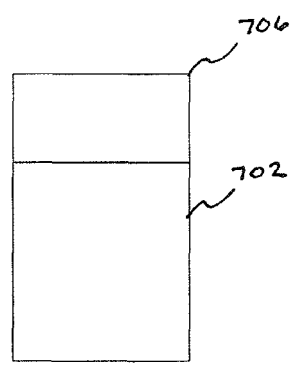
Figure 17E:
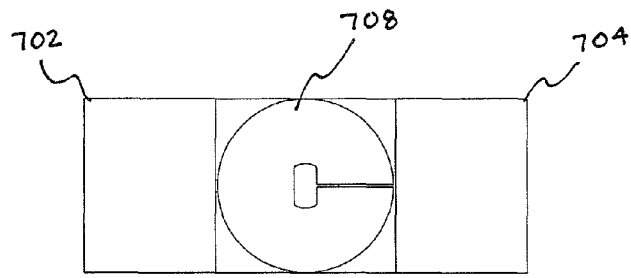
Figure 18A:
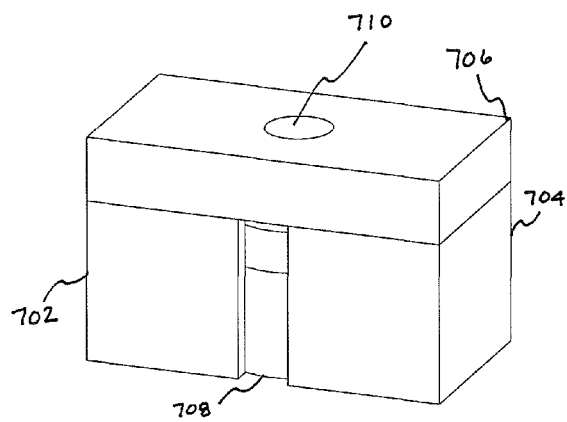
FIGS. 18A-18F illustrate embodiments of a configuration of magnets configured to modulate the strength of the primary magnetic field.
Figure 18B:
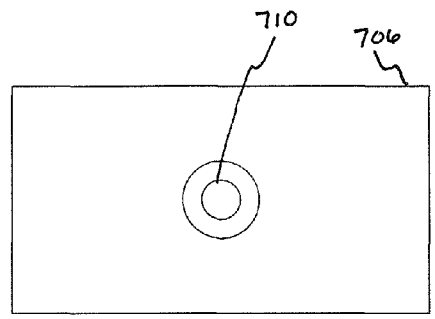
Figure 18C:
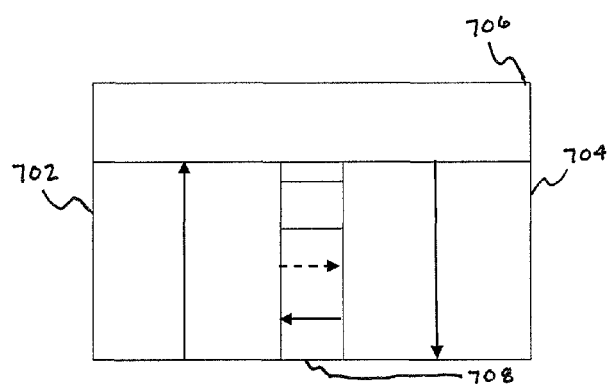
Figure 18D:
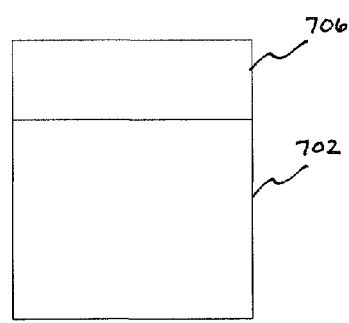
Figure 18E:
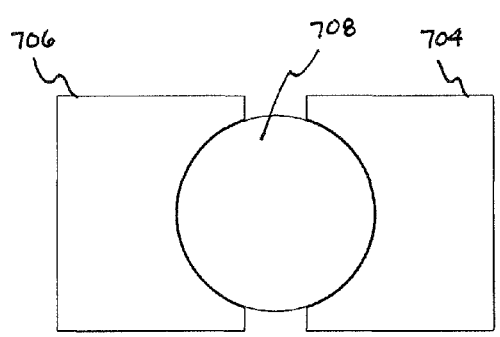
Figure 18F:
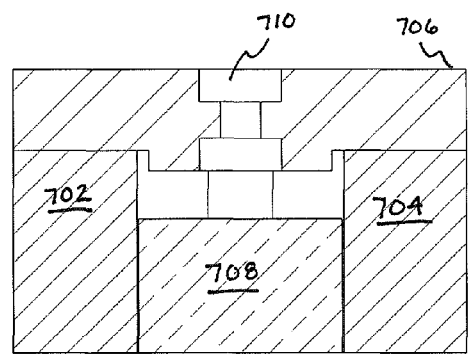

As illustrated in FIGS. 16A and C, first leg 702 has a first leg surface, second leg 704 has a second leg surface, bridge 706 has two bridge surfaces, the first leg surface is oriented at a 45-degree angle to one of the two bridge surfaces, and the second leg surface is oriented at a 45-degree angle to the other of the two bridge surfaces. Alternatively, as shown in FIGS. 17A and C, the first leg surface is parallel to the bridge surface, and the second leg surface is to the bridge surface.

In another alternative embodiment illustrated in FIG. 18, first leg 702 partially encloses magnetic field modifier 708, and second leg 704 partially encloses magnetic field modifier 708. For example, as shown, first leg 702 and second leg 704 may partially wrap around field modifier 708. This configuration may increase the field strength as well as the torque of magnet assembly 700.

Figure 19A:
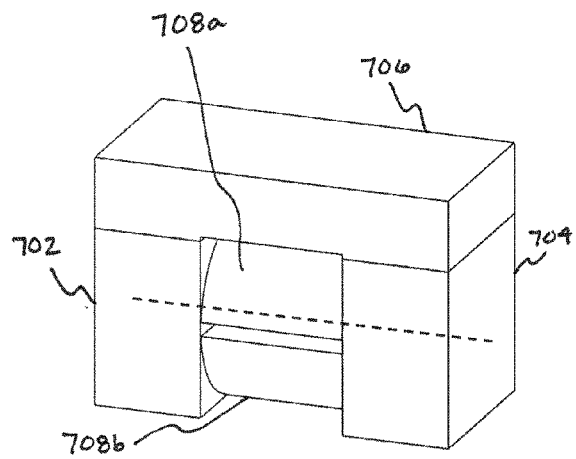
FIGS. 19A-19F illustrate embodiments of a configuration of magnets configured to modulate the strength of the primary magnetic field.
Figure 19B:
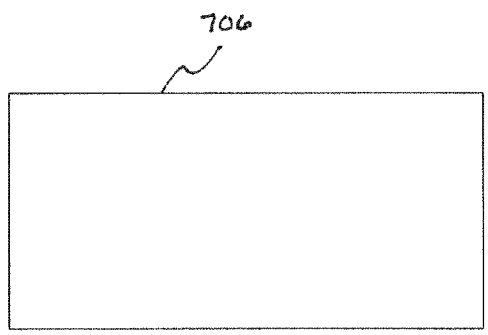
Figure 19C:
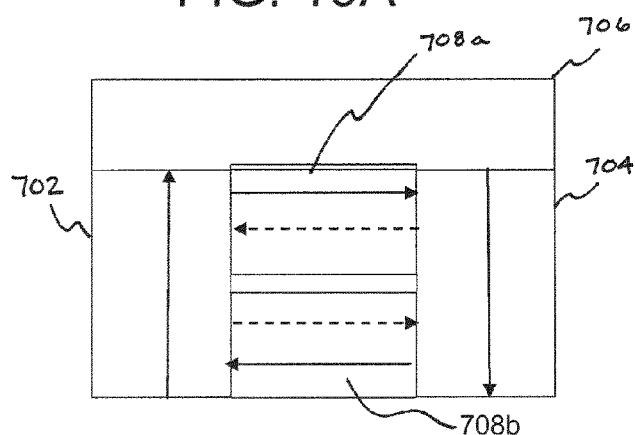
Figure 19D:
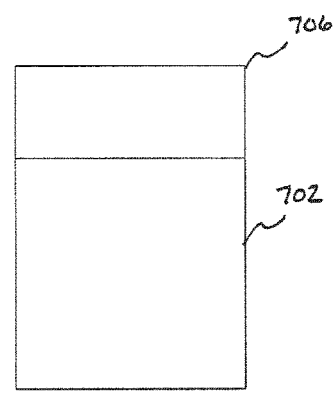
Figure 19E:
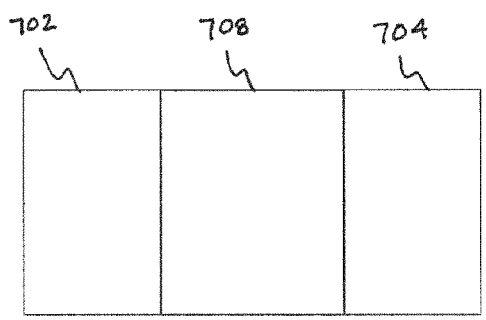
Figure 19F:
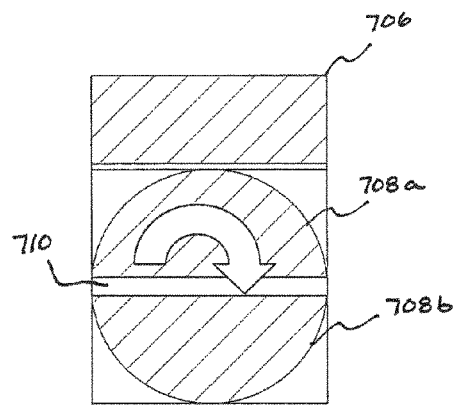

In one embodiment, magnetic field modifier 708 is rotatable about an axis that is more perpendicular to than parallel with the first direction of magnetization as shown in FIGS. 19A and 19F. In a further embodiment, magnetic field modifier 708 may include two pieces 708a, 708b as illustrated in FIGS. 19A, 19C, and 19F.

As illustrated in FIG. 16A, magnetic field modifier 708 may be positioned between first leg 702 and second leg 704. In a further embodiment, magnetic field modifier 708 may be positioned below bridge 706, such that first leg 702, second leg 704, and bridge 708 partially contain magnetic field modifier 708.

In one embodiment, the reaching power of the magnet (i.e., depth of field) is related to the distance between legs 702, 704 of magnet assembly 700. Additionally, the thickness of legs 702, 704 may increase the force at distance. One benefit of the arch shape illustrated in FIGS. 16-19 is a reduction in flux leakage, and therefore, a reduction in unintended attraction, of e.g., surgical instruments.

Figure 20:
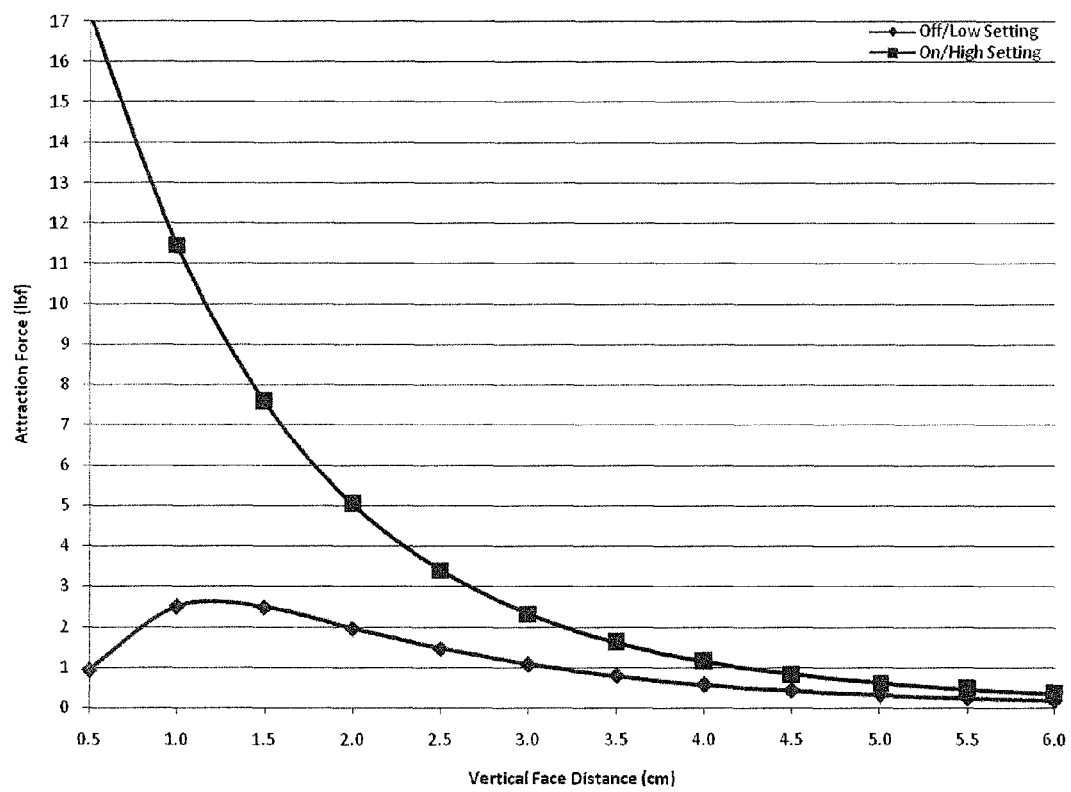
FIG. 20 is a graph showing the attraction force (lb-f) as a function of the vertical face distance (cm) for the embodiments illustrated in FIGS. 16-19.

FIG. 20 is a graphical representation of test data of the magnet assembly 700. The line with diamond points represents the attraction force with respect to vertical distance from magnet assembly 700 when magnetic field modifier 708 is set to an off/low setting. The line with square points represents the attraction force with respect to vertical distance from magnet assembly 700 when magnetic field modifier 708 is set to an on/high setting. As illustrated, the attraction force is much higher at close range with magnetic field modifier 708 set to the on/high setting. These two extremes form an envelope of response curves. Thus, if magnetic field modifier 708 is set to a lesser more moderate setting, the response curve would fall somewhere between the on/high curve and the off/low curve.

The off/low setting is illustrated in FIG. 16C as the solid arrow on magnetic field modifier 708 and the on/high setting is illustrated as the dotted line. With field modifier 708 set to the off/low setting, the magnetic field has a circuit to flow through. For example, the field may follow the direction of magnetization arrows shown in FIG. 16C from first leg 702 through bridge 706 to second leg 704. However, when field modifier 708 is set to the on/high setting, this flow is interrupted, which distorts the field to increase the attraction force of magnet assembly 700.

Figures 21A, 21B:
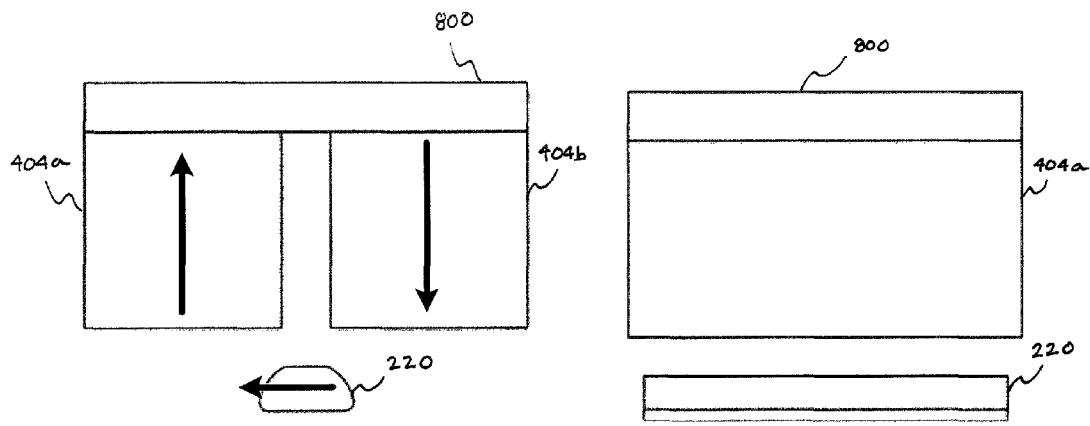
FIGS. 21A-21E illustrate embodiments of a configuration of magnets configured to modulate the strength of the primary magnetic field.
Figure 21C:
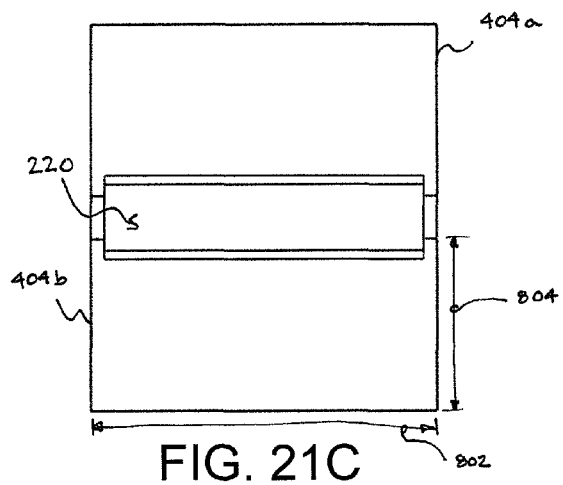

FIGS. 21A-21E illustrate embodiments of a platform configured to be magnetically coupled to an object disposed within a body cavity of a patient through a tissue 22, where first platform 34 has a longitudinal axis. In some embodiments, platform is apparatus 34. FIG. 21A illustrates a front view, FIG. 21B illustrates a side view, and FIG. 21C illustrates a bottom view of platform 34 comprising magnets 404a, 404b, and support member 800. In the embodiment shown, platform 34 is configured to be coupled to device 38 that comprises magnet 220.

In this embodiment, as shown in FIGS. 21A-21C, the platform may include a first magnet 404a and a second magnet 404b coupled to the platform. In some embodiments, platform comprises support member 800 to provide lateral support to magnets 404a and 404b. In other embodiments, support member 800 may be omitted.

Embodiments depicted in FIGS. 21A-21E are configured to be magnetically coupled to magnet 220, which, in some embodiments, is coupled to device 34. In some embodiments illustrated in FIGS. 21A-21E, magnets 404a and 404b have substantially identical geometries. That is, longitudinal dimension 802 of first magnet 404a is equal to longitudinal dimension 802 of second magnet 404b; lateral dimensions 804 and vertical dimension 806 are equal as well. First magnet 404a may have an N pole and an S pole along a first magnet axis that is more perpendicular to than parallel with the longitudinal axis. In particular, first magnet 404a may have a first magnet longitudinal axis that is more perpendicular to than parallel with the first magnet axis, and a first longitudinal dimension 802 that is taken along a line that is parallel to the first magnet longitudinal axis. In such an embodiment, first longitudinal dimension 802 is greater than any lateral dimension 804 or vertical dimension 806 of first magnet 404a that is taken along a line that is perpendicular to the first magnet longitudinal axis. Second magnet 404b may have an N pole and an S pole along a second magnet axis that is more perpendicular to than parallel with the longitudinal axis. Second magnet 404b may have a second magnet longitudinal axis that is more perpendicular to than parallel with the second magnet axis, and a second longitudinal dimension 802 that is taken along a line that is parallel to the second magnet 404b longitudinal axis. In such an embodiment, second longitudinal dimension 802 is greater than any lateral dimension 804 or vertical dimension 806 of second magnet 404b that is taken along a line that is perpendicular to the second magnet longitudinal axis.

Figures 21D, 21E:
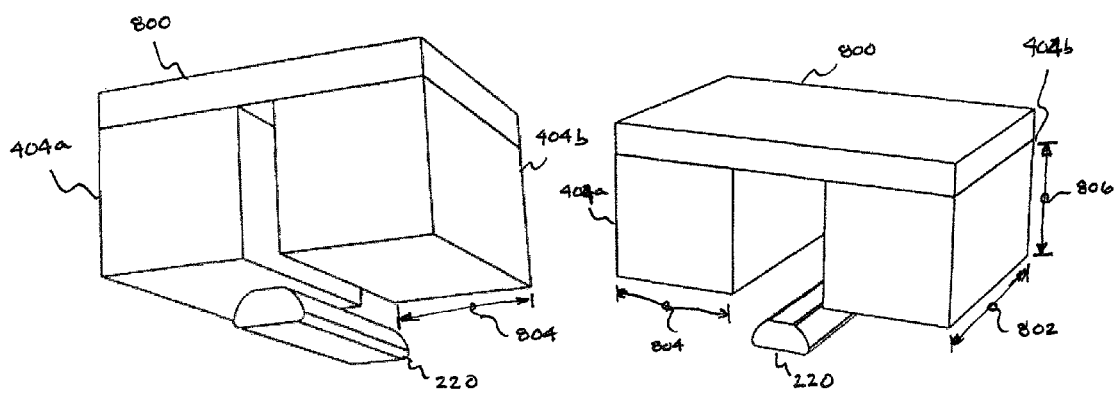
Figure 22A:
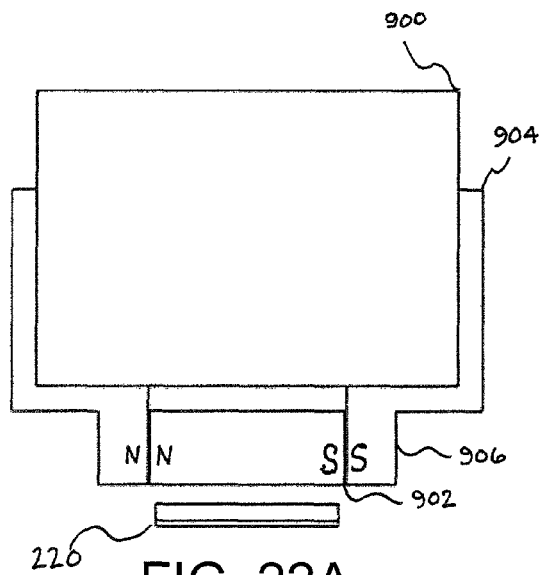
FIGS. 22A-22E illustrate embodiments of a configuration of magnets configured to modulate the strength of the primary magnetic field.
Figure 22B:
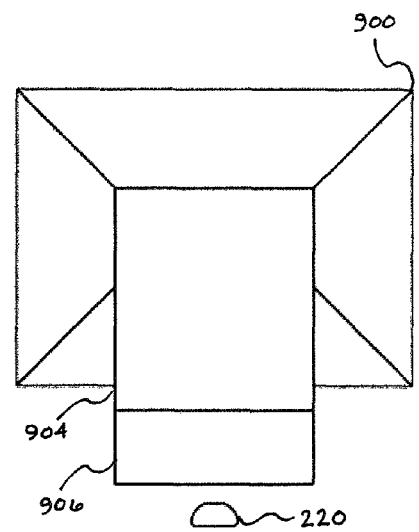
Figure 22C:
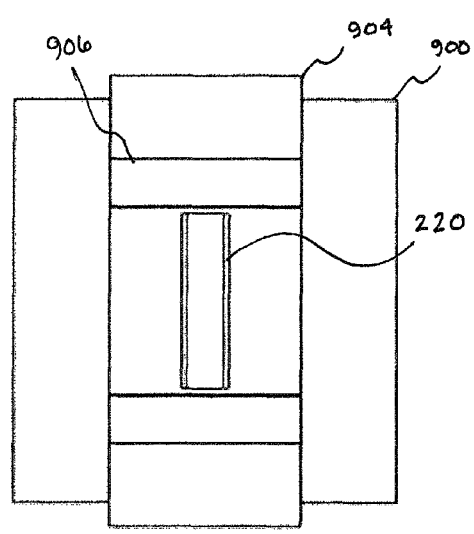
Figure 22D:
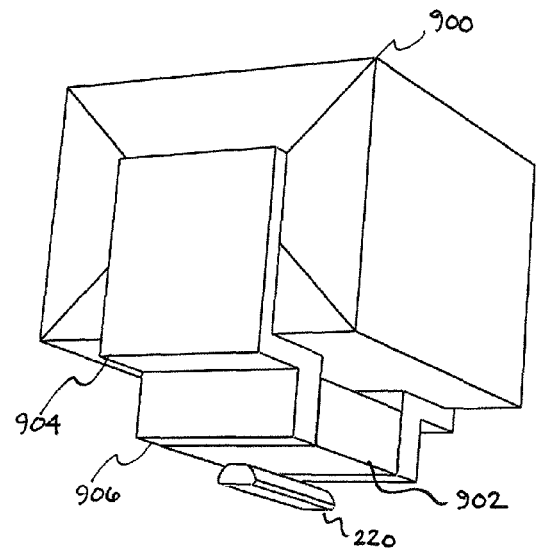
Figure 22E:
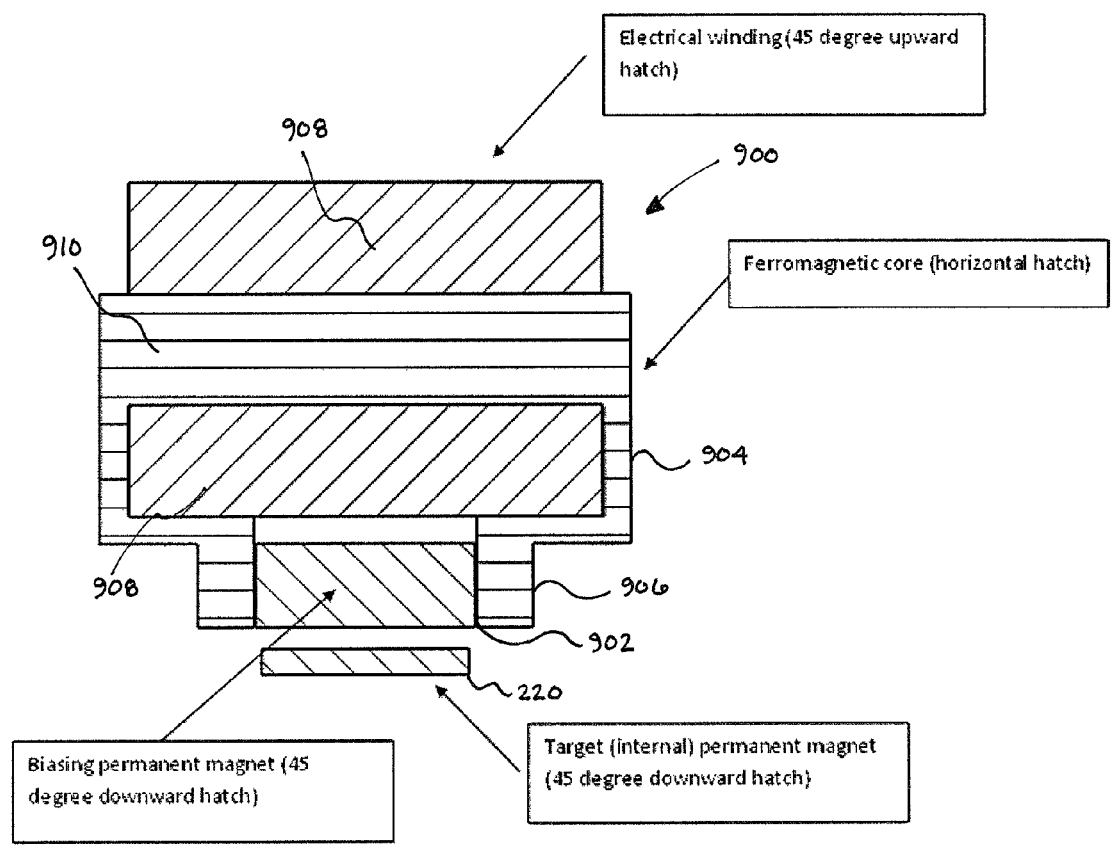

As shown in FIGS. 21C-21E, the strength of the magnetic field may be modulated by changing the geometry of magnets 404a, 404b. For example, decreasing lateral dimension 804 would modulate the magnetic field by decreasing the magnetic field strength between magnets 404a, 404b and magnet 220. Increasing lateral dimension 804 would modulate the magnetic field by increasing the magnetic field strength between magnets 404a, 404b and magnet 220. Dimensions 802, 804, 806 may be increased or decreased by, e.g. reorienting magnets 404a, 404b or replacing magnets 404a, 404b with magnets with larger or smaller dimensions.

In a further embodiment as shown in FIG. 21A, a second platform 34 may be configured to be inserted within a body cavity of a patient and magnetically coupled to first platform 38 across a tissue 22, where second platform 34 includes a magnet 220 that has an N pole and an S pole along an axis that is more perpendicular to than parallel with first magnet 404a axis. Alternatively, second platform 34 may comprise magnet 220 that has an N pole and an S pole along an axis that is more perpendicular to than parallel with the first magnet axis. The apparatus may also include top piece 800 coupled to the first and second magnets 404a, 404b. Top piece 800 may support member 800.

FIGS. 22A-22D illustrate one embodiment of an apparatus that includes an electromagnet 900. For example, the apparatus may include a platform 34 configured to be magnetically coupled to an object 38 disposed within a body cavity of a patient through a tissue 22. Platform 34 may include an electromagnet 900 coupled to platform 34 and a permanent magnet 902 coupled to electromagnet 900. In particular, an N pole of electromagnet 900 is coupled to an N pole of permanent magnet 902 and an S pole of electromagnet 900 is coupled to an S pole of permanent magnet 902.

Electromagnet 900 may include a ferromagnetic core 910 that includes a first electromagnetic flux channel 904 and a second electromagnetic flux channel 904. Electromagnet 900 may additionally include a conductor coil 908 wound around ferromagnetic core 910. In a particular embodiment, electromagnet 900 includes a horizontal winding 908 axis and a steel core 910 that is centered above and parallel to a prismatic permanent magnet 902 that is magnetized along its longitudinal axis. In a particular embodiment, permanent magnet 902 is magnetized in an opposite polarity to electromagnet 900.

The apparatus may also include a first electromagnetic flux channel 904 that has a first focusing pad 906 coupled to one of the N and S poles of permanent magnet 902. Similarly, the second electromagnetic flux channel 904 has a second focusing pad 906 coupled to the other of the N and S poles of the permanent magnet 902. For example, an electromagnetic flux channel 904 may protrude down from each end of a steel core 908. A steel focusing pad 906 may extend downward from the termination of each flux channel 904 along and end face of amplifying permanent magnet 902 toward a second permanent magnet 220 that serves as a target.

Target magnet 220 may be magnetized along its longitudinal axis, but opposite in direction to amplifying permanent magnet 902. If a large attractive force, i.e., lifting force, is desired between this hybrid magnet configuration and target magnet 220, electromagnet 900 is energized by a current source (not shown) in such a direction so as to polarize it opposite relative to amplifying permanent magnet 902. Alternatively, if the goal is to reduce the attraction force between hybrid magnet (comprising electromagnet 900 and permanent magnet 902) and target magnet 220, then the current flow in the electromagnet 900 may be reduced or the direction of flow may be reversed. This configuration may generate both strong attraction forces as well as high levels of torque as compared with a permanent magnet 902 used alone. Additionally, the variable levels of attraction force realized may reduce potential damage to human tissue 22.

The apparatus may also include a current source coupled to electromagnet 900. The apparatus may also include a control device for adjusting a level of a current provided to electromagnet 900 by the current source. In particular, electromagnet 900 may generate a variable amount of magnetic flux.

Figure 23A:
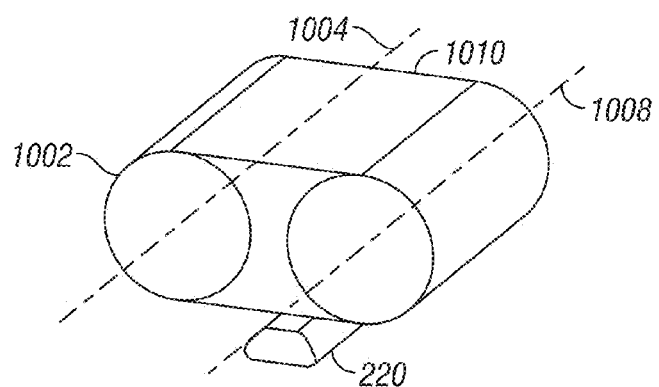
FIGS. 23A-23C illustrate embodiments of a configuration of magnets configured to modulate the strength of the primary magnetic field.
Figure 23B:
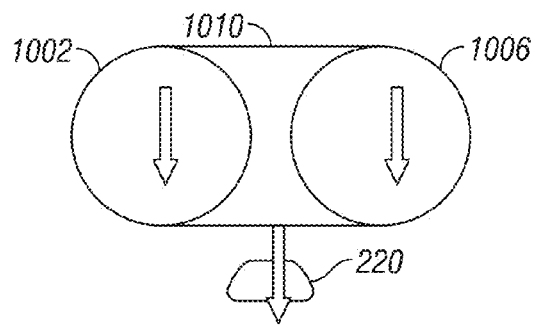
Figure 23C:
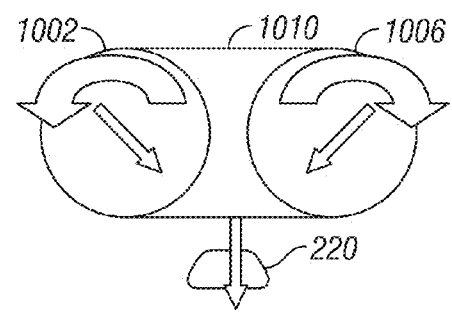

FIGS. 23A-23C illustrates another embodiment of an apparatus. As with several other embodiments, the apparatus may include a platform 34 configured to be magnetically coupled to an object 38 disposed within a body cavity of a patient through a tissue 22. In this embodiment, however, platform 34 may include a first rotatable magnet 1002 and a second rotatable magnet 1006 coupled to the platform as illustrated in FIG. 23A. First rotatable magnet 1002 may rotate about a first axis 1004 as shown in FIG. 23C. In particular, as shown in FIG. 23B, first rotatable magnet 1002 may have a direction of magnetization that is transverse to first axis 1004. Similarly, second rotatable magnet 1006 may rotate about a second axis 1008. Second rotatable magnet 1006 may also have a direction of magnetization that is transverse to second axis 1008.

In one embodiment, the platform further includes a coupler 1010 to which first and second rotatable magnets 1002, 1006 are rotatably coupled. In particular, first and second rotatable magnets 1002, 1006 may be coupled to coupler 1010 such that first axis 1004 and/or second axis 1008 are more parallel than perpendicular. In a particular embodiment, coupler 1010 may be configured to collect the magnetic field and direct it in the direction of use as illustrated. One advantage of this system is that it may be used with a single target magnet 220 rather than a combination of two target magnets 220 without greatly reducing the torque available.

In such an embodiment, first rotatable magnet 1002 and the second rotatable magnet 1006 are configured to emit interfering magnetic fields. The apparatus may include an adjustment mechanism configured to rotate at least one of first rotatable magnet 1002 and second rotatable magnet 1006, thereby adjusting the level of interference between the magnetic fields produced by first rotatable magnet 1002 and second rotatable magnet 1006.

In one embodiment, rotatable magnets 1002, 1006 are the same size. Additionally, rotatable magnets 1002, 1006 may be magnetized diametrically rather than through the length. In other words, the magnets may be magnetized transverse to their longitudinal axes 1004, 1008. The angle of rotation may control the location of a magnetic field focal point produced by the combination of first rotatable magnet 1002 and second rotatable magnet 1006.

Figure 24:
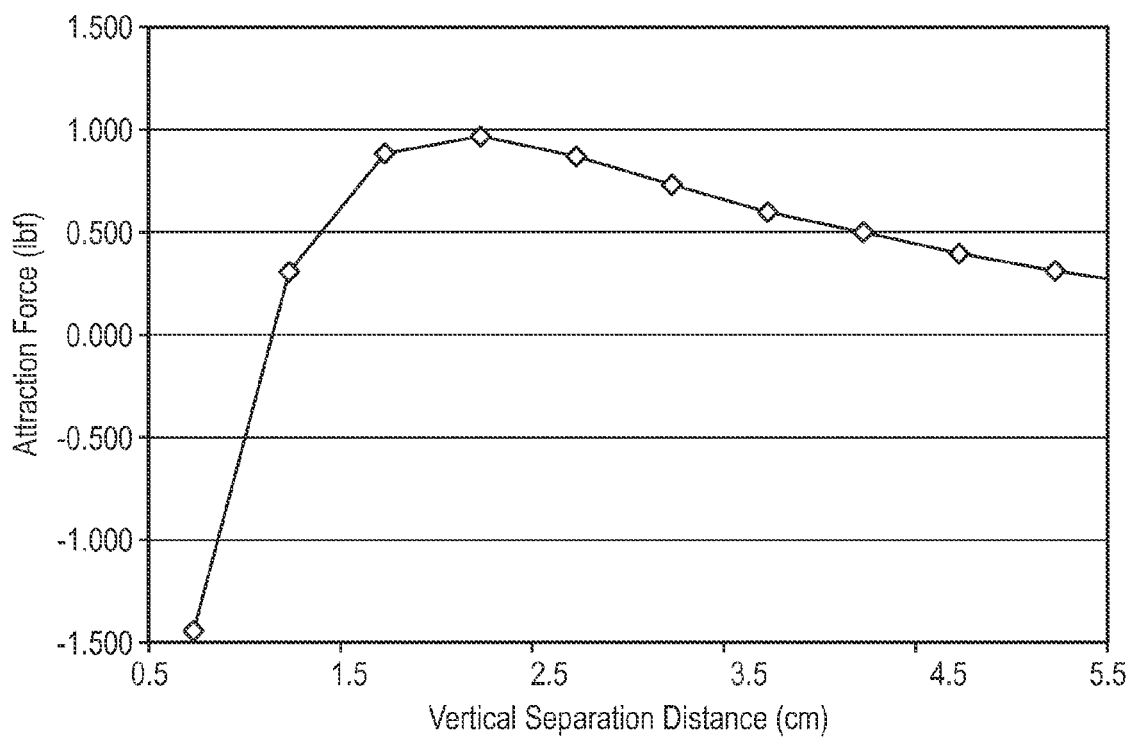
FIG. 24 is a graph showing the attraction force (lb-f) as a function of the vertical separation distance (cm) for the embodiments illustrated in FIGS. 23A-23C.
Figure 25A:
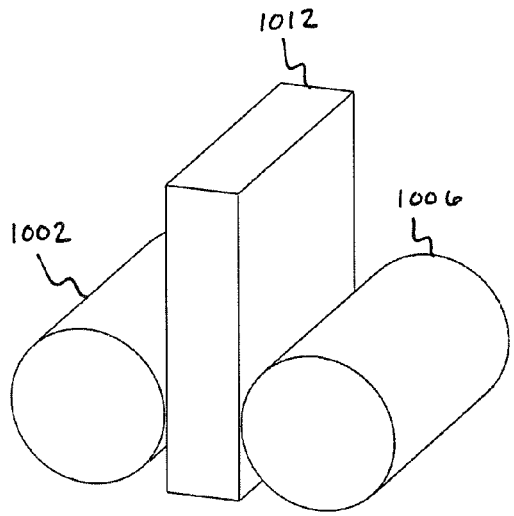
FIGS. 25A-25D illustrate embodiments of a configuration of magnets configured to modulate the strength of the primary magnetic field.
Figure 25B:
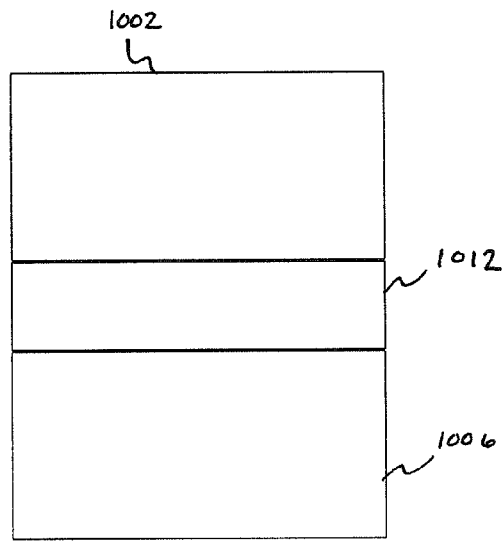
Figure 25C:
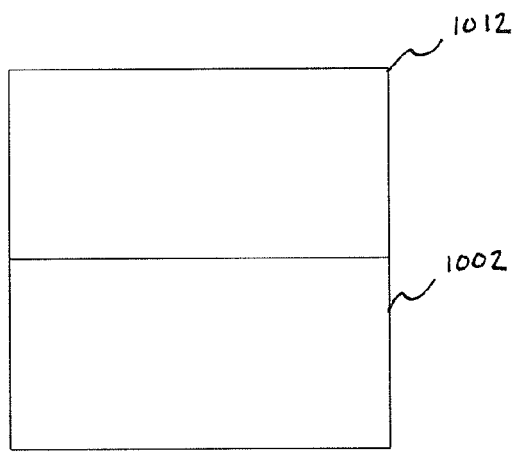
Figure 25D:
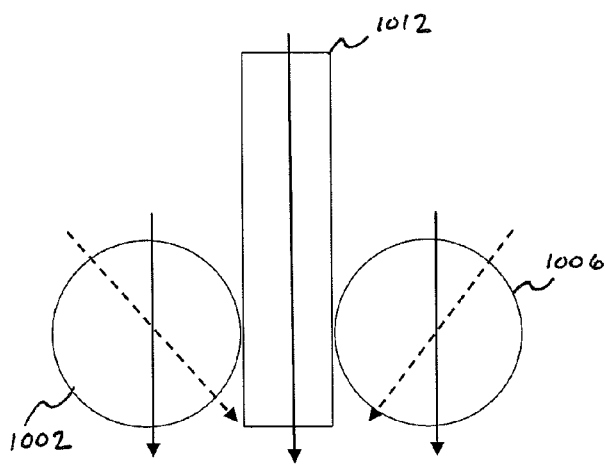
Figure 26A:
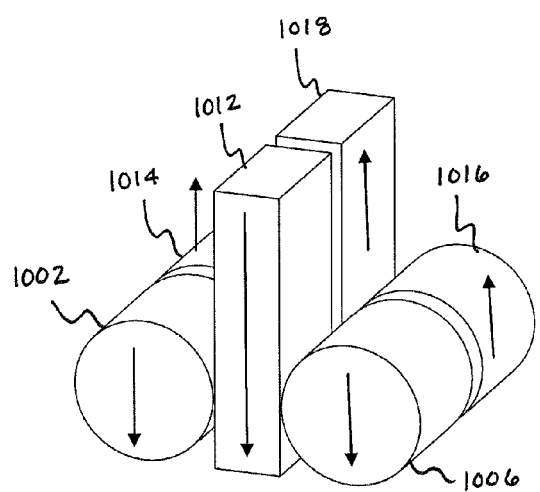
FIGS. 26A-26D illustrate embodiments of a configuration of magnets configured to modulate the strength of the primary magnetic field.
Figure 26B:
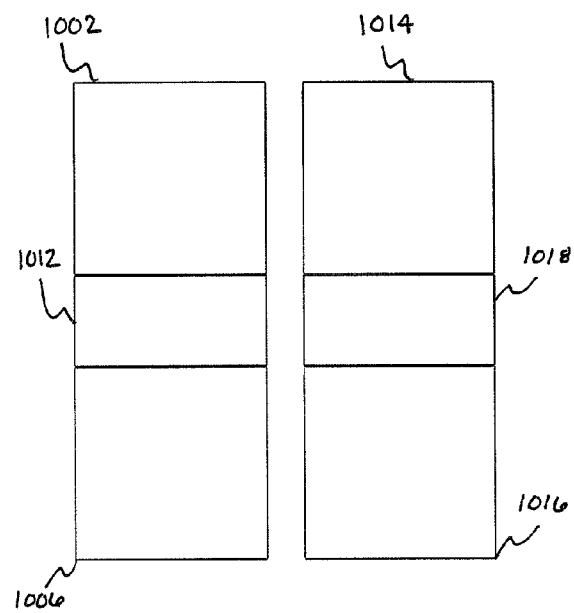
Figure 26C:
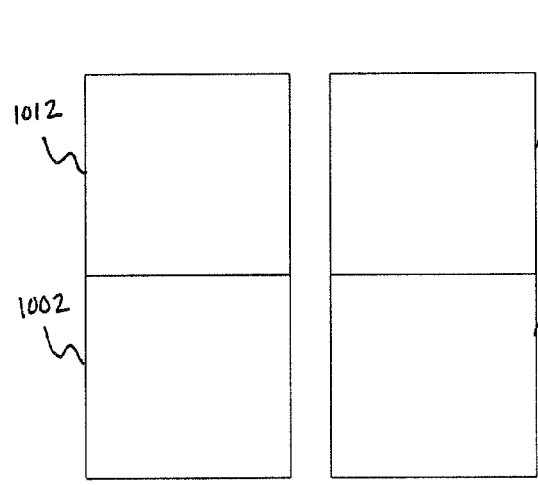
Figure 26D:
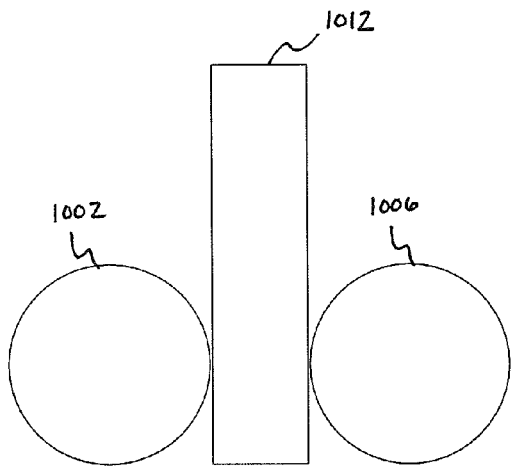

FIG. 24 is a graphical representation of data that describes the performance of the apparatus illustrated in FIG. 23. For this date, the angle of first rotatable magnet 1002 and second rotatable magnet 1006 is constant. The distance from target magnet 220 is varied. These results illustrate the focusing effect, because at the initial distance the magnet was too close for coupling, so the magnetic field pulled the internal magnet into position. As the distance between magnet platform 34 and target magnet 220 increases, the magnetic coupling increases, because the field of target magnet 220 is getting closer to a magnetic field focal point.

As illustrated in FIGS. 25A-25D, the platform may include a third magnet 1012 positioned between first rotatable magnet 1002 and second rotatable magnet 1006. In a further embodiment illustrated in FIGS. 26A-26D, the platform may include a fourth rotatable magnet 1014 axially aligned with first rotatable magnet 1002, a fifth rotatable magnet 1016 axially aligned with second rotatable magnet 1006, and a sixth magnet 1018 positioned between fourth rotatable magnet 1014 and fifth rotatable magnet 1016.

Figure 27:
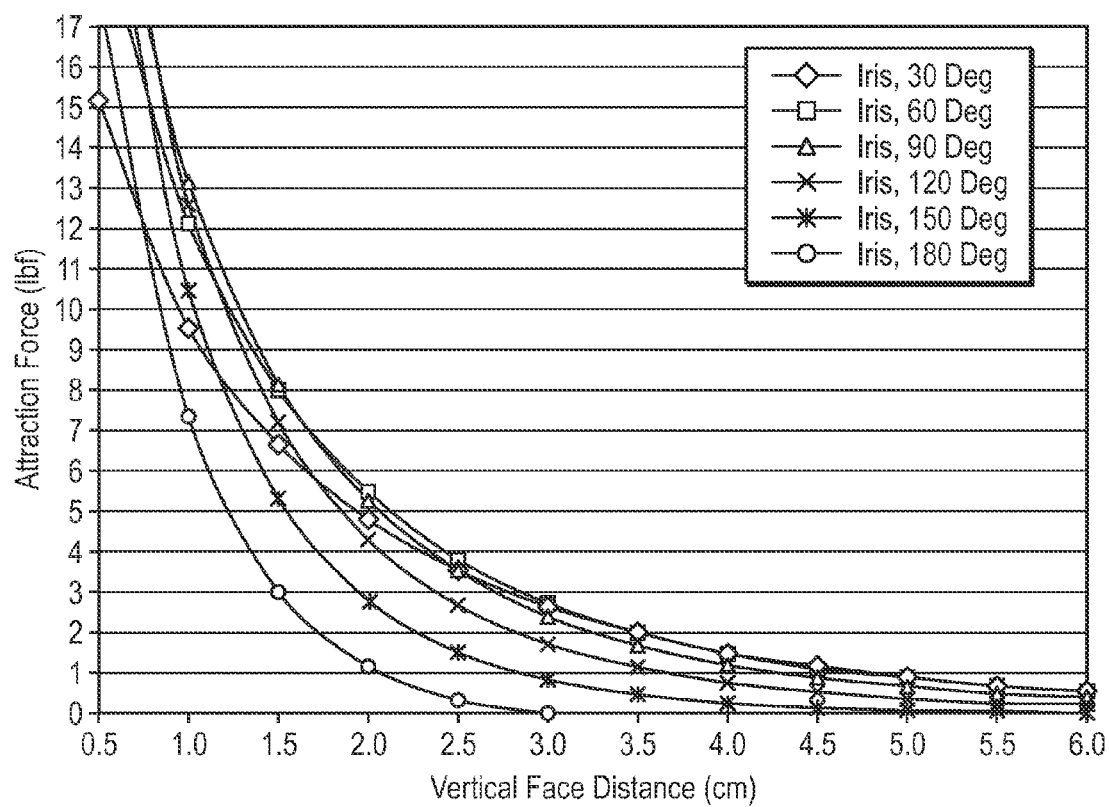
FIG. 27 is a graph showing the attraction force (lb-f) as a function of the vertical separation distance (cm) for the embodiments illustrated in FIGS. 23 and 25-26.
Figure 28:
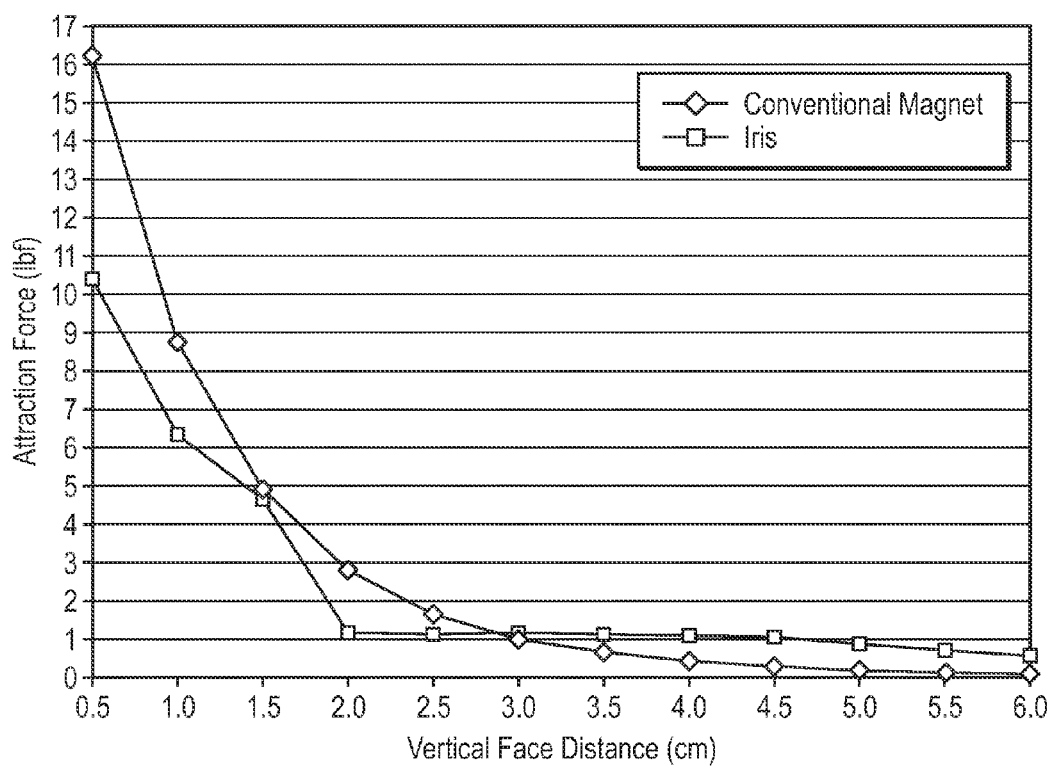
FIG. 28 is a graph showing the attraction force (lb-f) as a function of the vertical separation distance (cm) for the embodiments illustrated in FIGS. 23 and 25-26 and a conventional magnet.
Figure 29:
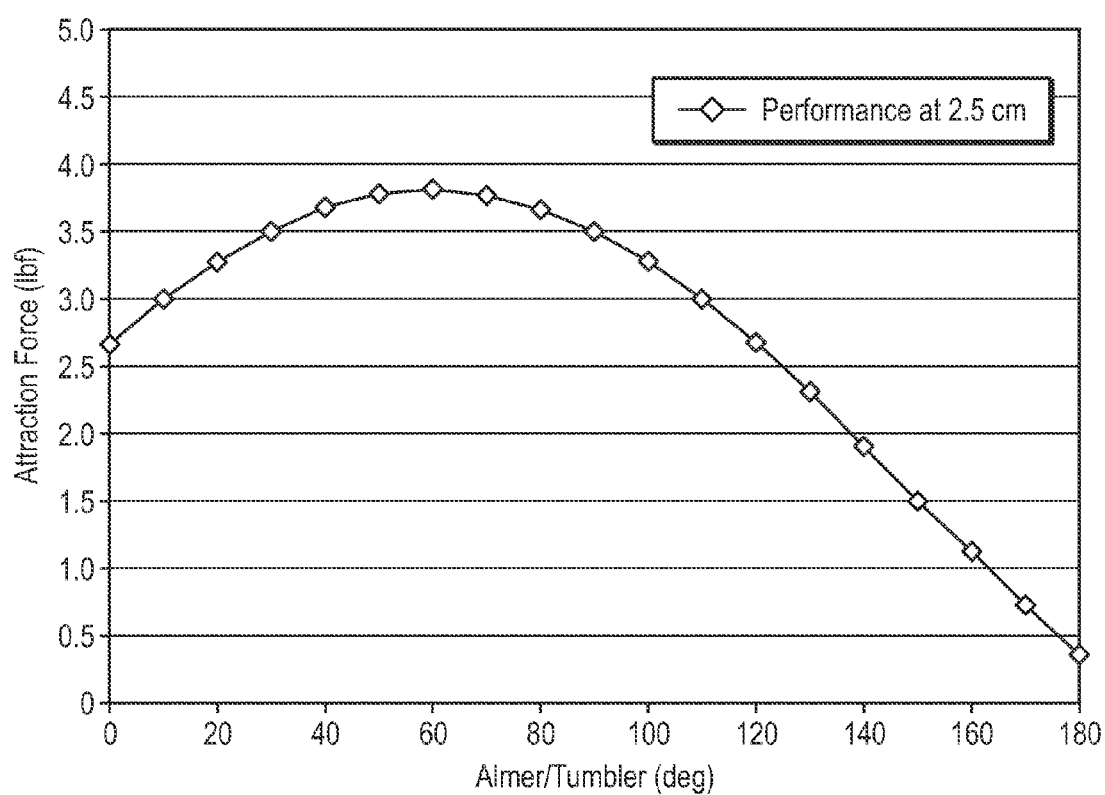
FIG. 29 is a graph showing the attraction force (lb-f) as a function of aimer/tumbler angle(deg) for the embodiments illustrated in FIGS. 23A-23C.

FIG. 27 illustrates data that shows the attraction force with respect to vertical distance between the rotatable magnets and target magnet 220 for various angles of rotation for rotatable magnets 1002, 1006. FIG. 28 compares the attraction force with respect to distance of a conventional magnet and the illustrated embodiments. As shown, the response curve is smoother and more predictable than with a conventional magnet. FIG. 29 illustrates the attraction force with respect to angle of rotation of rotatable magnets 1002, 1006 at a constant distance from target magnet 220. This curve illustrates the controllability of the attraction force through rotation of the magnets.

Figure 30A:
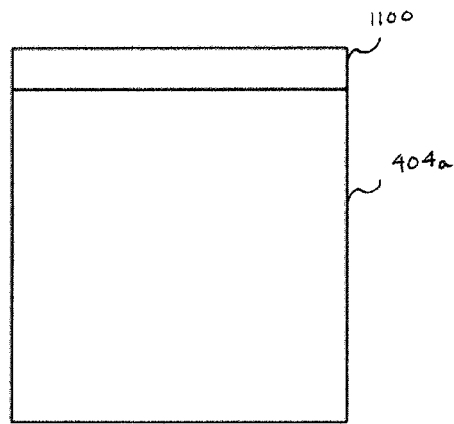
FIGS. 30A-30F illustrate embodiments of a configuration of magnets configured to modulate the strength of the primary magnetic field.
Figure 30B:
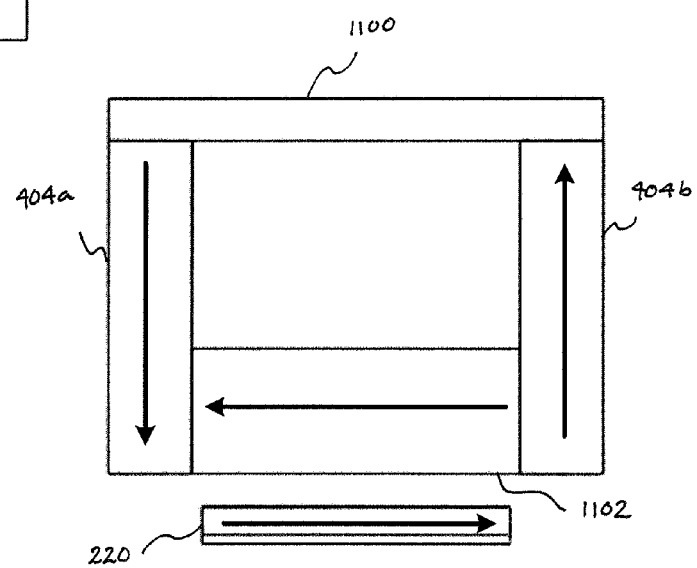
Figure 30C:
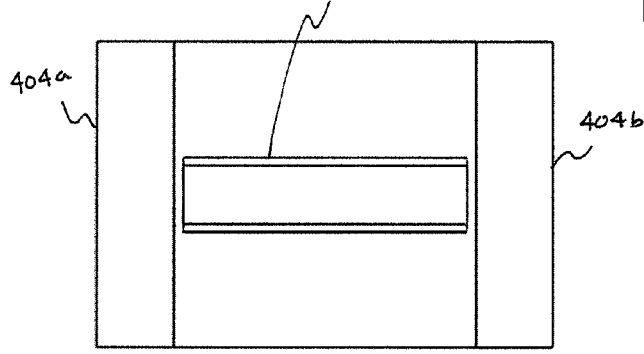
Figure 30D:
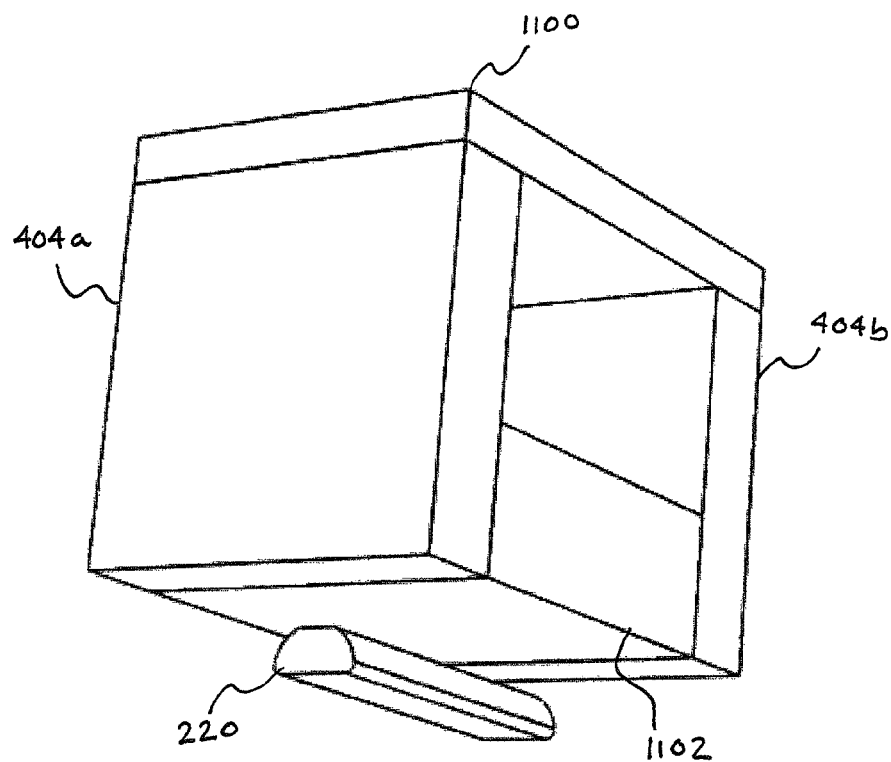
Figure 30E:
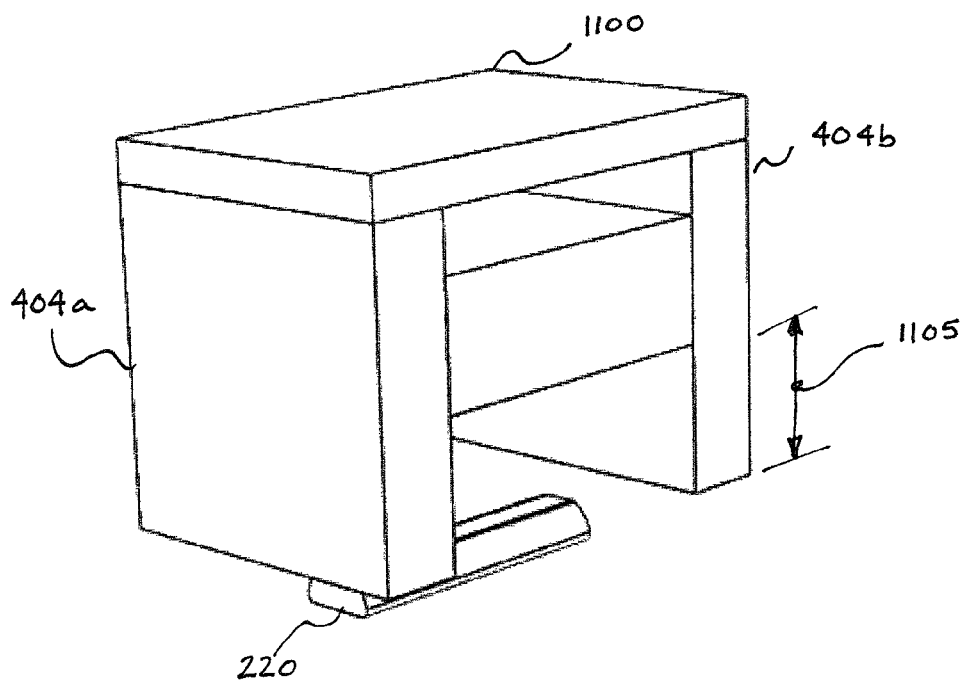
Figure 30F:
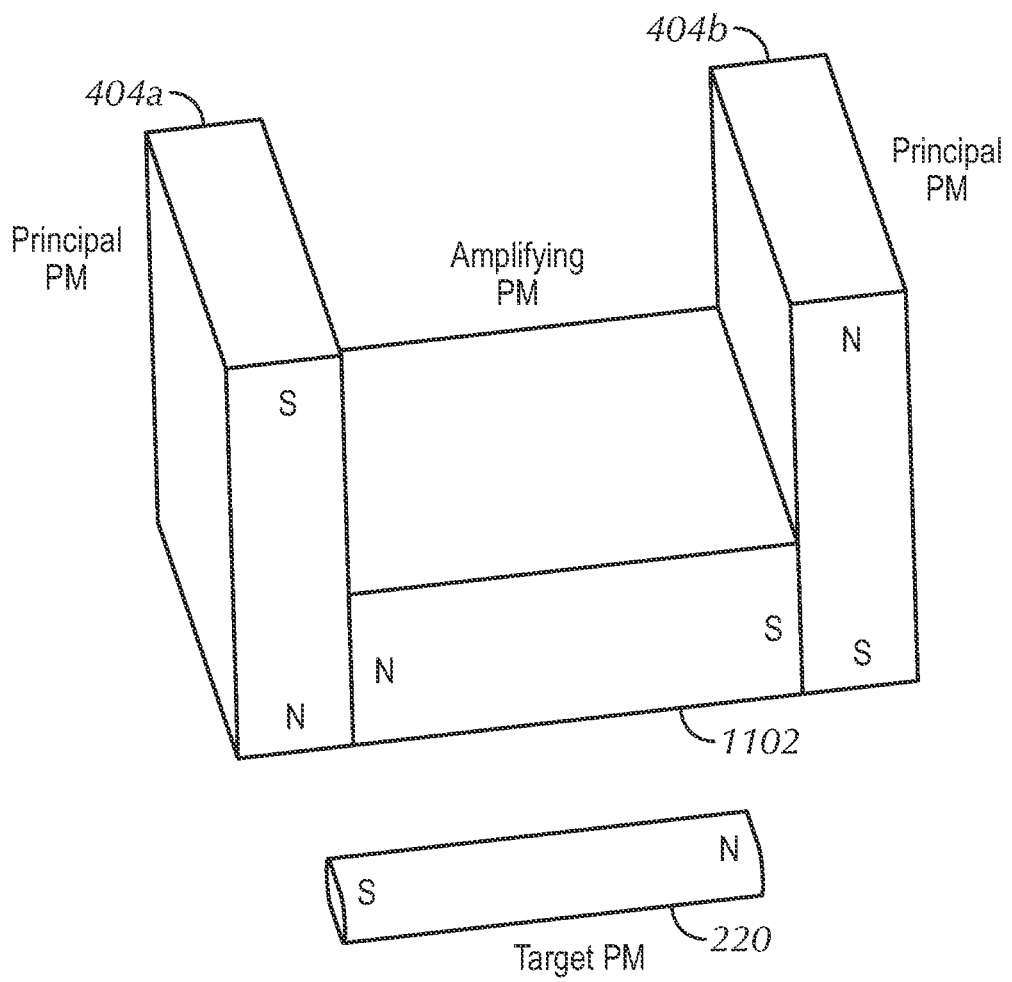

FIGS. 30A-30F illustrate embodiments of a system comprising first and second magnets 404a, 404b, frame member 1100, and third magnet 1102. FIG. 30A depicts a side view, FIG. 30B depicts a front view, and FIG. 30C depicts a bottom view of this embodiment. FIGS. 30E and 30D depict perspective views of first magnet 404a, showing third magnet 1102 configured to move relative to device 38 comprising magnet 220. FIG. 30F depicts a drawing showing magnets 404a having a S-N orientation, magnet 404b having a N-S orientation, and third magnet 1102 having an N-S orientation disposed between them such that N pole of third magnet 1102 is adjacent to N pole of magnet 404a, and S pole of third magnet 1102 is adjacent to S pole of magnet 404b.

As with the other embodiments and as shown in FIGS. 30A-30C, this embodiment also includes a platform configured to be magnetically coupled to an object disposed within a body cavity of a patient through a tissue 22. In some embodiments platform is apparatus 34 and object is device 38. In this embodiment, as shown in FIG. 30B, the platform includes a first magnet 404a having a first direction of magnetization, a second magnet 404b having a second direction of magnetization opposite the first direction of magnetization, and a third magnet 1102 disposed between the first and second magnets 404a, 404b and having a third direction of magnetization that is more perpendicular than parallel to each of the first and second directions of magnetization.

In a further embodiment, first magnet 404a may include an N pole and an S pole. Second magnet 404b may include an N pole and an S pole. Additionally, third magnet 1102 may include an N pole and an S pole. In such an embodiment, the N pole of first magnet 404a may be coupled to the N pole of third magnet 1102, and the S pole of second magnet 404b may be coupled to the S pole of third magnet 1102. Additionally, as shown in FIGS. 30D-30E, apparatus 34 may include an adjustment mechanism coupled to third magnet 1102 and configured to adjust the position of third magnet 1102 relative to first and second magnets 404a, 404b. Magnet 1102 may be configured to move closer to or further from the bottom of magnets 404a, 404b (closer to device 38) to modulate the magnetic force between magnets 404a, 404b and device 38 comprising magnet 220. Moving magnet 1102 closer to the bottom of magnets 404a, 404b will increase the magnetic force. Moving magnet 1102 further from the bottom of magnets 404a, 404b will decrease the magnetic force.

In some embodiments, frame member 1100 may provide lateral support to magnets 404a, 404b. In other embodiments, frame member 1100 may not be.

Figure 31A:
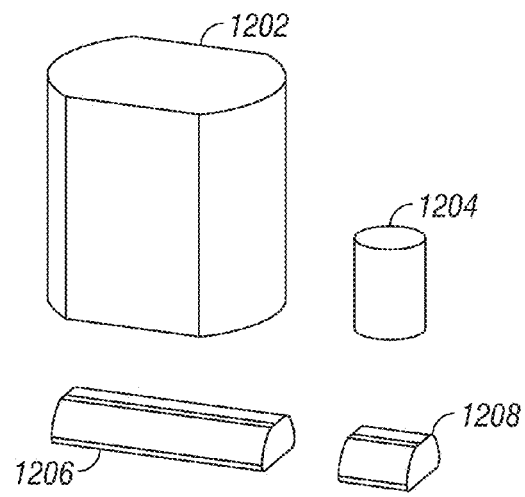
FIGS. 31A-31C illustrate embodiments of a configuration of magnets configured to modulate the strength of the primary magnetic field.
Figure 31B:
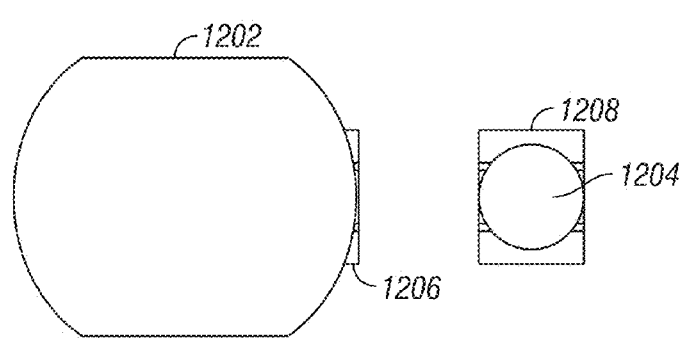
Figure 31C:
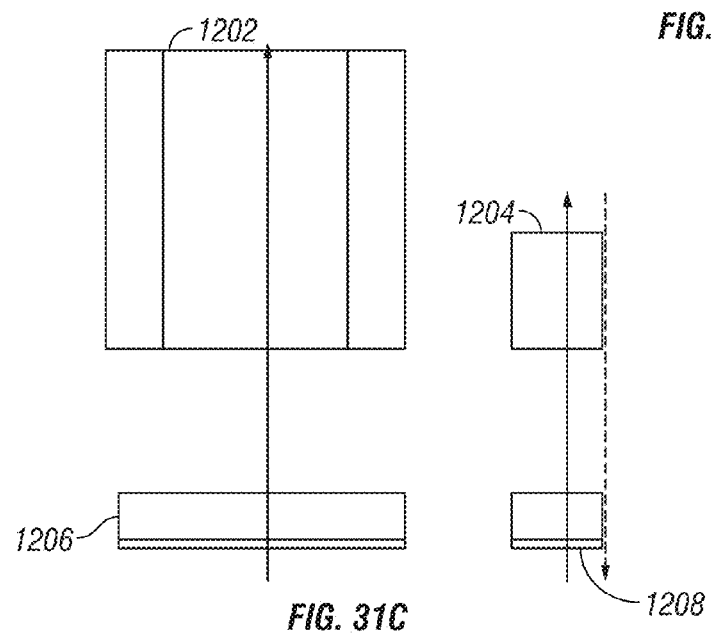

FIGS. 31A-31C illustrate embodiments of a system. In one embodiment, the system includes a first platform 38. First platform 38 may be inserted within a body cavity of a patient. Additionally, first platform 38 may include a first anchor magnet 1206 and a first pivot magnet 1208. In such an embodiment, the system may also include a second platform 34. Second platform 34 may be magnetically coupled to first platform 38 through a tissue 22. Second platform 34 may include a second anchor magnet 1202 and a second pivot magnet 1204. In one embodiment, second anchor magnet 1202 may be magnetically coupled to first anchor magnet 1206 and second pivot magnet 1204 may be magnetically coupled to first pivot magnet 1208. In particular, second anchor magnet 1202 may generate a stronger magnetic field than can second pivot magnet 1204.

In a further embodiment, first anchor magnet 1206 and second anchor magnet 1202 may anchor the first platform 38 to a position corresponding to a position of the second platform 34. Second pivot magnet 1204 may cause the first platform 38 to rotate about a vertical axis in response to corresponding movement of second pivot magnet 1204.

In a particular embodiment, second anchor magnet 1202 is larger than second pivot magnet 1204. In some embodiments, anchor magnets 1202, 1206 are relatively larger than pivot magnets 1204, 1208. In some embodiments, pivot magnets 1204, 1208 may have up to about 1%, 2%, 3%, 4%, 5%, 10%, 15%, 20%, 25%, 30%, 35%, or 40% of the volume of the anchor magnets. Additionally, first anchor magnet 1206 and second anchor magnet 1202 may have the same direction of magnetization as first pivot magnet 1208 and second pivot magnet 1204. Alternatively, first anchor magnet 1206 and second anchor magnet 1202 may have a different direction of magnetization from first pivot magnet 1208 and second pivot magnet 1204.

In some embodiments, first anchor magnet 1206 may be oriented N-S, second anchor magnet 1202 may be oriented N-S, first pivot magnet 1208 may be oriented S-N, and second pivot magnet 1204 may be oriented S-N. In some embodiments, first anchor magnet 1206 may be oriented N-S, second anchor magnet 1202 may be oriented N-S, first pivot magnet 1208 may be oriented N-S, and second pivot magnet 1204 may be oriented N-S.

Figure 32A:
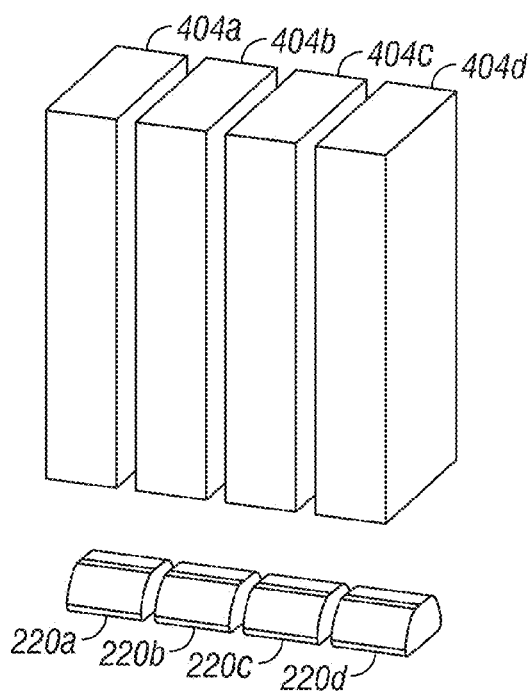
FIGS. 32A-32C illustrate embodiments of a configuration of magnets configured to modulate the strength of the primary magnetic field.
Figure 32B:
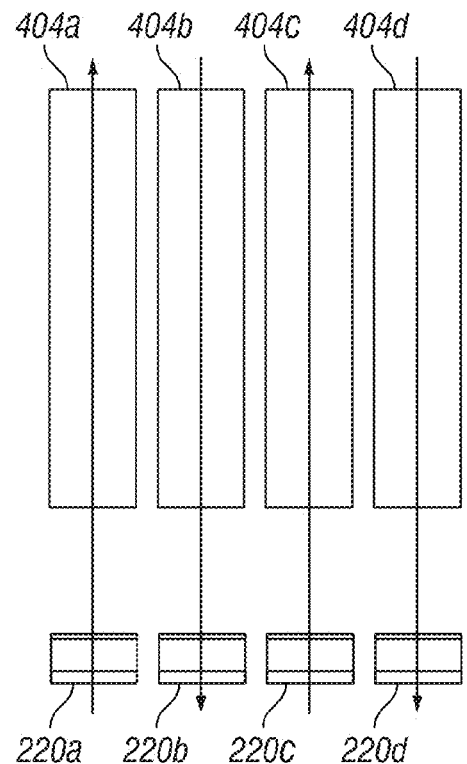
Figure 32C:
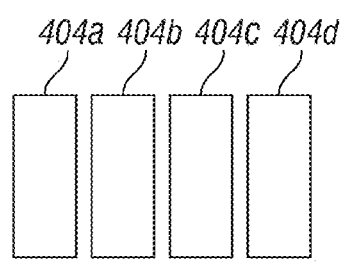

FIGS. 32A-32C illustrate embodiments of a system. FIG. 32A illustrates a perspective view, FIG. 32B illustrates a side view, and FIG. 32C illustrates a top view of embodiments of a system. In this embodiment, the system includes a first platform 38 and a second platform 34. First platform 38 may be inserted within a body cavity of a patient. Additionally, first platform 38 may include three or more first platform magnets 220. For example, first platform 38 may comprise four first platform magnets 220a, 220b, 220c, and 220d. Each first platform magnet 202 may have a direction of magnetization that is opposite to a direction of magnetization of an adjacent first platform 38 magnet. As used herein, the term "adjacent" means the nearest magnet in the same platform. For example, as illustrated in FIG. 32B, first platform magnets 220a and 220c may be magnetized in a N-S direction, while first platform magnets 220b and 220d may be magnetized in a S-N direction.

If a plurality of magnets are equidistant from a particular magnet then the plurality of magnets are adjacent to the particular magnet. In one embodiment, second platform 34 may be magnetically coupled to first platform 38 through a tissue 22. Second platform 34 may include three or more second platform magnets 404. For example, second platform 34 may comprise four first platform magnets 404a, 404b, 404c, and 404d. In one embodiment, each second platform 34 magnet has a direction of magnetization that is opposite to a direction of magnetization of an adjacent second platform 34 magnet and that corresponds to a direction of magnetization of a first platform 38 magnet. For example, if first platform magnets 220a and 220c are magnetized in a N-S direction, and first platform magnets 220b and 220d are magnetized in a S-N direction, second platform magnets 404a and 404c will be magnetized in a N-S direction and second platform magnets 404b and 404d will be magnetized in a S-N direction.

FIGS. 33A-34C depict embodiments of a medical device including internal platform 38 having a unitary magnet 220. FIG. 33A depicts a perspective view and FIG. 33B depicts a side view of one embodiment that includes an internal platform 38 configured to be inserted within a body cavity of a patient, where internal platform 38 has a unitary magnet 220 having a length taken along a longitudinal axis that is greater than any dimension of unitary magnet 220 taken along a line that is perpendicular to the longitudinal axis, where unitary magnet 220 has a top and a bottom and defining a central opening that extends from the top to the bottom. FIG. 33C depicts a heat map showing the strength of the magnetic field.

In a further embodiment, unitary magnet 220 is the only magnet of internal platform 38. The medical device may also include an external platform configured to be placed outside the body cavity and magnetically coupled to internal platform 38 through a tissue 22. In such an embodiment, the external platform may include a first magnet 404a and a second magnet 404b, first magnet 404a being configured to be magnetically coupled to a first portion 1304 of unitary magnet 220 on one side of the central opening and second magnet 404b being configured to be magnetically coupled to a second portion 1306 of unitary magnet 220 on another side of the central opening.

In the embodiments shown, unitary magnet 220 is charged in the same direction as magnets 404a, 404b. For example, if magnets 404a, 404b are charged N-S, unitary magnet 220 is also charged N-S.

FIGS. 34A-34C illustrate another embodiment of a medical device that includes an internal platform 38 configured to be inserted within a body cavity of a patient, internal platform 38 including a unitary magnet 220 that has a top, a bottom, a first longitudinal portion, a second longitudinal portion, and a central opening that extends from the top to the bottom and separates the first and second longitudinal portions, the unitary magnet 220 producing a magnetic field that is stronger over each of the first and second longitudinal portions than over the central opening. FIG. 34A depicts a perspective view and FIG. 34B depict perspective and side views, respectively, of the embodiment. Here, unitary magnet 220 is the only magnet of the internal platform 38. This embodiment may also include an external platform configured to be placed outside the body cavity and magnetically coupled to the internal platform 38 through a tissue 22, where the external platform may include a first magnet 404a and a second magnet 404b, first magnet 404a being configured to be magnetically coupled to the first longitudinal portion of unitary magnet 220 and second magnet 404b being configured to be magnetically coupled to the second longitudinal portion of unitary magnet 220.

Another medical device includes an internal platform 38 configured to be inserted within a body cavity of a patient, internal platform 38 including a unitary magnet 220 having a first portion 1304 separated from a second portion 1306 by a central portion 1302, where central portion 1302 is thinner than first and second portions 1302, 1306. Similarly, unitary magnet 220 is the only magnet of the internal platform 38.

Additional embodiments of the medical device include an internal platform 38 configured to be inserted within a body cavity of a patient. In one embodiment, internal platform 38 includes a unitary magnet 220 having a first portion 1304 separated from a second portion 1306 by a central portion 1302, where first and second portions 1304, 1306 are wider than central portion 1302. In another embodiment, the internal platform 38 including a unitary magnet 220 having a first portion 1304 separated from a second portion 1306 by a central portion 1302, where first and second portions, 1304, 1306 are wider than central portion 1302, and central portion 1302 is thinner than the first and second portions 1306. In still another embodiment, internal platform 38 includes a unitary magnet 220 having a first portion 1304 separated from a second portion 1306 by a central portion 1302, and unitary magnet 220 produces a magnetic field that is stronger over each of first and second portions 1304, 1306 than over central portion 1302.

Each of these various embodiments of the medical device may include an external platform 34 configured to be placed outside the body cavity and magnetically coupled to internal platform 38 through a tissue 22, where external platform 34 may include a first magnet 404a and a second magnet 404b, first magnet 404a being configured to be magnetically coupled to first portion 1304 of unitary magnet 220 and second magnet 404b being configured to be magnetically coupled to second portion 1306 of unitary magnet 220.

In the embodiments shown, unitary magnet 220 is charged in the same direction as magnets 404a, 404b. For example, if magnets 404a, 404b are charged N-S, unitary magnet 220 is also charged N-S.

The various illustrative embodiments of systems, apparatuses, devices, and methods described herein are not intended to be limited to the particular forms disclosed.

Rather, they include all modifications and alternatives falling within the scope of the claims. For example, arm 502 is depicted as being a threaded screw in FIG. 12A; however, other embodiments may include a spring loaded arm 502.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus comprising:
    a platform configured to be magnetically coupled to an object disposed within a body cavity of a patient through a tissue, the platform comprising:
        a first magnet having a first end, a second end, and a first longitudinal axis extending through the first and second ends, the first magnet further having a first direction of magnetization;
        a second magnet having a first end, a second end, and a second longitudinal axis extending through the first and second ends that is parallel to the first longitudinal axis, the second magnet further having a second direction of magnetization opposite the first direction of magnetization;
        a platform member coupled to the first magnet and the second magnet; and
        a third magnet having a substantially rectangular cross-sectional shape in a plane that is substantially parallel to the third direction of magnetization, the third magnet disposed between the first and second magnets and having a third direction of magnetization that is fixed relative to the platform member and more perpendicular than parallel to each of the first and second directions of magnetization;
        where the platform is configured to permit the third magnet to be moved relative to the first and second magnets, in a direction parallel to the first and second longitudinal axes, between any of a plurality of positions at which the third magnet is disposed between the first and second magnets.

2. The apparatus of claim 1, where:
    the first magnet comprises an N pole and an S pole;
    the second magnet comprises an N pole and an S pole;
    the third magnet comprises an N pole and an S pole;
    the N pole of the first magnet is coupled to the N pole of the third magnet; and
    the S pole of the second magnet is coupled to the S pole of the third magnet.

3. The apparatus of claim 2, where the position of the third magnet is adjustable relative to the first and second magnets.

4. The apparatus of claim 1, where
    the first longitudinal axis is parallel to the first direction of magnetization;
    the second longitudinal axis is parallel to the second direction of magnetization;
    a longitudinal dimension of the first magnet is greater than any dimension of the first magnet that is taken along a line that is perpendicular to the first longitudinal axis; and
    a longitudinal dimension of the second magnet is greater than any dimension of the second magnet that is taken along a line that is perpendicular to the second longitudinal axis.

5. The apparatus of claim 4, further comprising the object configured to be inserted within a body cavity of a patient and magnetically coupled to the platform across a tissue, the object having a fourth magnet that has an N pole and an S pole along an axis that is more perpendicular to than parallel with the first longitudinal axis of the first magnet of the platform.

6. The apparatus of claim 1, further comprising the object configured to be inserted within a body cavity of a patient and magnetically coupled to the platform across a tissue, the object having a single fourth magnet that has an N pole and an S pole along an axis that is more perpendicular to than parallel with the first longitudinal axis of the first magnet of the platform.

* * * * *